United States Patent [19]

Amoo

[11] Patent Number: 5,444,079
[45] Date of Patent: Aug. 22, 1995

[54] ARTHROPODICIDAL OXAZOLINES

[75] Inventor: Victor E. Amoo, Newark, Del.

[73] Assignee: E. I. Du Pont de Nemours and Company, Wilmington, Del.

[21] Appl. No.: 318,742

[22] PCT Filed: Apr. 21, 1993

[86] PCT No.: PCT/US93/03563

§ 371 Date: Oct. 19, 1994

§ 102(e) Date: Oct. 19, 1994

[87] PCT Pub. No.: WO93/21165

PCT Pub. Date: Oct. 28, 1993

Related U.S. Application Data

[63] Continuation of Ser. No. 976,587, Nov. 16, 1992, abandoned, which is a continuation of Ser. No. 872,493, Apr. 23, 1992, abandoned.

[51] Int. Cl.$^6$ ..................... A61K 31/42; C07D 263/12
[52] U.S. Cl. ..................................... 514/374; 548/216
[58] Field of Search ........................ 548/216; 514/374

[56] References Cited

U.S. PATENT DOCUMENTS 4,544,662 10/1985 Brittain et al. ..................... 514/374

FOREIGN PATENT DOCUMENTS 0345775 12/1989 European Pat. Off. ... C07D 263/10
0432661 6/1991 European Pat. Off. ... C07D 263/12
7409253 1/1975 Netherlands ............... C07D 263/06

OTHER PUBLICATIONS

Dirlam, N. L. et al., "Novel Synthesis of the Aldose Reductase Sorbinil via Amidoalkylation, Intramolecular Oxazolidin-5-one Alkylation, and Chymotriypsin Resolution", *J. Org. Chem.*, 52, 3587-3591 (1987).
Miyamoto, S. et al, *Chemical Abstracts*, 117(13), Sep. 28, 1992, Abstract No. 131181s.

*Primary Examiner*—Robert W. Ramsuer
*Assistant Examiner*—Laura R. Cross

[57] ABSTRACT

Arthropodicidal compounds, compositions and methods of use of compounds having formula (I) wherein A, G, Z and $R^1$ to $R^4$, are as defined in the text.

5 Claims, No Drawings

ARTHROPODICIDAL OXAZOLINES

This application is a 371 of PCT US 93/03563 filed on Apr. 21, 1993 which is a continuation of application Ser. No. 07/976,587, filed Nov. 16, 1992, now abandoned, which is a continuation of application Ser. No. 07/872,493, filed Apr. 23, 1992, now abandoned.

This invention pertains to spirocyclic oxa- and thiazolines as arthropodicides. EP 345,775 and EP 432,661 disclose non-spirocyclic oxa- and thia-zolines as insecticides.

SUMMARY OF THE INVENTION

The invention pertains to compounds of Formula I, including all geometric and stereoisomers, agriculturally suitable salts thereof, agricultural compositions containing them and their use as arthropodicides in both agronomic and nonagronomic environments. The compounds are

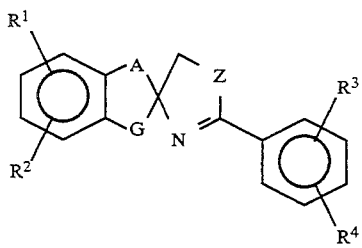

I wherein
A is selected from the group a direct bond, O, S, —$XCH_2$— and $C_1$-$C_3$ straight or branched chain alkylene; when A is —$XCH_2$—, the point of attachment to the phenyl ring is X or $CH_2$;

G is selected from the group O, S, —$CH_2$—Y—$CH_2$—, —Y($CH_2$)$_m$— and $C_1$-$C_3$ straight or branched chain alkylene; when G is —Y($CH_2$)$_m$—, the point of attachment to the phenyl ring is Y or the terminal carbon, and the ring containing A and G has 5–7 members;

X and Y are independently selected from the group O and S;

Z is selected from the group O and S;

$R^1$ is selected from the group H, halogen, $C_1$-$C_6$ alkyl, $C_1$-$C_6$ alkoxy, $C_1$-$C_6$ haloalkyl and $C_1$-$C_6$ haloalkoxy;

$R^2$ is selected from the group H, halogen, $C_1$-$C_{16}$ alkyl, $C_3$-$C_7$ cycloalkyl, $C_4$-$C_7$ cycloalkylalkyl, $C_1$-$C_{16}$ haloalkyl, $C_2$-$C_{16}$ alkenyl, $C_2$-$C_{16}$ haloalkenyl, $C_2$-$C_{16}$ alkynyl, $C_2$-$C_{16}$ haloalkynyl, $C_2$-$C_{16}$ alkoxyalkoxy, $OR^5$, $R^5OC(O)$—, $R^5C(O)$— and

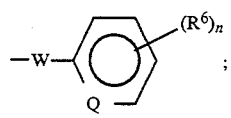

W is selected from the group direct bond, S, O, C(=O), C(=O)O, C(=O)O—$C_1$-$C_2$ alkylene, $C_1$-$C_4$ alkylene, O—$C_1$-$C_4$ alkylene and O—$C_2$-$C_4$ alkenylene, wherein when W is O—$C_1$-$C_4$ alkylene or O—$C_2$-$C_4$ alkenylene, the oxygen atom can be attached to either aromatic ring and when W is C(=O)O or C(=O)O—$C_1$-$C_2$, the C(=O) moiety can be attached to either aromatic ring;

Q is selected from CH and N;

$R^3$ and $R^4$ are independently selected from the group H, halogen, $C_1$-$C_6$ alkyl, $C_1$-$C_6$ haloalkyl, $C_1$-$C_6$ haloalkoxy, $C_1$-$C_6$ alkylthio, CN and $NO_2$;

$R^5$ is selected from the group H, $C_3$-$C_7$ cycloalkyl, $C_4$-$C_{16}$ cycloalkylalkyl, $C_1$-$C_{16}$ alkyl, $C_1$-$C_{16}$ haloalkyl, $C_2$-$C_{16}$ alkenyl, $C_2$-$C_{16}$ haloalkenyl, $C_2$-$C_{16}$ alkynyl and $C_2$-$C_{16}$ haloalkynyl;

$R^6$ is selected from the group halogen, $C_1$-$C_{10}$ alkyl, $C_1$-$C_{10}$ alkoxy, $C_1$-$C_{10}$ haloalkyl, $C_1$-$C_{10}$ haloalkoxy and Si($R^7$)($R^8$)$R^9$;

$R^7$, $R^8$ and $R^9$ are independently $C_1$-$C_3$ alkyl;

m is 1 or 2; and n is 0 or an integer from 1 to 5.

Preferred Compounds A are compounds of Formula I wherein:
A is a direct bond;
G is selected from the group $C_2$-$C_3$ alkylene, —$CH_2$—Y—$CH_2$—, and —Y($CH_2$)$_m$—;
$R^1$ is selected from the group H and halogen; and
$R^3$ and $R^a$ are independently selected from the group H, F and Cl.

Specifically preferred for biological activity is the compound of Preferred A which is
2′-(2,6-difluorophenyl)-3,4-dihydro-6-octyloxyspiro-[naphthalene-1(2H),4′(5′H)-oxazole].

Compounds of this invention can exist as one or more stereoisomers. The various stereoisomers include enantiomers, diastereomers and geometric isomers. One skilled in the an will appreciate that one stereroisomer may be more active than the others and how to separate stereoisomers. Accordingly, the present invention comprises racemic mixtures, individual stereoisomers, and optically active mixtures of compounds of Formula I as well as their agriculturally suitable salts.

In the above recitations, the term "alkyl" used either alone or in compound word such as "alkylthio" or "haloalkyl", denotes straight or branched alkyl such as methyl, ethyl, n-propyl, isopropyl and the different butyl, pentyl and hexyl isomers. Similarly, the terms "alkylene" and "alkenylene" denote straight or branched chain groups.

Alkoxy denotes methoxy, ethoxy, n-propyloxy, isopropyloxy and the different butoxy, pentoxy and hexyloxy isomers. Alkenyl denotes straight or branched chain alkenes such as vinyl, 1-propenyl, 2-propenyl, and the different butenyl, pentenyl and hexenyl isomers. Alkynyl denotes straight chain or branched alkynes such as ethynyl, 1-propynyl, 3-propynyl and the different butynyl, pentynyl and hexynyl isomers. Cycloalkyl denotes cyclopropyl, cyclobutyl, cyclopentyl and cyclohexyl.

The term "halogen", either alone or in compound words such as "haloalkyl", denotes fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$. The terms "haloalkenyl" and "haloalkynyl" are defined analogously to the term "haloalkyl".

The total number of carbon atoms in a substituent group is indicated by the "$C_i$-$C_j$" prefix where i and j are numbers from 1 to 16. For example, $C_4$alkoxyalkoxy designates the various isomers of an alkoxy group substituted with a second alkoxy group containing a total of 4 carbon atoms, examples including OCH$_2$OCH$_2$CH$_2$CH$_3$ and OCH$_2$CH$_2$OCH$_2$CH$_3$. When a compound is substituted with a substituent bearing a subscript indicated by a lower case letter which allows the number of said substituents to exceed 1, said substituent (when they exceed 1) are independently selected from the group of defined substituents.

DETAILS OF THE INVENTION

Compounds of Formula I are prepared as described in Schemes 1 through 6 with substituents as previously defined, unless otherwise noted. Compounds of Formula I can be prepared by treatment of Formula II compounds with a dehydrating agent such as sulfuric acid, polyphosphoric acid, phosphorous pentoxide, thionyl chloride, dicyclohexylcarbodiimide and phosphorous pentasulfide. Sulfuric acid, polyphosphoric acid, phosphorous pentoxide, thionyl chloride and dicyclohexylcarbodiimide produce Formula I compounds where X is oxygen, while use of phosphorous pentasulfide produces Formula I compounds where X is sulfur. Typical reactions involve the combination of a Formula II compound with an excess molar amount of the dehydrating agent (1.1 equivalents to 20 equivalents) in the presence or absence of a solvent such as benzene, toluene, xylene, chlorobenzene or dichlorobenzene. The reaction temperature can vary from 0° C. to the reflux temperature of the solvent being used. The reaction is usually complete in 24 hours. Alternatively, this transformation can be achieved by treatment of Formula II compounds with triphenylphosphine and carbon tetrachloride in the presence of a tertiary amine base such as methylamine. The reaction can be run in a suitable solvent such as acetonitrile. The reaction temperature can vary from about 0° C. to 60° C. The reaction is usually complete in 24 hours. (See Tetrahedron Letters, (1981), 22,4471). Scheme 1 illustrates this transformation.

Scheme 1

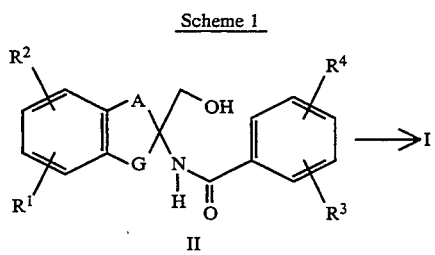

Compounds of Formula II can be prepared by the reaction of an aminoalcohol III with a substituted acid chloride of Formula IV in equimolar proportions in the presence of an excess of an acid scavenger, such as tertiary alkylamines or pyridines, in an aprotic organic solvent such as ether, tetrahydrofuran, chloroform, methylene chloride, benzene or toluene. The reaction temperature can vary from about −20° C. to 100° C. with 0° C. to 50° C. being preferred. The reaction is generally complete after 24 hours. Scheme 2 illustrates this transformation.

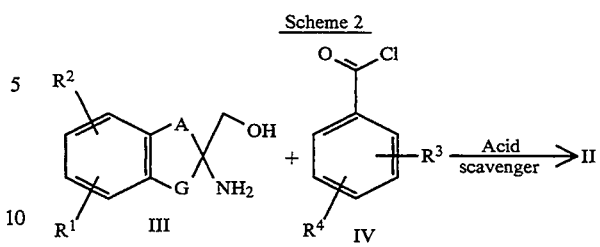

Compounds of Formula III can be prepared by the reduction of Formula V compounds. Typical reactions involve combination of an excess in molar amounts of a reducing agent (4 equivalents to 10 equivalents) such as lithium aluminum hydride with one equivalent of a Formula V compound in a solvent such as tetrahydrofuran or ether. The reaction temperatures can vary from about 0° C. to the reflux temperature of the particular solvent being used. This transformation is illustrated in Scheme 3.

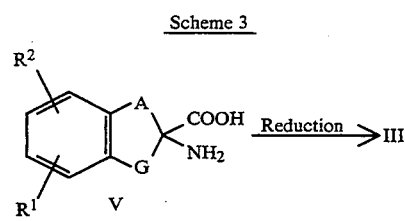

Compounds of Formula V can be prepared by the hydrolysis of hydantoins of Formula VI. A typical reaction involve combination of a Formula VI compound with an excess in molar amounts (2 equivalents to 20 equivalents) of a base such as barium hydroxide, potassium hydroxide or sodium hydroxide in a solvent such as water, methanol, ethanol or isopropanol. The reaction temperature can vary from about 50° C. to the reflux temperature of the particular solvent being used. The reaction time can vary from about 24 hours to ten days. Scheme 4 illustrates this transformation.

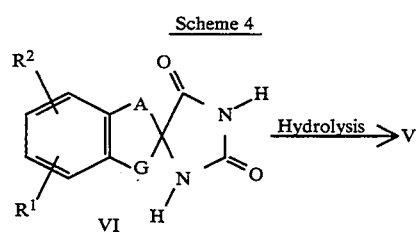

Compounds of Formula VI can be prepared from Formula VII compounds. Treatment of a Formula VII compound with an excess of potassium cyanide or sodium cyanide and ammonium carbonate in a solvent such as ethanol, methanol and/or water, produces compounds of Formula VI (See J. Med. Chem., 1988, 31, 230). This transformation is illustrated in Scheme 5.

Scheme 5

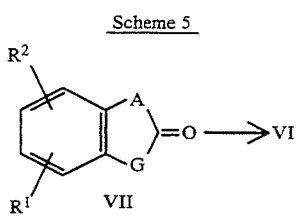

VII

The starting ketones of Formula VII are known in the art or can be obtained by methods analogous to known procedures. Those skilled in the art will recognize the Formula VII compounds to include indanones, tetralones, chromanones, thiochromanones, benzofuran-3-ones, isochromanones and others.

Alternatively, compounds of Formula I (where $R^2$ is $-OR^5$ or $R^5C(O)O-$) can be prepared by the reaction of compounds of the Formula VIII with an electrophile of Formula IX in the presence of a suitable base such as alkali metal, alkali alkoxide, tertiary amine or metal hydride. The reaction can be run in a conventional organic solvent such as chloroform, methylene chloride, tetrahydrofuran, ether or dimethylformamide. The reaction temperature can vary from about $-10°$ C. to $100°$ C. This transformation is illustrated in Scheme 6.

Scheme 6

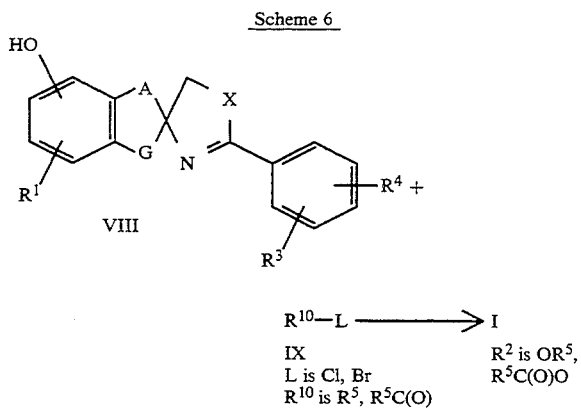

IX
L is Cl, Br
$R^{10}$ is $R^5$, $R^5C(O)$ $R^2$ is $OR^5$,
$R^5C(O)O$

The preparation of Formula VIII compounds can be accomplished by cleavage of Formula I compounds (where $R^2$ is OMe). Ether cleavages are known in the art and a comprehensive review can be found in *Synthesis*, 1983, 249.

EXAMPLE 1

Step A:
3′,4′-dihydro-6′-methoxyspiro[imidazolidine-4,1′(2′H)-naphthalene]-2,5-dione A mixture of 35.2 g (0.2 mol) of 6-methoxy-1-tetralone, 19.5 g (0.3 mol) of potassium cyanide and 134.4 g (1.4 mol) of ammonium carbonate in 280 mL of EtOH was placed in a stainless steel bomb and heated at 110° C. for 48 hours. After cooling, the mixture was poured in 1.4 L of water. It was allowed to sit at ambient temperature for 3 days. The precipitated solid was filtered and washed several times with water and dried to give 48.1 g of a brown solid: mp 218°–220° C. $^1$H-NMR (DMSO-d$_6$)d10.75(s, 1H),8.45(s, 1H),6.96(d, 1H),6.79 (d, 1H), 6.70 (s, 1H), 3.72 (s, 3H), 2.73 (t, 2H), 1.70–2.20 (m, 4H).

Step B:
1-amino-1,2,3,4-tetrahydro-6-methoxy-1-naphthalenecarboxylic acid

To a suspension of 2.95 g (0.012 mol) of the product of Step A in 100 mL of water was added 15.1 g (0.0479 mol) of barium hydroxide octahydrate. The reaction was heated at reflux for 3 days. To the reaction mixture was carefully added 6.4 g (0.067 mol) of ammonium carbonate. Refluxing was continued for another 2 hours. The solid was filtered off while hot and the pH of the filtrate adjusted to 6. The filtrate was then concentrated to give 1.86 g of a tan solid: mp>250° C. $^1$H NMR (D$_2$O) d 7.20 (d, 1H), 6.85 (d and s, 2H), 3.835 (s, 3H), 2.85 (t, 2H), 1.70–2.40 (m, 4H).

Step C:
1-amino-1,2,3,4-tetrahydro-6-methoxy-1-naphthalenemethanol

To a suspension of 172 mg (0.00452 mol) of lithium aluminum hydride in 6 mL of THY at 0° C. was added portion-wise 500 mg (0.00226 mol) of the product of Step B. The mixture was refluxed overnight. EtOAc was carefully added to quench excess hydride and 50% aqueous NaOH added. The mixture was extracted with EtOAc and the EtOAc extract washed with brine. It was dried (MgSO$_4$) and concentrated to give an oil which solidified on standing to give 390 mg of a tan solid: mp 89°–95.6° C. $^1$H NMR (DMSO-d$_6$) d 7.422 (d, 1H), 6.70 (d, 1H), 6.95 (s, 1H), 3.690 (s, 3H), 3.20–3.40 (m, 3H), 2.70 (t, 2H), 2.0–2.20 (m. 2H), 1.70 (m, 2H).

Step D:
2,6-difluoro-N-[1,2,3,4-tetrahydro-1-(hydroxymethyl)-6-methoxy-1-naphthalenyl]benzamide To a stirring mixture of 2.0 g (0.00965 mol) of the product of Step C, 976 mg (0.00965 mol) of methylamine in 30 mL of THF at 0° C. was added dropwise a solution of 2,6-difluorobenzoylchloride in 15 mL of THF. The reaction mixture was stirred at ambient temperature for 30 minutes. The precipitated triethylamine hydrochloride was filtered off and the filtrate concentrated. It was purified by passing through a silica gel column eluting with EtOAc:Hexane (2:3) to afford a white solid: mp 174°–175° C. 1H NMR (CDCl$_3$) d 7.30 (m, 2H), 6.90 (t, 2H), 6.85 (dd, 1H), 6.60 (d, 1H), 6.35 (broad s, 1H), 4.80 (dd, 1H), 4.20 (dd, 1H), 3.77 (s, 3H), 3.75 (d, 2H), 2.80 (m, 2H), 2.30 (m, 2H), 1.90 (m, 2H).

Step E: 2′-(2,6-difluorophenyl)-3,4-dihydro-6-methoxy spiro [naphthalene-1(2H),4′(5′H)-oxazole]

To a suspension of 600 mg (0.0017 mol) of the product of Step D in 9 mL of acetonitrile was added 1.8 mL CCl$_4$ and 264 mg (0.0026 mol) of methylamine. Then, 678 mg (0.0026 mol) of triphenylphosphine was added. The mixture was stirred at ambient temperature for 15 minutes.

The precipitated triphenylphosphine oxide was filtered and the filtrate concentrated. The residue was purified by passing through a silica gel column eluting with methylene chloride to give 520 mg of an oil which solidified on standing: mp 64°–67° C. $^1$H NMR (CDCl$_3$) d 7.40 (m, 1H), 7.25 (d, 1H), 6.99 (m, 2H), 6.80 (dd, 1H), 6.62 (d, 1H), 4.25 (dd, 2H), 3.79 (s, 3H), 2.80 (m, 2H), 1.75–2.20 (m, 4H).

Step F: 2'-(2,6-difluorophenyl)-3,4-dihydrospiro [naphthalene-1(2H), 4'(5'H)-oxazole]-6-ol Aluminum chloride, 600 mg (0.00764 mol), was added to 5 mL of ethanethiol at 0° C. Then, 250 mg (0.0076 mol) of the product of Step E was added at once. The reaction was stirred at 0° C. for 10 minutes. It was quenched with MeOH at 0° C., poured into saturated aqueous NaHCO$_3$ solution and extracted with EtOAc:THF (1:1). The combined extracts were dried (MgSO4) and concentrated to give 230 mg of a white solid. $^1$H NMR (DMSO-d$_6$) d 9.31 (s, 1H), 7.65 (m, 1H), 7.27 (t, 2H), 6.96 (d, 1H), 6.60 (dd, 1H), 6.49 (d, 1H), 4.35 (dd, 2H), 2.70 (broad, 2H), 1.70–2.0 (m, 4H).

Step G: 2'-(2,6-difluorophenyl)-3,4-dihydro-6-octyloxyspiro[- naphthalene-1(2H), 4'(5'H)-oxazole]

To a suspension of 64 mg (0.00127 mol) of NaH in 1 mL of DMF at 0° C. was added a partial solution of 200 mg (0.00063 mol) of the product of Step F. The reaction was stirred at 0° C. for 30 minutes. Then, 304 mg (0.00127 mol) of 1-iodooctane was added and stirring continued for an additional 30 minutes at 0° C. The reaction mixture was poured into ice-water and extracted with Et$_2$O. The Et$_2$O extract was washed with brine, dried (MgSO$_4$) and concentrated. The residue was purified by passing through a silica gel column eluting with EtOAc:Hexanes (1:4) to give 240 mg of a clear oil. $^1$H NMR (CDCl$_3$) d 7.40 (m, 1H), 7.20 (d, 1H), 6.98 (Ab q, 2H), 3.92 (t, 2H), 2.80 (m, 2H), 1.70–2.20 (m, 4H), 1.20–1.45 (m, 12H), 0.90 (t, 3H).

By the procedures described herein the compounds of Tables 1 to 8 can be prepared. The compounds in Table 1, row 1 can be referred to as 1-1-1, 1-1-2 and 1-1-3 (as designated by Table number, line number and column number). All of the other specific compounds covered in these Tables can be designated in an analogous manner by Table, line and column. Abbreviations used in Tables: Ph=phenyl, Py=2-pyridyl.

STRUCTURES FOR TABLES

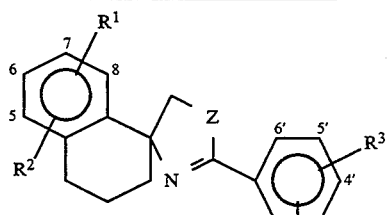

Table 1

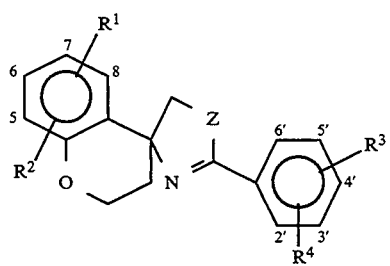

Table 2

STRUCTURES FOR TABLES -continued

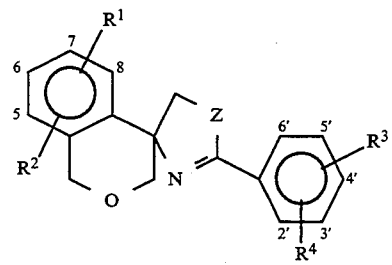

Table 3

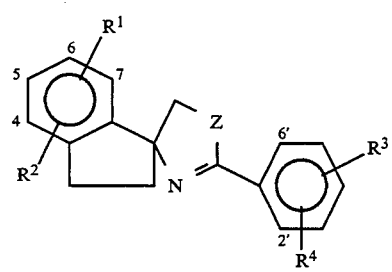

Table 4

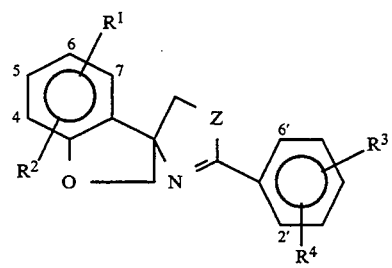

Table 5

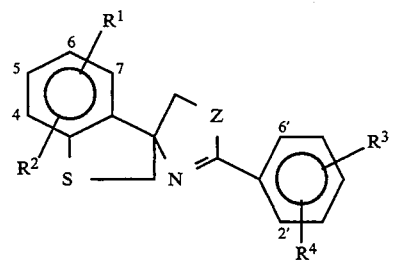

Table 6

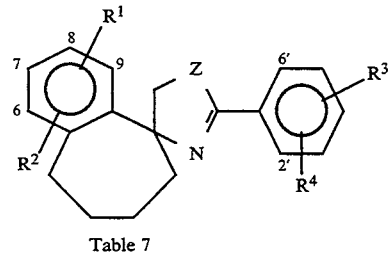

Table 7

-continued
STRUCTURES FOR TABLES

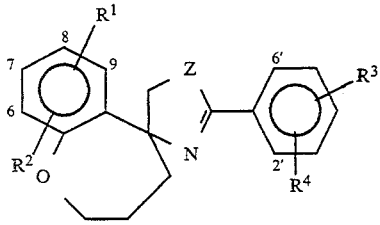

Table 8

TABLE 1

| | Column 1 | Column 2 | Column 3 |
|---|---|---|---|
| | $Z = O, R^1 = H, R^3 = 2'\text{-}F, R^4 = 6'\text{-}F, R^2 =$ | | |
| 1 | H | 6-(4-Cl—Ph) | 6-$CH_2CH$=$CH(CH_2)_6CH_3$ |
| 2 | 6-Cl | 6-(4-F—Ph) | 6-$CH_2CH$=$CH(CH_2)_2CH_3$ |
| 3 | 6-F | 6-$CH_2Ph$ | 6-$OCH_2CH$=$CH(CH_2)_6CH_3$ |
| 4 | 6-Br | 6-$CH_2CH_2Ph$ | 6-$OCH_2CH$=$CH(CH_2)_2CH_3$ |
| 5 | 6-$CF_3$ | 6-$CH_2Ph$-4-F | 6-$OCH_2Ph$-4-F |
| 6 | 6-Ph | 6-$CH_2Ph$-4-Cl | 6-$OCH_2CH_2Ph$-4-F |
| 7 | 6-Py | 6-$CH_2Ph$-4-$CF_3$ | 6-$CH_2C$≡$C$—$(CH_2)_4CH_3$ |
| 8 | 6-OPh | 6-(4-$CH_3(CH_2)_4Ph$) | 6-$OCH_2C$≡$C$—$(CH_2)_4CH_3$ |
| 9 | 6-SPh | 6-$CH_2Ph$-4-$(CH_2)_9CH_3$ | 6-$CH_2CH$=$CH$—$CH_2Ph$ |
| 10 | 6-OPy | 6-$CH_2Ph$-4-$(CH_2)_4CH_3$ | 6-$OCH_2CH$=$CH$—$CH_2Ph$ |
| 11 | 7-Cl | 7-(4-Cl—Ph) | 7-$CH_2CH$=$CH(CH_2)_6CH_3$ |
| 12 | 7-$CF_3$ | 7-$CH_2Ph$ | 7-$OCH_2CH$=$CH(CH_2)_6CH_3$ |
| 13 | 7-Ph | 7-$CH_2CH_2Ph$ | 7-$OCH_2CH$=$CH(CH_2)_2CH_3$ |
| 14 | 7-OPh | 7-$CH_2Ph$-4-$CF_3$ | 7-$CH_2C$≡$C$—$(CH_2)_4CH_3$ |
| 15 | 6-$O(CH_2)_5CH_3$ | 6-$O(CH_2)_3CH(CH_3)_2$ | 6-$O(CH_2)_2CH(CH_3)CH_2CH_3$ |
| 16 | 6-$O(CH_2)_6CH_3$ | 6-$O(CH_2)_4CH(CH_3)_2$ | 6-$O(CH_2)_3CH(CH_3)CH_2CH_3$ |
| 17 | 6-$O(CH_2)_7CH_3$ | 6-$O(CH_2)_5CH(CH_3)_2$ | 6-$O(CH_2)_4CH(CH_3)CH_2CH_3$ |
| 18 | 6-$O(CH_2)_8CH_3$ | 6-$O(CH_2)_6CH(CH_3)_2$ | 6-$O(CH_2)_5CH(CH_3)CH_2CH_3$ |
| 19 | 6-$O(CH_2)_9CH_3$ | 6-$O(CH_2)_7CH(CH_3)_2$ | 6-$O(CH_2)_6CH(CH_3)CH_2CH_3$ |
| 20 | 6-$O(CH_2)_{11}CH_3$ | 6-$O(CH_2)_9CH(CH_3)_2$ | 6-$O(CH_2)_8CH(CH_3)CH_2CH_3$ |
| 21 | 6-$O(CH_2)_{15}CH_3$ | 6-$O(CH_2)_{13}CH(CH_3)_2$ | 6-$O(CH_2)_{12}CH(CH_3)CH_2CH_3$ |
| 22 | 7-$O(CH_2)_{11}CH_3$ | 7-$O(CH_2)_9CH(CH_3)_2$ | 7-$O(CH_2)_8CH(CH_3)CH_2CH_3$ |
| 23 | 6-$(CH_2)_5CH_3$ | 6-$(CH_2)_3CH(CH_3)_2$ | 6-$(CH_2)_2CH(CH_3)CH_2CH_3$ |
| 24 | 6-$(CH_2)_6CH_3$ | 6-$(CH_2)_4CH(CH_3)_2$ | 6-$(CH_2)_3CH(CH_3)CH_2CH_3$ |
| 25 | 6-$(CH_2)_7CH_3$ | 6-$(CH_2)_5CH(CH_3)_2$ | 6-$(CH_2)_4CH(CH_3)CH_2CH_3$ |
| 26 | 6-$(CH_2)_8CH_3$ | 6-$(CH_2)_6CH(CH_3)_2$ | 6-$(CH_2)_5CH(CH_3)CH_2CH_3$ |
| 27 | 6-$(CH_2)_9CH_3$ | 6-$(CH_2)_7CH(CH_3)_2$ | 6-$(CH_2)_6CH(CH_3)CH_2CH_3$ |
| 28 | 6-$(CH_2)_{11}CH_3$ | 6-$(CH_2)_9CH(CH_3)_2$ | 6-$(CH_2)_8CH(CH_3)CH_2CH_3$ |
| 29 | 6-$(CH_2)_{15}CH_3$ | 6-$(CH_2)_{13}CH(CH_3)_2$ | 6-$(CH_2)_{12}CH(CH_3)CH_2CH_3$ |
| 30 | 7-$(CH_2)_{11}CH_3$ | 7-$(CH_2)_9CH(CH_3)_2$ | 7-$(CH_2)_8CH(CH_3)CH_2CH_3$ |
| | $Z = O, R^1 = H, R^3 = 2'\text{-}F, R^4 = 6'\text{-}Cl, R^2 =$ | | |
| 31 | H | 6-(4-Cl—Ph) | 6-$CH_2CH$=$CH(CH_2)_6CH_3$ |
| 32 | 6-Cl | 6-(4-F—Ph) | 6-$CH_2CH$=$CH(CH_2)_2CH_3$ |
| 33 | 6-F | 6-$CH_2Ph$ | 6-$OCH_2CH$=$CH(CH_2)_6CH_3$ |
| 34 | 6-Br | 6-$CH_2CH_2Ph$ | 6-$OCH_2CH$=$CH(CH_2)_2CH_3$ |
| 35 | 6-$CF_3$ | 6-$CH_2Ph$-4-F | 6-$OCH_2Ph$-4-F |
| 36 | 6-Ph | 6-$CH_2Ph$-4-Cl | 6-$OCH_2CH_2Ph$-4-F |
| 37 | 6-Py | 6-$CH_2Ph$-4-$CF_3$ | 6-$CH_2C$≡$C$—$(CH_2)_4CH_3$ |
| 38 | 6-OPh | 6-(4-$CH_3(CH_2)_4Ph$) | 6-$OCH_2C$≡$C$—$(CH_2)_4CH_3$ |
| 39 | 6-SPh | 6-$CH_2Ph$-4-$(CH_2)_9CH_3$ | 6-$CH_2CH$=$CH$—$CH_2Ph$ |
| 40 | 6-OPy | 6-$CH_2Ph$-4-$(CH_2)_4CH_3$ | 6-$OCH_2CH$=$CH$—$CH_2Ph$ |
| 41 | 7-Cl | 7-(4-Cl—Ph) | 7-$CH_2CH$=$CH(CH_2)_6CH_3$ |
| 42 | 7-$CF_3$ | 7-$CH_2Ph$ | 7-$OCH_2CH$=$CH(CH_2)_6CH_3$ |
| 43 | 7-Ph | 7-$CH_2CH_2Ph$ | 7-$OCH_2CH$=$CH(CH_2)_2CH_3$ |
| 44 | 7-OPh | 7-$CH_2Ph$-4-$CF_3$ | 7-$CH_2C$≡$C$—$(CH_2)_4CH_3$ |
| 45 | 6-$O(CH_2)_5CH_3$ | 6-$O(CH_2)_3CH(CH_3)_2$ | 6-$O(CH_2)_2CH(CH_3)CH_2CH_3$ |
| 46 | 6-$O(CH_2)_6CH_3$ | 6-$O(CH_2)_4CH(CH_3)_2$ | 6-$O(CH_2)_3CH(CH_3)CH_2CH_3$ |
| 47 | 6-$O(CH_2)_7CH_3$ | 6-$O(CH_2)_5CH(CH_3)_2$ | 6-$O(CH_2)_4CH(CH_3)CH_2CH_3$ |
| 48 | 6-$O(CH_2)_8CH_3$ | 6-$O(CH_2)_6CH(CH_3)_2$ | 6-$O(CH_2)_5CH(CH_3)CH_2CH_3$ |
| 49 | 6-$O(CH_2)_9CH_3$ | 6-$O(CH_2)_7CH(CH_3)_2$ | 6-$O(CH_2)_6CH(CH_3)CH_2CH_3$ |
| 50 | 6-$O(CH_2)_{11}CH_3$ | 6-$O(CH_2)_9CH(CH_3)_2$ | 6-$O(CH_2)_8CH(CH_3)CH_2CH_3$ |
| 51 | 6-$O(CH_2)_{15}CH_3$ | 6-$O(CH_2)_{13}CH(CH_3)_2$ | 6-$O(CH_2)_{12}CH(CH_3)CH_2CH_3$ |
| 52 | 7-$O(CH_2)_{11}CH_3$ | 7-$O(CH_2)_9CH(CH_3)_2$ | 7-$O(CH_2)_8CH(CH_3)CH_2CH_3$ |
| 53 | 6-$(CH_2)_5CH_3$ | 6-$(CH_2)_3CH(CH_3)_2$ | 6-$(CH_2)_2CH(CH_3)CH_2CH_3$ |
| 54 | 6-$(CH_2)_6CH_3$ | 6-$(CH_2)_4CH(CH_3)_2$ | 6-$(CH_2)_3CH(CH_3)CH_2CH_3$ |
| 55 | 6-$(CH_2)_7CH_3$ | 6-$(CH_2)_5CH(CH_3)_2$ | 6-$(CH_2)_4CH(CH_3)CH_2CH_3$ |
| 56 | 6-$(CH_2)_8CH_3$ | 6-$(CH_2)_6CH(CH_3)_2$ | 6-$(CH_2)_5CH(CH_3)CH_2CH_3$ |
| 57 | 6-$(CH_2)_9CH_3$ | 6-$(CH_2)_7CH(CH_3)_2$ | 6-$(CH_2)_6CH(CH_3)CH_2CH_3$ |
| 58 | 6-$(CH_2)_{11}CH_3$ | 6-$(CH_2)_9CH(CH_3)_2$ | 6-$(CH_2)_8CH(CH_3)CH_2CH_3$ |
| 59 | 6-$(CH_2)_{15}CH_3$ | 6-$(CH_2)_{13}CH(CH_3)_2$ | 6-$(CH_2)_{12}CH(CH_3)CH_2CH_3$ |
| 60 | 7-$(CH_2)_{11}CH_3$ | 7-$(CH_2)_9CH(CH_3)_2$ | 7-$(CH_2)_8CH(CH_3)CH_2CH_3$ |
| | $Z = O, R^1 = H, R^3 = 2'\text{-}Cl, R^4 = 6'\text{-}Cl, R^2 =$ | | |
| 61 | H | 6-(4-Cl—Ph) | 6-$CH_2CH$=$CH(CH_2)_6CH_3$ |
| 62 | 6-Cl | 6-(4-F—Ph) | 6-$CH_2CH$=$CH(CH_2)_2CH_3$ |
| 63 | 6-F | 6-$CH_2Ph$ | 6-$OCH_2CH$=$CH(CH_2)_6CH_3$ |
| 64 | 6-Br | 6-$CH_2CH_2Ph$ | 6-$OCH_2CH$=$CH(CH_2)_2CH_3$ |
| 65 | 6-$CF_3$ | 6-$CH_2Ph$-4-F | 6-$OCH_2Ph$-4-F |
| 66 | 6-Ph | 6-$CH_2Ph$-4-Cl | 6-$OCH_2CH_2Ph$-4-F |
| 67 | 6-Py | 6-$CH_2Ph$-4-$CF_3$ | 6-$CH_2C$≡$C$—$(CH_2)_4CH_3$ |
| 68 | 6-OPh | 6-(4-$CH_3(CH_2)_4Ph$) | 6-$OCH_2C$≡$C$—$(CH_2)_4CH_3$ |
| 69 | 6-SPh | 6-$CH_2Ph$-4-$(CH_2)_9CH_3$ | 6-$CH_2CH$=$CH$—$CH_2Ph$ |

TABLE 1-continued

| | Column 1 | Column 2 | Column 3 |
|---|---|---|---|
| 70 | 6-OPy | 6-CH$_2$Ph-4-(CH$_2$)$_4$CH$_3$ | 6-OCH$_2$CH=CH—CH$_2$Ph |
| 71 | 7-Cl | 7-(4-Cl—Ph) | 7-CH$_2$CH=CH(CH$_2$)$_6$CH$_3$ |
| 72 | 7-CF$_3$ | 7-CH$_2$Ph | 7-OCH$_2$CH=CH(CH$_2$)$_6$CH$_3$ |
| 73 | 7-Ph | 7-CH$_2$CH$_2$Ph | 7-OCH$_2$CH=CH(CH$_2$)$_2$CH$_3$ |
| 74 | 7-OPh | 7-CH$_2$Ph-4-CF$_3$ | 7-CH$_2$C≡C—(CH$_2$)$_4$CH$_3$ |
| 75 | 6-O(CH$_2$)$_5$CH$_3$ | 6-O(CH$_2$)$_3$CH(CH$_3$)$_2$ | 6-O(CH$_2$)$_2$CH(CH$_3$)CH$_2$CH$_3$ |
| 76 | 6-O(CH$_2$)$_6$CH$_3$ | 6-O(CH$_2$)$_4$CH(CH$_3$)$_2$ | 6-O(CH$_2$)$_3$CH(CH$_3$)CH$_2$CH$_3$ |
| 77 | 6-O(CH$_2$)$_7$CH$_3$ | 6-O(CH$_2$)$_5$CH(CH$_3$)$_2$ | 6-O(CH$_2$)$_4$CH(CH$_3$)CH$_2$CH$_3$ |
| 78 | 6-O(CH$_2$)$_8$CH$_3$ | 6-O(CH$_2$)$_6$CH(CH$_3$)$_2$ | 6-O(CH$_2$)$_5$CH(CH$_3$)CH$_2$CH$_3$ |
| 79 | 6-O(CH$_2$)$_9$CH$_3$ | 6-O(CH$_2$)$_7$CH(CH$_3$)$_2$ | 6-O(CH$_2$)$_6$CH(CH$_3$)CH$_2$CH$_3$ |
| 80 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 81 | 6-O(CH$_2$)$_{15}$CH$_3$ | 6-O(CH$_2$)$_{13}$CH(CH$_3$)$_2$ | 6-O(CH$_2$)$_{12}$CH(CH$_3$)CH$_2$CH$_3$ |
| 82 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 83 | 6-(CH$_2$)$_5$CH$_3$ | 6-(CH$_2$)$_3$CH(CH$_3$)$_2$ | 6-(CH$_2$)$_2$CH(CH$_3$)CH$_2$CH$_3$ |
| 84 | 6-(CH$_2$)$_6$CH$_3$ | 6-(CH$_2$)$_4$CH(CH$_3$)$_2$ | 6-(CH$_2$)$_3$CH(CH$_3$)CH$_2$CH$_3$ |
| 85 | 6-(CH$_2$)$_7$CH$_3$ | 6-(CH$_2$)$_5$CH(CH$_3$)$_2$ | 6-(CH$_2$)$_4$CH(CH$_3$)CH$_2$CH$_3$ |
| 86 | 6-(CH$_2$)$_8$CH$_3$ | 6-(CH$_2$)$_6$CH(CH$_3$)$_2$ | 6-(CH$_2$)$_5$CH(CH$_3$)CH$_2$CH$_3$ |
| 87 | 6-(CH$_2$)$_9$CH$_3$ | 6-(CH$_2$)$_7$CH(CH$_3$)$_2$ | 6-(CH$_2$)$_6$CH(CH$_3$)CH$_2$CH$_3$ |
| 88 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| 89 | 6-(CH$_2$)$_{15}$CH$_3$ | 6-(CH$_2$)$_{13}$CH(CH$_3$)$_2$ | 6-(CH$_2$)$_{12}$CH(CH$_3$)CH$_2$CH$_3$ |
| 90 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |
| | Z = S, R$^1$ = H, R$^3$ = 2'-F, R$^4$ = 6'-F, R$^2$ = | | |
| 91 | H | 6-(4-Cl—Ph) | 6-CH$_2$CH=CH(CH$_2$)$_6$CH$_3$ |
| 92 | 6-Cl | 6-(4-F—Ph) | 6-CH$_2$CH=CH(CH$_2$)$_2$CH$_3$ |
| 93 | 6-F | 6-CH$_2$Ph | 6-OCH$_2$CH=CH(CH$_2$)$_6$CH$_3$ |
| 94 | 6-Br | 6-CH$_2$CH$_2$Ph | 6-OCH$_2$CH=CH(CH$_2$)$_2$CH$_3$ |
| 95 | 6-CF$_3$ | 6-CH$_2$Ph-4-F | 6-OCH$_2$Ph-4-F |
| 96 | 6-Ph | 6-CH$_2$Ph-4-Cl | 6-OCH$_2$CH$_2$Ph-4-F |
| 97 | 6-Py | 6-CH$_2$Ph-4-CF$_3$ | 6-CH$_2$C≡C—(CH$_2$)$_4$CH$_3$ |
| 98 | 6-OPh | 6-(4-CH$_3$(CH$_2$)$_4$Ph) | 6-OCH$_2$C≡C—(CH$_2$)$_4$CH$_3$ |
| 99 | 6-SPh | 6-CH$_2$Ph-4-(CH$_2$)$_9$CH$_3$ | 6-CH$_2$CH=CH—CH$_2$Ph |
| 100 | 6-OPy | 6-CH$_2$Ph-4-(CH$_2$)$_4$CH$_3$ | 6-OCH$_2$CH=CH—CH$_2$Ph |
| 101 | 7-Cl | 7-(4-Cl—Ph) | 7-CH$_2$CH=CH(CH$_2$)$_6$CH$_3$ |
| 102 | 7-CF$_3$ | 7-CH$_2$Ph | 7-OCH$_2$CH=CH(CH$_2$)$_6$CH$_3$ |
| 103 | 7-Ph | 7-CH$_2$CH$_2$Ph | 7-OCH$_2$CH=CH(CH$_2$)$_2$CH$_3$ |
| 104 | 7-OPh | 7-CH$_2$Ph-4-CF$_3$ | 7-CH$_2$C≡C—(CH$_2$)$_4$CH$_3$ |
| 105 | 6-O(CH$_2$)$_5$CH$_3$ | 6-O(CH$_2$)$_3$CH(CH$_3$)$_2$ | 6-O(CH$_2$)$_2$CH(CH$_3$)CH$_2$CH$_3$ |
| 106 | 6-O(CH$_2$)$_6$CH$_3$ | 6-O(CH$_2$)$_4$CH(CH$_3$)$_2$ | 6-O(CH$_2$)$_3$CH(CH$_3$)CH$_2$CH$_3$ |
| 107 | 6-O(CH$_2$)$_7$CH$_3$ | 6-O(CH$_2$)$_5$CH(CH$_3$)$_2$ | 6-O(CH$_2$)$_4$CH(CH$_3$)CH$_2$CH$_3$ |
| 108 | 6-O(CH$_2$)$_8$CH$_3$ | 6-O(CH$_2$)$_6$CH(CH$_3$)$_2$ | 6-O(CH$_2$)$_5$CH(CH$_3$)CH$_2$CH$_3$ |
| 109 | 6-O(CH$_2$)$_9$CH$_3$ | 6-O(CH$_2$)$_7$CH(CH$_3$)$_2$ | 6-O(CH$_2$)$_6$CH(CH$_3$)CH$_2$CH$_3$ |
| 110 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 111 | 6-O(CH$_2$)$_{15}$CH$_3$ | 6-O(CH$_2$)$_{13}$CH(CH$_3$)$_2$ | 6-O(CH$_2$)$_{12}$CH(CH$_3$)CH$_2$CH$_3$ |
| 112 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 113 | 6-(CH$_2$)$_5$CH$_3$ | 6-(CH$_2$)$_3$CH(CH$_3$)$_2$ | 6-(CH$_2$)$_2$CH(CH$_3$)CH$_2$CH$_3$ |
| 114 | 6-(CH$_2$)$_6$CH$_3$ | 6-(CH$_2$)$_4$CH(CH$_3$)$_2$ | 6-(CH$_2$)$_3$CH(CH$_3$)CH$_2$CH$_3$ |
| 115 | 6-(CH$_2$)$_7$CH$_3$ | 6-(CH$_2$)$_5$CH(CH$_3$)$_2$ | 6-(CH$_2$)$_4$CH(CH$_3$)CH$_2$CH$_3$ |
| 116 | 6-(CH$_2$)$_8$CH$_3$ | 6-(CH$_2$)$_6$CH(CH$_3$)$_2$ | 6-(CH$_2$)$_5$CH(CH$_3$)CH$_2$CH$_3$ |
| 117 | 6-(CH$_2$)$_9$CH$_3$ | 6-(CH$_2$)$_7$CH(CH$_3$)$_2$ | 6-(CH$_2$)$_6$CH(CH$_3$)CH$_2$CH$_3$ |
| 118 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| 119 | 6-(CH$_2$)$_{15}$CH$_3$ | 6-(CH$_2$)$_{13}$CH(CH$_3$)$_2$ | 6-(CH$_2$)$_{12}$CH(CH$_3$)CH$_2$CH$_3$ |
| 120 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |
| | Z = S, R$^1$ = H, R$^3$ = 2'-F, R$^4$ = 6'-Cl, R$^2$ = | | |
| 121 | H | 6-(4-Cl—Ph) | 6-CH$_2$CH=CH(CH$_2$)$_6$CH$_3$ |
| 122 | 6-Cl | 6-(4-F—Ph) | 6-CH$_2$CH=CH(CH$_2$)$_2$CH$_3$ |
| 123 | 6-F | 6-CH$_2$Ph | 6-OCH$_2$CH=CH(CH$_2$)$_6$CH$_3$ |
| 124 | 6-Br | 6-CH$_2$CH$_2$Ph | 6-OCH$_2$CH=CH(CH$_2$)$_2$CH$_3$ |
| 125 | 6-CF$_3$ | 6-CH$_2$Ph-4-F | 6-OCH$_2$Ph-4-F |
| 126 | 6-Ph | 6-CH$_2$Ph-4-Cl | 6-OCH$_2$CH$_2$Ph-4-F |
| 127 | 6-Py | 6-CH$_2$Ph-4-CF$_3$ | 6-CH$_2$C≡C—(CH$_2$)$_4$CH$_3$ |
| 128 | 6-OPh | 6-(4-CH$_3$(CH$_2$)$_4$Ph) | 6-OCH$_2$C≡C—(CH$_2$)$_4$CH$_3$ |
| 129 | 6-SPh | 6-CH$_2$Ph-4-(CH$_2$)$_9$CH$_3$ | 6-CH$_2$CH=CH—CH$_2$Ph |
| 130 | 6-OPy | 6-CH$_2$Ph-4-(CH$_2$)$_4$CH$_3$ | 6-OCH$_2$CH=CH—CH$_2$Ph |
| 131 | 7-Cl | 7-(4-Cl—Ph) | 7-CH$_2$CH=CH(CH$_2$)$_6$CH$_3$ |
| 132 | 7-CF$_3$ | 7-CH$_2$Ph | 7-OCH$_2$CH=CH(CH$_2$)$_6$CH$_3$ |
| 133 | 7-Ph | 7-CH$_2$CH$_2$Ph | 7-OCH$_2$CH=CH(CH$_2$)$_2$CH$_3$ |
| 134 | 7-OPh | 7-CH$_2$Ph-4-CF$_3$ | 7-CH$_2$C≡C—(CH$_2$)$_4$CH$_3$ |
| 135 | 6-O(CH$_2$)$_5$CH$_3$ | 6-O(CH$_2$)$_3$CH(CH$_3$)$_2$ | 6-O(CH$_2$)$_2$CH(CH$_3$)CH$_2$CH$_3$ |
| 136 | 6-O(CH$_2$)$_6$CH$_3$ | 6-O(CH$_2$)$_4$CH(CH$_3$)$_2$ | 6-O(CH$_2$)$_3$CH(CH$_3$)CH$_2$CH$_3$ |
| 137 | 6-O(CH$_2$)$_7$CH$_3$ | 6-O(CH$_2$)$_5$CH(CH$_3$)$_2$ | 6-O(CH$_2$)$_4$CH(CH$_3$)CH$_2$CH$_3$ |
| 138 | 6-O(CH$_2$)$_8$CH$_3$ | 6-O(CH$_2$)$_6$CH(CH$_3$)$_2$ | 6-O(CH$_2$)$_5$CH(CH$_3$)CH$_2$CH$_3$ |
| 139 | 6-O(CH$_2$)$_9$CH$_3$ | 6-O(CH$_2$)$_7$CH(CH$_3$)$_2$ | 6-O(CH$_2$)$_6$CH(CH$_3$)CH$_2$CH$_3$ |
| 140 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 141 | 6-O(CH$_2$)$_{15}$CH$_3$ | 6-O(CH$_2$)$_{13}$CH(CH$_3$)$_2$ | 6-O(CH$_2$)$_{12}$CH(CH$_3$)CH$_2$CH$_3$ |
| 142 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 143 | 6-(CH$_2$)$_5$CH$_3$ | 6-(CH$_2$)$_3$CH(CH$_3$)$_2$ | 6-(CH$_2$)$_2$CH(CH$_3$)CH$_2$CH$_3$ |
| 144 | 6-(CH$_2$)$_6$CH$_3$ | 6-(CH$_2$)$_4$CH(CH$_3$)$_2$ | 6-(CH$_2$)$_3$CH(CH$_3$)CH$_2$CH$_3$ |
| 145 | 6-(CH$_2$)$_7$CH$_3$ | 6-(CH$_2$)$_5$CH(CH$_3$)$_2$ | 6-(CH$_2$)$_4$CH(CH$_3$)CH$_2$CH$_3$ |
| 146 | 6-(CH$_2$)$_8$CH$_3$ | 6-(CH$_2$)$_6$CH(CH$_3$)$_2$ | 6-(CH$_2$)$_5$CH(CH$_3$)CH$_2$CH$_3$ |
| 147 | 6-(CH$_2$)$_9$CH$_3$ | 6-(CH$_2$)$_7$CH(CH$_3$)$_2$ | 6-(CH$_2$)$_6$CH(CH$_3$)CH$_2$CH$_3$ |

TABLE 1-continued

|     | Column 1 | Column 2 | Column 3 |
| --- | --- | --- | --- |
| 148 | 6-$(CH_2)_{11}CH_3$ | 6-$(CH_2)_9CH(CH_3)_2$ | 6-$(CH_2)_8CH(CH_3)CH_2CH_3$ |
| 149 | 6-$(CH_2)_{15}CH_3$ | 6-$(CH_2)_{13}CH(CH_3)_2$ | 6-$(CH_2)_{12}CH(CH_3)CH_2CH_3$ |
| 150 | 7-$(CH_2)_{11}CH_3$ | 7-$(CH_2)_9CH(CH_3)_2$ | 7-$(CH_2)_8CH(CH_3)CH_2CH_3$ |
| | $Z = O, R^1 = 8\text{-}Cl, R^3 = 2'\text{-}F, R^4 = 6'\text{-}F, R^2 =$ | | |
| 151 | H | 6-(4-Cl—Ph) | 6-$CH_2CH=CH(CH_2)_6CH_3$ |
| 152 | 6-Cl | 6-(4-F—Ph) | 6-$CH_2CH=CH(CH_2)_2CH_3$ |
| 153 | 6-F | 6-$CH_2Ph$ | 6-$OCH_2CH=CH(CH_2)_6CH_3$ |
| 154 | 6-Br | 6-$CH_2CH_2Ph$ | 6-$OCH_2CH=CH(CH_2)_2CH_3$ |
| 155 | 6-$CF_3$ | 6-$CH_2Ph$-4-F | 6-$OCH_2Ph$-4-F |
| 156 | 6-Ph | 6-$CH_2Ph$-4-Cl | 6-$OCH_2CH_2Ph$-4-F |
| 157 | 6-Py | 6-$CH_2Ph$-4-$CF_3$ | 6-$CH_2C{\equiv}C$—$(CH_2)_4CH_3$ |
| 158 | 6-OPh | 6-(4-$CH_3(CH_2)_4Ph$) | 6-$OCH_2C{\equiv}C$—$(CH_2)_4CH_3$ |
| 159 | 6-SPh | 6-$CH_2Ph$-4-$(CH_2)_9CH_3$ | 6-$CH_2CH=CH$—$CH_2Ph$ |
| 160 | 6-OPy | 6-$CH_2Ph$-4-$(CH_2)_4CH_3$ | 6-$OCH_2CH=CH$—$CH_2Ph$ |
| 161 | 7-Cl | 7-(4-Cl—Ph) | 7-$CH_2CH=CH(CH_2)_6CH_3$ |
| 162 | 7-$CF_3$ | 7-$CH_2Ph$ | 7-$OCH_2CH=CH(CH_2)_6CH_3$ |
| 163 | 7-Ph | 7-$CH_2CH_2Ph$ | 7-$OCH_2CH=CH(CH_2)_2CH_3$ |
| 164 | 7-OPh | 7-$CH_2Ph$-4-$CF_3$ | 7-$CH_2C{\equiv}C$—$(CH_2)_4CH_3$ |
| 165 | 6-$O(CH_2)_5CH_3$ | 6-$O(CH_2)_3CH(CH_3)_2$ | 6-$O(CH_2)_2CH(CH_3)CH_2CH_3$ |
| 166 | 6-$O(CH_2)_6CH_3$ | 6-$O(CH_2)_4CH(CH_3)_2$ | 6-$O(CH_2)_3CH(CH_3)CH_2CH_3$ |
| 167 | 6-$O(CH_2)_7CH_3$ | 6-$O(CH_2)_5CH(CH_3)_2$ | 6-$O(CH_2)_4CH(CH_3)CH_2CH_3$ |
| 168 | 6-$O(CH_2)_8CH_3$ | 6-$O(CH_2)_6CH(CH_3)_2$ | 6-$O(CH_2)_5CH(CH_3)CH_2CH_3$ |
| 169 | 6-$O(CH_2)_9CH_3$ | 6-$O(CH_2)_7CH(CH_3)_2$ | 6-$O(CH_2)_6CH(CH_3)CH_2CH_3$ |
| 170 | 6-$O(CH_2)_{11}CH_3$ | 6-$O(CH_2)_9CH(CH_3)_2$ | 6-$O(CH_2)_8CH(CH_3)CH_2CH_3$ |
| 171 | 6-$O(CH_2)_{15}CH_3$ | 6-$O(CH_2)_{13}CH(CH_3)_2$ | 6-$O(CH_2)_{12}CH(CH_3)CH_2CH_3$ |
| 172 | 7-$O(CH_2)_{11}CH_3$ | 7-$O(CH_2)_9CH(CH_3)_2$ | 7-$O(CH_2)_8CH(CH_3)CH_2CH_3$ |
| 173 | 6-$(CH_2)_5CH_3$ | 6-$(CH_2)_3CH(CH_3)_2$ | 6-$(CH_2)_2CH(CH_3)CH_2CH_3$ |
| 174 | 6-$(CH_2)_6CH_3$ | 6-$(CH_2)_4CH(CH_3)_2$ | 6-$(CH_2)_3CH(CH_3)CH_2CH_3$ |
| 175 | 6-$(CH_2)_7CH_3$ | 6-$(CH_2)_5CH(CH_3)_2$ | 6-$(CH_2)_4CH(CH_3)CH_2CH_3$ |
| 176 | 6-$(CH_2)_8CH_3$ | 6-$(CH_2)_6CH(CH_3)_2$ | 6-$(CH_2)_5CH(CH_3)CH_2CH_3$ |
| 177 | 6-$(CH_2)_9CH_3$ | 6-$(CH_2)_7CH(CH_3)_2$ | 6-$(CH_2)_6CH(CH_3)CH_2CH_3$ |
| 178 | 6-$(CH_2)_{11}CH_3$ | 6-$(CH_2)_9CH(CH_3)_2$ | 6-$(CH_2)_8CH(CH_3)CH_2CH_3$ |
| 179 | 6-$(CH_2)_{15}CH_3$ | 6-$(CH_2)_{13}CH(CH_3)_2$ | 6-$(CH_2)_{12}CH(CH_3)CH_2CH_3$ |
| 180 | 7-$(CH_2)_{11}CH_3$ | 7-$(CH_2)_9CH(CH_3)_2$ | 7-$(CH_2)_8CH(CH_3)CH_2CH_3$ |
| | $Z = O, R^1 = 8\text{-}Cl, R^3 = 2'\text{-}F, R^4 = 6'\text{-}F, R^2 =$ | | |
| 181 | H | 6-(4-Cl—Ph) | 6-$CH_2CH=CH(CH_2)_6CH_3$ |
| 182 | 6-Cl | 6-(4-F—Ph) | 6-$CH_2CH=CH(CH_2)_2CH_3$ |
| 183 | 6-F | 6-$CH_2Ph$ | 6-$OCH_2CH=CH(CH_2)_6CH_3$ |
| 184 | 6-Br | 6-$CH_2CH_2Ph$ | 6-$OCH_2CH=CH(CH_2)_2CH_3$ |
| 185 | 6-$CF_3$ | 6-$CH_2Ph$-4-F | 6-$OCH_2Ph$-4-F |
| 186 | 6-Ph | 6-$CH_2Ph$-4-Cl | 6-$OCH_2CH_2Ph$-4-F |
| 187 | 6-Py | 6-$CH_2Ph$-4-$CF_3$ | 6-$CH_2C{\equiv}C$—$(CH_2)_4CH_3$ |
| 188 | 6-OPh | 6-(4-$CH_3(CH_2)_4Ph$) | 6-$OCH_2C{\equiv}C$—$(CH_2)_4CH_3$ |
| 189 | 6-SPh | 6-$CH_2Ph$-4-$(CH_2)_9CH_3$ | 6-$CH_2CH=CH$—$CH_2Ph$ |
| 190 | 6-OPy | 6-$CH_2Ph$-4-$(CH_2)_4CH_3$ | 6-$OCH_2CH=CH$—$CH_2Ph$ |
| 191 | 7-Cl | 7-(4-Cl—Ph) | 7-$CH_2CH=CH(CH_2)_6CH_3$ |
| 192 | 7-$CF_3$ | 7-$CH_2Ph$ | 7-$OCH_2CH=CH(CH_2)_6CH_3$ |
| 193 | 7-Ph | 7-$CH_2CH_2Ph$ | 7-$OCH_2CH=CH(CH_2)_2CH_3$ |
| 194 | 7-OPh | 7-$CH_2Ph$-4-$CF_3$ | 7-$CH_2C{\equiv}C$—$(CH_2)_4CH_3$ |
| 195 | 6-$O(CH_2)_5CH_3$ | 6-$O(CH_2)_3CH(CH_3)_2$ | 6-$O(CH_2)_2CH(CH_3)CH_2CH_3$ |
| 196 | 6-$O(CH_2)_6CH_3$ | 6-$O(CH_2)_4CH(CH_3)_2$ | 6-$O(CH_2)_3CH(CH_3)CH_2CH_3$ |
| 197 | 6-$O(CH_2)_7CH_3$ | 6-$O(CH_2)_5CH(CH_3)_2$ | 6-$O(CH_2)_4CH(CH_3)CH_2CH_3$ |
| 198 | 6-$O(CH_2)_8CH_3$ | 6-$O(CH_2)_6CH(CH_3)_2$ | 6-$O(CH_2)_5CH(CH_3)CH_2CH_3$ |
| 199 | 6-$O(CH_2)_9CH_3$ | 6-$O(CH_2)_7CH(CH_3)_2$ | 6-$O(CH_2)_6CH(CH_3)CH_2CH_3$ |
| 200 | 6-$O(CH_2)_{11}CH_3$ | 6-$O(CH_2)_9CH(CH_3)_2$ | 6-$O(CH_2)_8CH(CH_3)CH_2CH_3$ |
| 201 | 6-$O(CH_2)_{15}CH_3$ | 6-$O(CH_2)_{13}CH(CH_3)_2$ | 6-$O(CH_2)_{12}CH(CH_3)CH_2CH_3$ |
| 202 | 7-$O(CH_2)_{11}CH_3$ | 7-$O(CH_2)_9CH(CH_3)_2$ | 7-$O(CH_2)_8CH(CH_3)CH_2CH_3$ |
| 203 | 6-$(CH_2)_5CH_3$ | 6-$(CH_2)_3CH(CH_3)_2$ | 6-$(CH_2)_2CH(CH_3)CH_2CH_3$ |
| 204 | 6-$(CH_2)_6CH_3$ | 6-$(CH_2)_4CH(CH_3)_2$ | 6-$(CH_2)_3CH(CH_3)CH_2CH_3$ |
| 205 | 6-$(CH_2)_7CH_3$ | 6-$(CH_2)_5CH(CH_3)_2$ | 6-$(CH_2)_4CH(CH_3)CH_2CH_3$ |
| 206 | 6-$(CH_2)_8CH_3$ | 6-$(CH_2)_6CH(CH_3)_2$ | 6-$(CH_2)_5CH(CH_3)CH_2CH_3$ |
| 207 | 6-$(CH_2)_9CH_3$ | 6-$(CH_2)_7CH(CH_3)_2$ | 6-$(CH_2)_6CH(CH_3)CH_2CH_3$ |
| 208 | 6-$(CH_2)_{11}CH_3$ | 6-$(CH_2)_9CH(CH_3)_2$ | 6-$(CH_2)_8CH(CH_3)CH_2CH_3$ |
| 209 | 6-$(CH_2)_{15}CH_3$ | 6-$(CH_2)_{13}CH(CH_3)_2$ | 6-$(CH_2)_{12}CH(CH_3)CH_2CH_3$ |
| 210 | 7-$(CH_2)_{11}CH_3$ | 7-$(CH_2)_9CH(CH_3)_2$ | 7-$(CH_2)_8CH(CH_3)CH_2CH_3$ |
| | $Z = O, R^1 = 8\text{-}F, R^3 = 2'\text{-}F, R^4 = 6'\text{-}F, R^2 =$ | | |
| 211 | H | 6-(4-Cl—Ph) | 6-$CH_2CH=CH(CH_2)_6CH_3$ |
| 212 | 6-Cl | 6-(4-F—Ph) | 6-$CH_2CH=CH(CH_2)_2CH_3$ |
| 213 | 6-F | 6-$CH_2Ph$ | 6-$OCH_2CH=CH(CH_2)_6CH_3$ |
| 214 | 6-Br | 6-$CH_2CH_2Ph$ | 6-$OCH_2CH=CH(CH_2)_2CH_3$ |
| 215 | 6-$CF_3$ | 6-$CH_2Ph$-4-F | 6-$OCH_2Ph$-4-F |
| 216 | 6-Ph | 6-$CH_2Ph$-4-Cl | 6-$OCH_2CH_2Ph$-4-F |
| 217 | 6-Py | 6-$CH_2Ph$-4-$CF_3$ | 6-$CH_2C{\equiv}C$—$(CH_2)_4CH_3$ |
| 218 | 6-OPh | 6-(4-$CH_3(CH_2)_4Ph$) | 6-$OCH_2C{\equiv}C$—$(CH_2)_4CH_3$ |
| 219 | 6-SPh | 6-$CH_2Ph$-4-$(CH_2)_9CH_3$ | 6-$CH_2CH=CH$—$CH_2Ph$ |
| 220 | 6-OPy | 6-$CH_2Ph$-4-$(CH_2)_4CH_3$ | 6-$OCH_2CH=CH$—$CH_2Ph$ |
| 221 | 7-Cl | 7-(4-Cl—Ph) | 7-$CH_2CH=CH(CH_2)_6CH_3$ |
| 222 | 7-$CF_3$ | 7-$CH_2Ph$ | 7-$OCH_2CH=CH(CH_2)_6CH_3$ |
| 223 | 7-Ph | 7-$CH_2CH_2Ph$ | 7-$OCH_2CH=CH(CH_2)_2CH_3$ |
| 224 | 7-OPh | 7-$CH_2Ph$-4-$CF_3$ | 7-$CH_2C{\equiv}C$—$(CH_2)_4CH_3$ |

TABLE 1-continued

| | Column 1 | Column 2 | Column 3 |
|---|---|---|---|
| 225 | 6-O(CH$_2$)$_5$CH$_3$ | 6-O(CH$_2$)$_3$CH(CH$_3$)$_2$ | 6-O(CH$_2$)$_2$CH(CH$_3$)CH$_2$CH$_3$ |
| 226 | 6-O(CH$_2$)$_6$CH$_3$ | 6-O(CH$_2$)$_4$CH(CH$_3$)$_2$ | 6-O(CH$_2$)$_3$CH(CH$_3$)CH$_2$CH$_3$ |
| 227 | 6-O(CH$_2$)$_7$CH$_3$ | 6-O(CH$_2$)$_5$CH(CH$_3$)$_2$ | 6-O(CH$_2$)$_4$CH(CH$_3$)CH$_2$CH$_3$ |
| 228 | 6-O(CH$_2$)$_8$CH$_3$ | 6-O(CH$_2$)$_6$CH(CH$_3$)$_2$ | 6-O(CH$_2$)$_5$CH(CH$_3$)CH$_2$CH$_3$ |
| 229 | 6-O(CH$_2$)$_9$CH$_3$ | 6-O(CH$_2$)$_7$CH(CH$_3$)$_2$ | 6-O(CH$_2$)$_6$CH(CH$_3$)CH$_2$CH$_3$ |
| 230 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 231 | 6-O(CH$_2$)$_{15}$CH$_3$ | 6-O(CH$_2$)$_{13}$CH(CH$_3$)$_2$ | 6-O(CH$_2$)$_{12}$CH(CH$_3$)CH$_2$CH$_3$ |
| 232 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 233 | 6-(CH$_2$)$_5$CH$_3$ | 6-(CH$_2$)$_3$CH(CH$_3$)$_2$ | 6-(CH$_2$)$_2$CH(CH$_3$)CH$_2$CH$_3$ |
| 234 | 6-(CH$_2$)$_6$CH$_3$ | 6-(CH$_2$)$_4$CH(CH$_3$)$_2$ | 6-(CH$_2$)$_3$CH(CH$_3$)CH$_2$CH$_3$ |
| 235 | 6-(CH$_2$)$_7$CH$_3$ | 6-(CH$_2$)$_5$CH(CH$_3$)$_2$ | 6-(CH$_2$)$_4$CH(CH$_3$)CH$_2$CH$_3$ |
| 236 | 6-(CH$_2$)$_8$CH$_3$ | 6-(CH$_2$)$_6$CH(CH$_3$)$_2$ | 6-(CH$_2$)$_5$CH(CH$_3$)CH$_2$CH$_3$ |
| 237 | 6-(CH$_2$)$_9$CH$_3$ | 6-(CH$_2$)$_7$CH(CH$_3$)$_2$ | 6-(CH$_2$)$_6$CH(CH$_3$)CH$_2$CH$_3$ |
| 238 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| 239 | 6-(CH$_2$)$_{15}$CH$_3$ | 6-(CH$_2$)$_{13}$CH(CH$_3$)$_2$ | 6-(CH$_2$)$_{12}$CH(CH$_3$)CH$_2$CH$_3$ |
| 240 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |
| | Z = O, R$^1$ = 8-F, R$^3$ = 2'-F, R$^4$ = 6'-Cl, R$^2$ = | | |
| 241 | H | 6-(4-Cl—Ph) | 6-CH$_2$CH=CH(CH$_2$)$_6$CH$_3$ |
| 242 | 6-Cl | 6-(4-F—Ph) | 6-CH$_2$CH=CH(CH$_2$)$_2$CH$_3$ |
| 243 | 6-F | 6-CH$_2$Ph | 6-OCH$_2$CH=CH(CH$_2$)$_6$CH$_3$ |
| 244 | 6-Br | 6-CH$_2$CH$_2$Ph | 6-OCH$_2$CH=CH(CH$_2$)$_2$CH$_3$ |
| 245 | 6-CF$_3$ | 6-CH$_2$Ph-4-F | 6-OCH$_2$Ph-4-F |
| 246 | 6-Ph | 6-CH$_2$Ph-4-Cl | 6-OCH$_2$CH$_2$Ph-4-F |
| 247 | 6-Py | 6-CH$_2$Ph-4-CF$_3$ | 6-CH$_2$C≡C—(CH$_2$)$_4$CH$_3$ |
| 248 | 6-OPh | 6-(4-CH$_3$(CH$_2$)$_4$Ph) | 6-OCH$_2$C≡C—(CH$_2$)$_4$CH$_3$ |
| 249 | 6-SPh | 6-CH$_2$Ph-4-(CH$_2$)$_9$CH$_3$ | 6-CH$_2$CH=CH—CH$_2$Ph |
| 250 | 6-OPy | 6-CH$_2$Ph-4-(CH$_2$)$_4$CH$_3$ | 6-OCH$_2$CH=CH—CH$_2$Ph |
| 251 | 7-Cl | 7-(4-Cl—Ph) | 7-CH$_2$CH=CH(CH$_2$)$_6$CH$_3$ |
| 252 | 7-CF$_3$ | 7-CH$_2$Ph | 7-OCH$_2$CH=CH(CH$_2$)$_6$CH$_3$ |
| 253 | 7-Ph | 7-CH$_2$CH$_2$Ph | 7-OCH$_2$CH=CH(CH$_2$)$_2$CH$_3$ |
| 254 | 7-OPh | 7-CH$_2$Ph-4-CF$_3$ | 7-CH$_2$C≡C—(CH$_2$)$_4$CH$_3$ |
| 255 | 6-O(CH$_2$)$_5$CH$_3$ | 6-O(CH$_2$)$_3$CH(CH$_3$)$_2$ | 6-O(CH$_2$)$_2$CH(CH$_3$)CH$_2$CH$_3$ |
| 256 | 6-O(CH$_2$)$_6$CH$_3$ | 6-O(CH$_2$)$_4$CH(CH$_3$)$_2$ | 6-O(CH$_2$)$_3$CH(CH$_3$)CH$_2$CH$_3$ |
| 257 | 6-O(CH$_2$)$_7$CH$_3$ | 6-O(CH$_2$)$_5$CH(CH$_3$)$_2$ | 6-O(CH$_2$)$_4$CH(CH$_3$)CH$_2$CH$_3$ |
| 258 | 6-O(CH$_2$)$_8$CH$_3$ | 6-O(CH$_2$)$_6$CH(CH$_3$)$_2$ | 6-O(CH$_2$)$_5$CH(CH$_3$)CH$_2$CH$_3$ |
| 259 | 6-O(CH$_2$)$_9$CH$_3$ | 6-O(CH$_2$)$_7$CH(CH$_3$)$_2$ | 6-O(CH$_2$)$_6$CH(CH$_3$)CH$_2$CH$_3$ |
| 260 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 261 | 6-O(CH$_2$)$_{15}$CH$_3$ | 6-O(CH$_2$)$_{13}$CH(CH$_3$)$_2$ | 6-O(CH$_2$)$_{12}$CH(CH$_3$)CH$_2$CH$_3$ |
| 262 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 263 | 6-(CH$_2$)$_5$CH$_3$ | 6-(CH$_2$)$_3$CH(CH$_3$)$_2$ | 6-(CH$_2$)$_2$CH(CH$_3$)CH$_2$CH$_3$ |
| 264 | 6-(CH$_2$)$_6$CH$_3$ | 6-(CH$_2$)$_4$CH(CH$_3$)$_2$ | 6-(CH$_2$)$_3$CH(CH$_3$)CH$_2$CH$_3$ |
| 265 | 6-(CH$_2$)$_7$CH$_3$ | 6-(CH$_2$)$_5$CH(CH$_3$)$_2$ | 6-(CH$_2$)$_4$CH(CH$_3$)CH$_2$CH$_3$ |
| 266 | 6-(CH$_2$)$_8$CH$_3$ | 6-(CH$_2$)$_6$CH(CH$_3$)$_2$ | 6-(CH$_2$)$_5$CH(CH$_3$)CH$_2$CH$_3$ |
| 267 | 6-(CH$_2$)$_9$CH$_3$ | 6-(CH$_2$)$_7$CH(CH$_3$)$_2$ | 6-(CH$_2$)$_6$CH(CH$_3$)CH$_2$CH$_3$ |
| 268 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| 269 | 6-(CH$_2$)$_{15}$CH$_3$ | 6-(CH$_2$)$_{13}$CH(CH$_3$)$_2$ | 6-(CH$_2$)$_{12}$CH(CH$_3$)CH$_2$CH$_3$ |
| 270 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |

TABLE 2

| | Column 1 | Column 2 | Column 3 |
|---|---|---|---|
| | Z = O, R$^1$ = H, R$^3$ = 2'-F, R$^4$ = 6'-F, R$^2$ = | | |
| 1 | H | 6-(4-Cl—Ph) | 6-CH$_2$CH=CH(CH$_2$)$_6$CH$_3$ |
| 2 | 6-Cl | 6-(4-F—Ph) | 6-CH$_2$CH=CH(CH$_2$)$_2$CH$_3$ |
| 3 | 6-F | 6-CH$_2$Ph | 6-OCH$_2$CH=CH(CH$_2$)$_6$CH$_3$ |
| 4 | 6-Br | 6-CH$_2$CH$_2$Ph | 6-OCH$_2$CH=CH(CH$_2$)$_2$CH$_3$ |
| 5 | 6-CF$_3$ | 6-CH$_2$Ph-4-F | 6-OCH$_2$Ph-4-F |
| 6 | 6-Ph | 6-CH$_2$Ph-4-Cl | 6-OCH$_2$CH$_2$Ph-4-F |
| 7 | 6-Py | 6-CH$_2$Ph-4-CF$_3$ | 6-CH$_2$C≡C—(CH$_2$)$_4$CH$_3$ |
| 8 | 6-OPh | 6-(4-CH$_3$(CH$_2$)$_4$Ph) | 6-OCH$_2$C≡C—(CH$_2$)$_4$CH$_3$ |
| 9 | 6-SPh | 6-CH$_2$Ph-4-(CH$_2$)$_9$CH$_3$ | 6-CH$_2$CH=CH—CH$_2$Ph |
| 10 | 6-OPy | 6-CH$_2$Ph-4-(CH$_2$)$_4$CH$_3$ | 6-OCH$_2$CH=CH—CH$_2$Ph |
| 11 | 7-Cl | 7-(4-Cl—Ph) | 7-CH$_2$CH=CH(CH$_2$)$_6$CH$_3$ |
| 12 | 7-CF$_3$ | 7-CH$_2$Ph | 7-OCH$_2$CH=CH(CH$_2$)$_6$CH$_3$ |
| 13 | 7-Ph | 7-CH$_2$CH$_2$Ph | 7-OCH$_2$CH=CH(CH$_2$)$_2$CH$_3$ |
| 14 | 7-OPh | 7-CH$_2$Ph-4-CF$_3$ | 7-CH$_2$C≡C—(CH$_2$)$_4$CH$_3$ |
| 15 | 6-O(CH$_2$)$_5$CH$_3$ | 6-O(CH$_2$)$_3$CH(CH$_3$)$_2$ | 6-O(CH$_2$)$_2$CH(CH$_3$)CH$_2$CH$_3$ |
| 16 | 6-O(CH$_2$)$_6$CH$_3$ | 6-O(CH$_2$)$_4$CH(CH$_3$)$_2$ | 6-O(CH$_2$)$_3$CH(CH$_3$)CH$_2$CH$_3$ |
| 17 | 6-O(CH$_2$)$_7$CH$_3$ | 6-O(CH$_2$)$_5$CH(CH$_3$)$_2$ | 6-O(CH$_2$)$_4$CH(CH$_3$)CH$_2$CH$_3$ |
| 18 | 6-O(CH$_2$)$_8$CH$_3$ | 6-O(CH$_2$)$_6$CH(CH$_3$)$_2$ | 6-O(CH$_2$)$_5$CH(CH$_3$)CH$_2$CH$_3$ |
| 19 | 6-O(CH$_2$)$_9$CH$_3$ | 6-O(CH$_2$)$_7$CH(CH$_3$)$_2$ | 6-O(CH$_2$)$_6$CH(CH$_3$)CH$_2$CH$_3$ |
| 20 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 21 | 6-O(CH$_2$)$_{15}$CH$_3$ | 6-O(CH$_2$)$_{13}$CH(CH$_3$)$_2$ | 6-O(CH$_2$)$_{12}$CH(CH$_3$)CH$_2$CH$_3$ |
| 22 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 23 | 6-(CH$_2$)$_5$CH$_3$ | 6-(CH$_2$)$_3$CH(CH$_3$)$_2$ | 6-(CH$_2$)$_2$CH(CH$_3$)CH$_2$CH$_3$ |
| 24 | 6-(CH$_2$)$_6$CH$_3$ | 6-(CH$_2$)$_4$CH(CH$_3$)$_2$ | 6-(CH$_2$)$_3$CH(CH$_3$)CH$_2$CH$_3$ |
| 25 | 6-(CH$_2$)$_7$CH$_3$ | 6-(CH$_2$)$_5$CH(CH$_3$)$_2$ | 6-(CH$_2$)$_4$CH(CH$_3$)CH$_2$CH$_3$ |
| 26 | 6-(CH$_2$)$_8$CH$_3$ | 6-(CH$_2$)$_6$CH(CH$_3$)$_2$ | 6-(CH$_2$)$_5$CH(CH$_3$)CH$_2$CH$_3$ |
| 27 | 6-(CH$_2$)$_9$CH$_3$ | 6-(CH$_2$)$_7$CH(CH$_3$)$_2$ | 6-(CH$_2$)$_6$CH(CH$_3$)CH$_2$CH$_3$ |

TABLE 2-continued

| | Column 1 | Column 2 | Column 3 |
|---|---|---|---|
| 28 | 6-$(CH_2)_{11}CH_3$ | 6-$(CH_2)_9CH(CH_3)_2$ | 6-$(CH_2)_8CH(CH_3)CH_2CH_3$ |
| 29 | 6-$(CH_2)_{15}CH_3$ | 6-$(CH_2)_{13}CH(CH_3)_2$ | 6-$(CH_2)_{12}CH(CH_3)CH_2CH_3$ |
| 30 | 7-$(CH_2)_{11}CH_3$ | 7-$(CH_2)_9CH(CH_3)_2$ | 7-$(CH_2)_8CH(CH_3)CH_2CH_3$ |
| | $Z = O, R^1 = H, R^3 = 2'$-F, $R^4 = 6'$-Cl, $R^2 =$ | | |
| 31 | H | 6-(4-Cl—Ph) | 6-$CH_2CH=CH(CH_2)_6CH_3$ |
| 32 | 6-Cl | 6-(4-F—Ph) | 6-$CH_2CH=CH(CH_2)_2CH_3$ |
| 33 | 6-F | 6-$CH_2Ph$ | 6-$OCH_2CH=CH(CH_2)_6CH_3$ |
| 34 | 6-Br | 6-$CH_2CH_2Ph$ | 6-$OCH_2CH=CH(CH_2)_2CH_3$ |
| 35 | 6-$CF_3$ | 6-$CH_2Ph$-4-F | 6-$OCH_2Ph$-4-F |
| 36 | 6-Ph | 6-$CH_2Ph$-4-Cl | 6-$OCH_2CH_2Ph$-4-F |
| 37 | 6-Py | 6-$CH_2Ph$-4-$CF_3$ | 6-$CH_2C\equiv C-(CH_2)_4CH_3$ |
| 38 | 6-OPh | 6-(4-$CH_3(CH_2)_4Ph$) | 6-$OCH_2C\equiv C-(CH_2)_4CH_3$ |
| 39 | 6-SPh | 6-$CH_2Ph$-4-$(CH_2)_9CH_3$ | 6-$CH_2CH=CH-CH_2Ph$ |
| 40 | 6-OPy | 6-$CH_2Ph$-4-$(CH_2)_4CH_3$ | 6-$OCH_2CH=CH-CH_2Ph$ |
| 41 | 7-Cl | 7-(4-Cl—Ph) | 7-$CH_2CH=CH(CH_2)_6CH_3$ |
| 42 | 7-$CF_3$ | 7-$CH_2Ph$ | 7-$OCH_2CH=CH(CH_2)_6CH_3$ |
| 43 | 7-Ph | 7-$CH_2CH_2Ph$ | 7-$OCH_2CH=CH(CH_2)_2CH_3$ |
| 44 | 7-OPh | 7-$CH_2Ph$-4-$CF_3$ | 7-$CH_2C\equiv C-(CH_2)_4CH_3$ |
| 45 | 6-$O(CH_2)_5CH_3$ | 6-$O(CH_2)_3CH(CH_3)_2$ | 6-$O(CH_2)_2CH(CH_3)CH_2CH_3$ |
| 46 | 6-$O(CH_2)_6CH_3$ | 6-$O(CH_2)_4CH(CH_3)_2$ | 6-$O(CH_2)_3CH(CH_3)CH_2CH_3$ |
| 47 | 6-$O(CH_2)_7CH_3$ | 6-$O(CH_2)_5CH(CH_3)_2$ | 6-$O(CH_2)_4CH(CH_3)CH_2CH_3$ |
| 48 | 6-$O(CH_2)_8CH_3$ | 6-$O(CH_2)_6CH(CH_3)_2$ | 6-$O(CH_2)_5CH(CH_3)CH_2CH_3$ |
| 49 | 6-$O(CH_2)_9CH_3$ | 6-$O(CH_2)_7CH(CH_3)_2$ | 6-$O(CH_2)_6CH(CH_3)CH_2CH_3$ |
| 50 | 6-$O(CH_2)_{11}CH_3$ | 6-$O(CH_2)_9CH(CH_3)_2$ | 6-$O(CH_2)_8CH(CH_3)CH_2CH_3$ |
| 51 | 6-$O(CH_2)_{15}CH_3$ | 6-$O(CH_2)_{13}CH(CH_3)_2$ | 6-$O(CH_2)_{12}CH(CH_3)CH_2CH_3$ |
| 52 | 7-$O(CH_2)_{11}CH_3$ | 7-$O(CH_2)_9CH(CH_3)_2$ | 7-$O(CH_2)_8CH(CH_3)CH_2CH_3$ |
| 53 | 6-$(CH_2)_5CH_3$ | 6-$(CH_2)_3CH(CH_3)_2$ | 6-$(CH_2)_2CH(CH_3)CH_2CH_3$ |
| 54 | 6-$(CH_2)_6CH_3$ | 6-$(CH_2)_4CH(CH_3)_2$ | 6-$(CH_2)_3CH(CH_3)CH_2CH_3$ |
| 55 | 6-$(CH_2)_7CH_3$ | 6-$(CH_2)_5CH(CH_3)_2$ | 6-$(CH_2)_4CH(CH_3)CH_2CH_3$ |
| 56 | 6-$(CH_2)_8CH_3$ | 6-$(CH_2)_6CH(CH_3)_2$ | 6-$(CH_2)_5CH(CH_3)CH_2CH_3$ |
| 57 | 6-$(CH_2)_9CH_3$ | 6-$(CH_2)_7CH(CH_3)_2$ | 6-$(CH_2)_6CH(CH_3)CH_2CH_3$ |
| 58 | 6-$(CH_2)_{11}CH_3$ | 6-$(CH_2)_9CH(CH_3)_2$ | 6-$(CH_2)_8CH(CH_3)CH_2CH_3$ |
| 59 | 6-$(CH_2)_{15}CH_3$ | 6-$(CH_2)_{13}CH(CH_3)_2$ | 6-$(CH_2)_{12}CH(CH_3)CH_2CH_3$ |
| 60 | 7-$(CH_2)_{11}CH_3$ | 7-$(CH_2)_9CH(CH_3)_2$ | 7-$(CH_2)_8CH(CH_3)CH_2CH_3$ |
| | $Z = S, R^1 = H, R^3 = 2'$-F, $R^4 = 6'$-F, $R^2 =$ | | |
| 61 | H | 6-(4-Cl—Ph) | 6-$CH_2CH=CH(CH_2)_6CH_3$ |
| 62 | 6-Cl | 6-(4-F—Ph) | 6-$CH_2CH=CH(CH_2)_2CH_3$ |
| 63 | 6-F | 6-$CH_2Ph$ | 6-$OCH_2CH=CH(CH_2)_6CH_3$ |
| 64 | 6-Br | 6-$CH_2CH_2Ph$ | 6-$OCH_2CH=CH(CH_2)_2CH_3$ |
| 65 | 6-$CF_3$ | 6-$CH_2Ph$-4-F | 6-$OCH_2Ph$-4-F |
| 66 | 6-Ph | 6-$CH_2Ph$-4-Cl | 6-$OCH_2CH_2Ph$-4-F |
| 67 | 6-Py | 6-$CH_2Ph$-4-$CF_3$ | 6-$CH_2C\equiv C-(CH_2)_4CH_3$ |
| 68 | 6-OPh | 6-(4-$CH_3(CH_2)_4Ph$) | 6-$OCH_2C\equiv C-(CH_2)_4CH_3$ |
| 69 | 6-SPh | 6-$CH_2Ph$-4-$(CH_2)_9CH_3$ | 6-$CH_2CH=CH-CH_2Ph$ |
| 70 | 6-OPy | 6-$CH_2Ph$-4-$(CH_2)_4CH_3$ | 6-$OCH_2CH=CH-CH_2Ph$ |
| 71 | 7-Cl | 7-(4-Cl—Ph) | 7-$CH_2CH=CH(CH_2)_6CH_3$ |
| 72 | 7-$CF_3$ | 7-$CH_2Ph$ | 7-$OCH_2CH=CH(CH_2)_6CH_3$ |
| 73 | 7-Ph | 7-$CH_2CH_2Ph$ | 7-$OCH_2CH=CH(CH_2)_2CH_3$ |
| 74 | 7-OPh | 7-$CH_2Ph$-4-$CF_3$ | 7-$CH_2C\equiv C-(CH_2)_4CH_3$ |
| 75 | 6-$O(CH_2)_5CH_3$ | 6-$O(CH_2)_3CH(CH_3)_2$ | 6-$O(CH_2)_2CH(CH_3)CH_2CH_3$ |
| 76 | 6-$O(CH_2)_6CH_3$ | 6-$O(CH_2)_4CH(CH_3)_2$ | 6-$O(CH_2)_3CH(CH_3)CH_2CH_3$ |
| 77 | 6-$O(CH_2)_7CH_3$ | 6-$O(CH_2)_5CH(CH_3)_2$ | 6-$O(CH_2)_4CH(CH_3)CH_2CH_3$ |
| 78 | 6-$O(CH_2)_8CH_3$ | 6-$O(CH_2)_6CH(CH_3)_2$ | 6-$O(CH_2)_5CH(CH_3)CH_2CH_3$ |
| 79 | 6-$O(CH_2)_9CH_3$ | 6-$O(CH_2)_7CH(CH_3)_2$ | 6-$O(CH_2)_6CH(CH_3)CH_2CH_3$ |
| 80 | 6-$O(CH_2)_{11}CH_3$ | 6-$O(CH_2)_9CH(CH_3)_2$ | 6-$O(CH_2)_8CH(CH_3)CH_2CH_3$ |
| 81 | 6-$O(CH_2)_{15}CH_3$ | 6-$O(CH_2)_{13}CH(CH_3)_2$ | 6-$O(CH_2)_{12}CH(CH_3)CH_2CH_3$ |
| 82 | 7-$O(CH_2)_{11}CH_3$ | 7-$O(CH_2)_9CH(CH_3)_2$ | 7-$O(CH_2)_8CH(CH_3)CH_2CH_3$ |
| 83 | 6-$(CH_2)_5CH_3$ | 6-$(CH_2)_3CH(CH_3)_2$ | 6-$(CH_2)_2CH(CH_3)CH_2CH_3$ |
| 84 | 6-$(CH_2)_6CH_3$ | 6-$(CH_2)_4CH(CH_3)_2$ | 6-$(CH_2)_3CH(CH_3)CH_2CH_3$ |
| 85 | 6-$(CH_2)_7CH_3$ | 6-$(CH_2)_5CH(CH_3)_2$ | 6-$(CH_2)_4CH(CH_3)CH_2CH_3$ |
| 86 | 6-$(CH_2)_8CH_3$ | 6-$(CH_2)_6CH(CH_3)_2$ | 6-$(CH_2)_5CH(CH_3)CH_2CH_3$ |
| 87 | 6-$(CH_2)_9CH_3$ | 6-$(CH_2)_7CH(CH_3)_2$ | 6-$(CH_2)_6CH(CH_3)CH_2CH_3$ |
| 88 | 6-$(CH_2)_{11}CH_3$ | 6-$(CH_2)_9CH(CH_3)_2$ | 6-$(CH_2)_8CH(CH_3)CH_2CH_3$ |
| 89 | 6-$(CH_2)_{15}CH_3$ | 6-$(CH_2)_{13}CH(CH_3)_2$ | 6-$(CH_2)_{12}CH(CH_3)CH_2CH_3$ |
| 90 | 7-$(CH_2)_{11}CH_3$ | 7-$(CH_2)_9CH(CH_3)_2$ | 7-$(CH_2)_8CH(CH_3)CH_2CH_3$ |
| | $Z = O, R^1 = 8$-Cl, $R^3 = 2'$-F, $R^4 = 6'$-F, $R^2 =$ | | |
| 91 | H | 6-(4-Cl—Ph) | 6-$CH_2CH=CH(CH_2)_6CH_3$ |
| 92 | 6-Cl | 6-(4-F—Ph) | 6-$CH_2CH=CH(CH_2)_2CH_3$ |
| 93 | 6-F | 6-$CH_2Ph$ | 6-$OCH_2CH=CH(CH_2)_6CH_3$ |
| 94 | 6-Br | 6-$CH_2CH_2Ph$ | 6-$OCH_2CH=CH(CH_2)_2CH_3$ |
| 95 | 6-$CF_3$ | 6-$CH_2Ph$-4-F | 6-$OCH_2Ph$-4-F |
| 96 | 6-Ph | 6-$CH_2Ph$-4-Cl | 6-$OCH_2CH_2Ph$-4-F |
| 97 | 6-Py | 6-$CH_2Ph$-4-$CF_3$ | 6-$CH_2C\equiv C-(CH_2)_4CH_3$ |
| 98 | 6-OPh | 6-(4-$CH_3(CH_2)_4Ph$) | 6-$OCH_2C\equiv C-(CH_2)_4CH_3$ |
| 99 | 6-SPh | 6-$CH_2Ph$-4-$(CH_2)_9CH_3$ | 6-$CH_2CH=CH-CH_2Ph$ |
| 100 | 6-OPy | 6-$CH_2Ph$-4-$(CH_2)_4CH_3$ | 6-$OCH_2CH=CH-CH_2Ph$ |
| 101 | 7-Cl | 7-(4-Cl—Ph) | 7-$CH_2CH=CH(CH_2)_6CH_3$ |
| 102 | 7-$CF_3$ | 7-$CH_2Ph$ | 7-$OCH_2CH=CH(CH_2)_6CH_3$ |
| 103 | 7-Ph | 7-$CH_2CH_2Ph$ | 7-$OCH_2CH=CH(CH_2)_2CH_3$ |
| 104 | 7-OPh | 7-$CH_2Ph$-4-$CF_3$ | 7-$CH_2C\equiv C-(CH_2)_4CH_3$ |

TABLE 2-continued

| | Column 1 | Column 2 | Column 3 |
|---|---|---|---|
| 105 | 6-O(CH$_2$)$_5$CH$_3$ | 6-O(CH$_2$)$_3$CH(CH$_3$)$_2$ | 6-O(CH$_2$)$_2$CH(CH$_3$)CH$_2$CH$_3$ |
| 106 | 6-O(CH$_2$)$_6$CH$_3$ | 6-O(CH$_2$)$_4$CH(CH$_3$)$_2$ | 6-O(CH$_2$)$_3$CH(CH$_3$)CH$_2$CH$_3$ |
| 107 | 6-O(CH$_2$)$_7$CH$_3$ | 6-O(CH$_2$)$_5$CH(CH$_3$)$_2$ | 6-O(CH$_2$)$_4$CH(CH$_3$)CH$_2$CH$_3$ |
| 108 | 6-O(CH$_2$)$_8$CH$_3$ | 6-O(CH$_2$)$_6$CH(CH$_3$)$_2$ | 6-O(CH$_2$)$_5$CH(CH$_3$)CH$_2$CH$_3$ |
| 109 | 6-O(CH$_2$)$_9$CH$_3$ | 6-O(CH$_2$)$_7$CH(CH$_3$)$_2$ | 6-O(CH$_2$)$_6$CH(CH$_3$)CH$_2$CH$_3$ |
| 110 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 111 | 6-O(CH$_2$)$_{15}$CH$_3$ | 6-O(CH$_2$)$_{13}$CH(CH$_3$)$_2$ | 6-O(CH$_2$)$_{12}$CH(CH$_3$)CH$_2$CH$_3$ |
| 112 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 113 | 6-(CH$_2$)$_5$CH$_3$ | 6-(CH$_2$)$_3$CH(CH$_3$)$_2$ | 6-(CH$_2$)$_2$CH(CH$_3$)CH$_2$CH$_3$ |
| 114 | 6-(CH$_2$)$_6$CH$_3$ | 6-(CH$_2$)$_4$CH(CH$_3$)$_2$ | 6-(CH$_2$)$_3$CH(CH$_3$)CH$_2$CH$_3$ |
| 115 | 6-(CH$_2$)$_7$CH$_3$ | 6-(CH$_2$)$_5$CH(CH$_3$)$_2$ | 6-(CH$_2$)$_4$CH(CH$_3$)CH$_2$CH$_3$ |
| 116 | 6-(CH$_2$)$_8$CH$_3$ | 6-(CH$_2$)$_6$CH(CH$_3$)$_2$ | 6-(CH$_2$)$_5$CH(CH$_3$)CH$_2$CH$_3$ |
| 117 | 6-(CH$_2$)$_9$CH$_3$ | 6-(CH$_2$)$_7$CH(CH$_3$)$_2$ | 6-(CH$_2$)$_6$CH(CH$_3$)CH$_2$CH$_3$ |
| 118 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| 119 | 6-(CH$_2$)$_{15}$CH$_3$ | 6-(CH$_2$)$_{13}$CH(CH$_3$)$_2$ | 6-(CH$_2$)$_{12}$CH(CH$_3$)CH$_2$CH$_3$ |
| 120 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |
| | $Z = O$, $R^1 = 8$-F, $R^3 = 2'$-F, $R^4 = 6'$-F, $R^2 =$ | | |
| 121 | H | 6-(4-Cl—Ph) | 6-CH$_2$CH=CH(CH$_2$)$_6$CH$_3$ |
| 122 | 6-Cl | 6-(4-F—Ph) | 6-CH$_2$CH=CH(CH$_2$)$_2$CH$_3$ |
| 123 | 6-F | 6-CH$_2$Ph | 6-OCH$_2$CH=CH(CH$_2$)$_6$CH$_3$ |
| 124 | 6-Br | 6-CH$_2$CH$_2$Ph | 6-OCH$_2$CH=CH(CH$_2$)$_2$CH$_3$ |
| 125 | 6-CF$_3$ | 6-CH$_2$Ph-4-F | 6-OCH$_2$Ph-4-F |
| 126 | 6-Ph | 6-CH$_2$Ph-4-Cl | 6-OCH$_2$CH$_2$Ph-4-F |
| 127 | 6-Py | 6-CH$_2$Ph-4-CF$_3$ | 6-CH$_2$C≡C—(CH$_2$)$_4$CH$_3$ |
| 128 | 6-OPh | 6-(4-CH$_3$(CH$_2$)$_4$Ph) | 6-OCH$_2$C≡C—(CH$_2$)$_4$CH$_3$ |
| 129 | 6-SPh | 6-CH$_2$Ph-4-(CH$_2$)$_9$CH$_3$ | 6-CH$_2$CH=CH—CH$_2$Ph |
| 130 | 6-OPy | 6-CH$_2$Ph-4-(CH$_2$)$_4$CH$_3$ | 6-OCH$_2$CH=CH—CH$_2$Ph |
| 131 | 7-Cl | 7-(4-Cl—Ph) | 7-CH$_2$CH=CH(CH$_2$)$_6$CH$_3$ |
| 132 | 7-CF$_3$ | 7-CH$_2$Ph | 7-OCH$_2$CH=CH(CH$_2$)$_6$CH$_3$ |
| 133 | 7-Ph | 7-CH$_2$CH$_2$Ph | 7-OCH$_2$CH=CH(CH$_2$)$_2$CH$_3$ |
| 134 | 7-OPh | 7-CH$_2$Ph-4-CF$_3$ | 7-CH$_2$C≡C—(CH$_2$)$_4$CH$_3$ |
| 135 | 6-O(CH$_2$)$_5$CH$_3$ | 6-O(CH$_2$)$_3$CH(CH$_3$)$_2$ | 6-O(CH$_2$)$_2$CH(CH$_3$)CH$_2$CH$_3$ |
| 136 | 6-O(CH$_2$)$_6$CH$_3$ | 6-O(CH$_2$)$_4$CH(CH$_3$)$_2$ | 6-O(CH$_2$)$_3$CH(CH$_3$)CH$_2$CH$_3$ |
| 137 | 6-O(CH$_2$)$_7$CH$_3$ | 6-O(CH$_2$)$_5$CH(CH$_3$)$_2$ | 6-O(CH$_2$)$_4$CH(CH$_3$)CH$_2$CH$_3$ |
| 138 | 6-O(CH$_2$)$_8$CH$_3$ | 6-O(CH$_2$)$_6$CH(CH$_3$)$_2$ | 6-O(CH$_2$)$_5$CH(CH$_3$)CH$_2$CH$_3$ |
| 139 | 6-O(CH$_2$)$_9$CH$_3$ | 6-O(CH$_2$)$_7$CH(CH$_3$)$_2$ | 6-O(CH$_2$)$_6$CH(CH$_3$)CH$_2$CH$_3$ |
| 140 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 141 | 6-O(CH$_2$)$_{15}$CH$_3$ | 6-O(CH$_2$)$_{13}$CH(CH$_3$)$_2$ | 6-O(CH$_2$)$_{12}$CH(CH$_3$)CH$_2$CH$_3$ |
| 142 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 143 | 6-(CH$_2$)$_5$CH$_3$ | 6-(CH$_2$)$_3$CH(CH$_3$)$_2$ | 6-(CH$_2$)$_2$CH(CH$_3$)CH$_2$CH$_3$ |
| 144 | 6-(CH$_2$)$_6$CH$_3$ | 6-(CH$_2$)$_4$CH(CH$_3$)$_2$ | 6-(CH$_2$)$_3$CH(CH$_3$)CH$_2$CH$_3$ |
| 145 | 6-(CH$_2$)$_7$CH$_3$ | 6-(CH$_2$)$_5$CH(CH$_3$)$_2$ | 6-(CH$_2$)$_4$CH(CH$_3$)CH$_2$CH$_3$ |
| 146 | 6-(CH$_2$)$_8$CH$_3$ | 6-(CH$_2$)$_6$CH(CH$_3$)$_2$ | 6-(CH$_2$)$_5$CH(CH$_3$)CH$_2$CH$_3$ |
| 147 | 6-(CH$_2$)$_9$CH$_3$ | 6-(CH$_2$)$_7$CH(CH$_3$)$_2$ | 6-(CH$_2$)$_6$CH(CH$_3$)CH$_2$CH$_3$ |
| 148 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| 149 | 6-(CH$_2$)$_{15}$CH$_3$ | 6-(CH$_2$)$_{13}$CH(CH$_3$)$_2$ | 6-(CH$_2$)$_{12}$CH(CH$_3$)CH$_2$CH$_3$ |
| 150 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |

TABLE 3

| | Column 1 | Column 2 | Column 3 |
|---|---|---|---|
| | $Z = O$, $R^1 = H$, $R^3 = 2'$-F, $R^4 = 6'$-F, $R^2 =$ | | |
| 1 | H | 6-(4-Cl—Ph) | 6-CH$_2$CH=CH(CH$_2$)$_6$CH$_3$ |
| 2 | 6-Cl | 6-(4-F—Ph) | 6-CH$_2$CH=CH(CH$_2$)$_2$CH$_3$ |
| 3 | 6-F | 6-CH$_2$Ph | 6-OCH$_2$CH=CH(CH$_2$)$_6$CH$_3$ |
| 4 | 6-Br | 6-CH$_2$CH$_2$Ph | 6-OCH$_2$CH=CH(CH$_2$)$_2$CH$_3$ |
| 5 | 6-CF$_3$ | 6-CH$_2$Ph-4-F | 6-OCH$_2$Ph-4-F |
| 6 | 6-Ph | 6-CH$_2$Ph-4-Cl | 6-OCH$_2$CH$_2$Ph-4-F |
| 7 | 6-Py | 6-CH$_2$Ph-4-CF$_3$ | 6-CH$_2$C≡C—(CH$_2$)$_4$CH$_3$ |
| 8 | 6-OPh | 6-(4-CH$_3$(CH$_2$)$_4$Ph) | 6-OCH$_2$C≡C—(CH$_2$)$_4$CH$_3$ |
| 9 | 6-SPh | 6-CH$_2$Ph-4-(CH$_2$)$_9$CH$_3$ | 6-CH$_2$CH=CH—CH$_2$Ph |
| 10 | 6-OPy | 6-CH$_2$Ph-4-(CH$_2$)$_4$CH$_3$ | 6-OCH$_2$CH=CH—CH$_2$Ph |
| 11 | 7-Cl | 7-(4-Cl—Ph) | 7-CH$_2$CH=CH(CH$_2$)$_6$CH$_3$ |
| 12 | 7-CF$_3$ | 7-CH$_2$Ph | 7-OCH$_2$CH=CH(CH$_2$)$_6$CH$_3$ |
| 13 | 7-Ph | 7-CH$_2$CH$_2$Ph | 7-OCH$_2$CH=CH(CH$_2$)$_2$CH$_3$ |
| 14 | 7-OPh | 7-CH$_2$Ph-4-CF$_3$ | 7-CH$_2$C≡C—(CH$_2$)$_4$CH$_3$ |
| 15 | 6-O(CH$_2$)$_5$CH$_3$ | 6-O(CH$_2$)$_3$CH(CH$_3$)$_2$ | 6-O(CH$_2$)$_2$CH(CH$_3$)CH$_2$CH$_3$ |
| 16 | 6-O(CH$_2$)$_6$CH$_3$ | 6-O(CH$_2$)$_4$CH(CH$_3$)$_2$ | 6-O(CH$_2$)$_3$CH(CH$_3$)CH$_2$CH$_3$ |
| 17 | 6-O(CH$_2$)$_7$CH$_3$ | 6-O(CH$_2$)$_5$CH(CH$_3$)$_2$ | 6-O(CH$_2$)$_4$CH(CH$_3$)CH$_2$CH$_3$ |
| 18 | 6-O(CH$_2$)$_8$CH$_3$ | 6-O(CH$_2$)$_6$CH(CH$_3$)$_2$ | 6-O(CH$_2$)$_5$CH(CH$_3$)CH$_2$CH$_3$ |
| 19 | 6-O(CH$_2$)$_9$CH$_3$ | 6-O(CH$_2$)$_7$CH(CH$_3$)$_2$ | 6-O(CH$_2$)$_6$CH(CH$_3$)CH$_2$CH$_3$ |
| 20 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 21 | 6-O(CH$_2$)$_{15}$CH$_3$ | 6-O(CH$_2$)$_{13}$CH(CH$_3$)$_2$ | 6-O(CH$_2$)$_{12}$CH(CH$_3$)CH$_2$CH$_3$ |
| 22 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 23 | 6-(CH$_2$)$_5$CH$_3$ | 6-(CH$_2$)$_3$CH(CH$_3$)$_2$ | 6-(CH$_2$)$_2$CH(CH$_3$)CH$_2$CH$_3$ |
| 24 | 6-(CH$_2$)$_6$CH$_3$ | 6-(CH$_2$)$_4$CH(CH$_3$)$_2$ | 6-(CH$_2$)$_3$CH(CH$_3$)CH$_2$CH$_3$ |
| 25 | 6-(CH$_2$)$_7$CH$_3$ | 6-(CH$_2$)$_5$CH(CH$_3$)$_2$ | 6-(CH$_2$)$_4$CH(CH$_3$)CH$_2$CH$_3$ |
| 26 | 6-(CH$_2$)$_8$CH$_3$ | 6-(CH$_2$)$_6$CH(CH$_3$)$_2$ | 6-(CH$_2$)$_5$CH(CH$_3$)CH$_2$CH$_3$ |
| 27 | 6-(CH$_2$)$_9$CH$_3$ | 6-(CH$_2$)$_7$CH(CH$_3$)$_2$ | 6-(CH$_2$)$_6$CH(CH$_3$)CH$_2$CH$_3$ |

TABLE 3-continued

|  | Column 1 | Column 2 | Column 3 |
|---|---|---|---|
| 28 | 6-$(CH_2)_{11}CH_3$ | 6-$(CH_2)_9CH(CH_3)_2$ | 6-$(CH_2)_8CH(CH_3)CH_2CH_3$ |
| 29 | 6-$(CH_2)_{15}CH_3$ | 6-$(CH_2)_{13}CH(CH_3)_2$ | 6-$(CH_2)_{12}CH(CH_3)CH_2CH_3$ |
| 30 | 7-$(CH_2)_{11}CH_3$ | 7-$(CH_2)_9CH(CH_3)_2$ | 7-$(CH_2)_8CH(CH_3)CH_2CH_3$ |
| | | $Z = O, R^1 = H, R^3 = 2'\text{-}F, R^4 = 6'\text{-}Cl, R^2 =$ | |
| 31 | H | 6-(4-Cl—Ph) | 6-$CH_2CH{=}CH(CH_2)_6CH_3$ |
| 32 | 6-Cl | 6-(4-F—Ph) | 6-$CH_2CH{=}CH(CH_2)_2CH_3$ |
| 33 | 6-F | 6-$CH_2Ph$ | 6-$OCH_2CH{=}CH(CH_2)_6CH_3$ |
| 34 | 6-Br | 6-$CH_2CH_2Ph$ | 6-$OCH_2CH{=}CH(CH_2)_2CH_3$ |
| 35 | 6-$CF_3$ | 6-$CH_2Ph$-4-F | 6-$OCH_2Ph$-4-F |
| 36 | 6-Ph | 6-$CH_2Ph$-4-Cl | 6-$OCH_2CH_2Ph$-4-F |
| 37 | 6-Py | 6-$CH_2Ph$-4-$CF_3$ | 6-$CH_2C{\equiv}C$—$(CH_2)_4CH_3$ |
| 38 | 6-OPh | 6-(4-$CH_3(CH_2)_4Ph$) | 6-$OCH_2C{\equiv}C$—$(CH_2)_4CH_3$ |
| 39 | 6-SPh | 6-$CH_2Ph$-4-$(CH_2)_9CH_3$ | 6-$CH_2CH{=}CH$—$CH_2Ph$ |
| 40 | 6-OPy | 6-$CH_2Ph$-4-$(CH_2)_4CH_3$ | 6-$OCH_2CH{=}CH$—$CH_2Ph$ |
| 41 | 7-Cl | 7-(4-Cl—Ph) | 7-$CH_2CH{=}CH(CH_2)_6CH_3$ |
| 42 | 7-$CF_3$ | 7-$CH_2Ph$ | 7-$OCH_2CH{=}CH(CH_2)_6CH_3$ |
| 43 | 7-Ph | 7-$CH_2CH_2Ph$ | 7-$OCH_2CH{=}CH(CH_2)_2CH_3$ |
| 44 | 7-OPh | 7-$CH_2Ph$-4-$CF_3$ | 7-$CH_2C{\equiv}C$—$(CH_2)_4CH_3$ |
| 45 | 6-$O(CH_2)_5CH_3$ | 6-$O(CH_2)_3CH(CH_3)_2$ | 6-$O(CH_2)_2CH(CH_3)CH_2CH_3$ |
| 46 | 6-$O(CH_2)_6CH_3$ | 6-$O(CH_2)_4CH(CH_3)_2$ | 6-$O(CH_2)_3CH(CH_3)CH_2CH_3$ |
| 47 | 6-$O(CH_2)_7CH_3$ | 6-$O(CH_2)_5CH(CH_3)_2$ | 6-$O(CH_2)_4CH(CH_3)CH_2CH_3$ |
| 48 | 6-$O(CH_2)_8CH_3$ | 6-$O(CH_2)_6CH(CH_3)_2$ | 6-$O(CH_2)_5CH(CH_3)CH_2CH_3$ |
| 49 | 6-$O(CH_2)_9CH_3$ | 6-$O(CH_2)_7CH(CH_3)_2$ | 6-$O(CH_2)_6CH(CH_3)CH_2CH_3$ |
| 50 | 6-$O(CH_2)_{11}CH_3$ | 6-$O(CH_2)_9CH(CH_3)_2$ | 6-$O(CH_2)_8CH(CH_3)CH_2CH_3$ |
| 51 | 6-$O(CH_2)_{15}CH_3$ | 6-$O(CH_2)_{13}CH(CH_3)_2$ | 6-$O(CH_2)_{12}CH(CH_3)CH_2CH_3$ |
| 52 | 7-$O(CH_2)_{11}CH_3$ | 7-$O(CH_2)_9CH(CH_3)_2$ | 7-$O(CH_2)_8CH(CH_3)CH_2CH_3$ |
| 53 | 6-$(CH_2)_5CH_3$ | 6-$(CH_2)_3CH(CH_3)_2$ | 6-$(CH_2)_2CH(CH_3)CH_2CH_3$ |
| 54 | 6-$(CH_2)_6CH_3$ | 6-$(CH_2)_4CH(CH_3)_2$ | 6-$(CH_2)_3CH(CH_3)CH_2CH_3$ |
| 55 | 6-$(CH_2)_7CH_3$ | 6-$(CH_2)_5CH(CH_3)_2$ | 6-$(CH_2)_4CH(CH_3)CH_2CH_3$ |
| 56 | 6-$(CH_2)_8CH_3$ | 6-$(CH_2)_6CH(CH_3)_2$ | 6-$(CH_2)_5CH(CH_3)CH_2CH_3$ |
| 57 | 6-$(CH_2)_9CH_3$ | 6-$(CH_2)_7CH(CH_3)_2$ | 6-$(CH_2)_6CH(CH_3)CH_2CH_3$ |
| 58 | 6-$(CH_2)_{11}CH_3$ | 6-$(CH_2)_9CH(CH_3)_2$ | 6-$(CH_2)_8CH(CH_3)CH_2CH_3$ |
| 59 | 6-$(CH_2)_{15}CH_3$ | 6-$(CH_2)_{13}CH(CH_3)_2$ | 6-$(CH_2)_{12}CH(CH_3)CH_2CH_3$ |
| 60 | 7-$(CH_2)_{11}CH_3$ | 7-$(CH_2)_9CH(CH_3)_2$ | 7-$(CH_2)_8CH(CH_3)CH_2CH_3$ |
| | | $Z = O, R^1 = 8\text{-}Cl, R^3 = 2'\text{-}F, R^4 = 6'\text{-}F, R^2 =$ | |
| 61 | H | 6-(4-Cl—Ph) | 6-$CH_2CH{=}CH(CH_2)_6CH_3$ |
| 62 | 6-Cl | 6-(4-F—Ph) | 6-$CH_2CH{=}CH(CH_2)_2CH_3$ |
| 63 | 6-F | 6-$CH_2Ph$ | 6-$OCH_2CH{=}CH(CH_2)_6CH_3$ |
| 64 | 6-Br | 6-$CH_2CH_2Ph$ | 6-$OCH_2CH{=}CH(CH_2)_2CH_3$ |
| 65 | 6-$CF_3$ | 6-$CH_2Ph$-4-F | 6-$OCH_2Ph$-4-F |
| 66 | 6-Ph | 6-$CH_2Ph$-4-Cl | 6-$OCH_2CH_2Ph$-4-F |
| 67 | 6-Py | 6-$CH_2Ph$-4-$CF_3$ | 6-$CH_2C{\equiv}C$—$(CH_2)_4CH_3$ |
| 68 | 6-OPh | 6-(4-$CH_3(CH_2)_4Ph$) | 6-$OCH_2C{\equiv}C$—$(CH_2)_4CH_3$ |
| 69 | 6-SPh | 6-$CH_2Ph$-4-$(CH_2)_9CH_3$ | 6-$CH_2CH{=}CH$—$CH_2Ph$ |
| 70 | 6-OPy | 6-$CH_2Ph$-4-$(CH_2)_4CH_3$ | 6-$OCH_2CH{=}CH$—$CH_2Ph$ |
| 71 | 7-Cl | 7-(4-Cl—Ph) | 7-$CH_2CH{=}CH(CH_2)_6CH_3$ |
| 72 | 7-$CF_3$ | 7-$CH_2Ph$ | 7-$OCH_2CH{=}CH(CH_2)_6CH_3$ |
| 73 | 7-Ph | 7-$CH_2CH_2Ph$ | 7-$OCH_2CH{=}CH(CH_2)_2CH_3$ |
| 74 | 7-OPh | 7-$CH_2Ph$-4-$CF_3$ | 7-$CH_2C{\equiv}C$—$(CH_2)_4CH_3$ |
| 75 | 6-$O(CH_2)_5CH_3$ | 6-$O(CH_2)_3CH(CH_3)_2$ | 6-$O(CH_2)_2CH(CH_3)CH_2CH_3$ |
| 76 | 6-$O(CH_2)_6CH_3$ | 6-$O(CH_2)_4CH(CH_3)_2$ | 6-$O(CH_2)_3CH(CH_3)CH_2CH_3$ |
| 77 | 6-$O(CH_2)_7CH_3$ | 6-$O(CH_2)_5CH(CH_3)_2$ | 6-$O(CH_2)_4CH(CH_3)CH_2CH_3$ |
| 78 | 6-$O(CH_2)_8CH_3$ | 6-$O(CH_2)_6CH(CH_3)_2$ | 6-$O(CH_2)_5CH(CH_3)CH_2CH_3$ |
| 79 | 6-$O(CH_2)_9CH_3$ | 6-$O(CH_2)_7CH(CH_3)_2$ | 6-$O(CH_2)_6CH(CH_3)CH_2CH_3$ |
| 80 | 6-$O(CH_2)_{11}CH_3$ | 6-$O(CH_2)_9CH(CH_3)_2$ | 6-$O(CH_2)_8CH(CH_3)CH_2CH_3$ |
| 81 | 6-$O(CH_2)_{15}CH_3$ | 6-$O(CH_2)_{13}CH(CH_3)_2$ | 6-$O(CH_2)_{12}CH(CH_3)CH_2CH_3$ |
| 82 | 7-$O(CH_2)_{11}CH_3$ | 7-$O(CH_2)_9CH(CH_3)_2$ | 7-$O(CH_2)_8CH(CH_3)CH_2CH_3$ |
| 83 | 6-$(CH_2)_5CH_3$ | 6-$(CH_2)_3CH(CH_3)_2$ | 6-$(CH_2)_2CH(CH_3)CH_2CH_3$ |
| 84 | 6-$(CH_2)_6CH_3$ | 6-$(CH_2)_4CH(CH_3)_2$ | 6-$(CH_2)_3CH(CH_3)CH_2CH_3$ |
| 85 | 6-$(CH_2)_7CH_3$ | 6-$(CH_2)_5CH(CH_3)_2$ | 6-$(CH_2)_4CH(CH_3)CH_2CH_3$ |
| 86 | 6-$(CH_2)_8CH_3$ | 6-$(CH_2)_6CH(CH_3)_2$ | 6-$(CH_2)_5CH(CH_3)CH_2CH_3$ |
| 87 | 6-$(CH_2)_9CH_3$ | 6-$(CH_2)_7CH(CH_3)_2$ | 6-$(CH_2)_6CH(CH_3)CH_2CH_3$ |
| 88 | 6-$(CH_2)_{11}CH_3$ | 6-$(CH_2)_9CH(CH_3)_2$ | 6-$(CH_2)_8CH(CH_3)CH_2CH_3$ |
| 89 | 6-$(CH_2)_{15}CH_3$ | 6-$(CH_2)_{13}CH(CH_3)_2$ | 6-$(CH_2)_{12}CH(CH_3)CH_2CH_3$ |
| 90 | 7-$(CH_2)_{11}CH_3$ | 7-$(CH_2)_9CH(CH_3)_2$ | 7-$(CH_2)_8CH(CH_3)CH_2CH_3$ |
| | | $Z = O, R^1 = 8\text{-}F, R^3 = 2'\text{-}F, R^4 = 6'\text{-}F, R^2 =$ | |
| 91 | H | 6-(4-Cl—Ph) | 6-$CH_2CH{=}CH(CH_2)_6CH_3$ |
| 92 | 6-Cl | 6-(4-F—Ph) | 6-$CH_2CH{=}CH(CH_2)_2CH_3$ |
| 93 | 6-F | 6-$CH_2Ph$ | 6-$OCH_2CH{=}CH(CH_2)_6CH_3$ |
| 94 | 6-Br | 6-$CH_2CH_2Ph$ | 6-$OCH_2CH{=}CH(CH_2)_2CH_3$ |
| 95 | 6-$CF_3$ | 6-$CH_2Ph$-4-F | 6-$OCH_2Ph$-4-F |
| 96 | 6-Ph | 6-$CH_2Ph$-4-Cl | 6-$OCH_2CH_2Ph$-4-F |
| 97 | 6-Py | 6-$CH_2Ph$-4-$CF_3$ | 6-$CH_2C{\equiv}C$—$(CH_2)_4CH_3$ |
| 98 | 6-OPh | 6-(4-$CH_3(CH_2)_4Ph$) | 6-$OCH_2C{\equiv}C$—$(CH_2)_4CH_3$ |
| 99 | 6-SPh | 6-$CH_2Ph$-4-$(CH_2)_9CH_3$ | 6-$CH_2CH{=}CH$—$CH_2Ph$ |
| 100 | 6-OPy | 6-$CH_2Ph$-4-$(CH_2)_4CH_3$ | 6-$OCH_2CH{=}CH$—$CH_2Ph$ |
| 101 | 7-Cl | 7-(4-Cl—Ph) | 7-$CH_2CH{=}CH(CH_2)_6CH_3$ |
| 102 | 7-$CF_3$ | 7-$CH_2Ph$ | 7-$OCH_2CH{=}CH(CH_2)_6CH_3$ |
| 103 | 7-Ph | 7-$CH_2CH_2Ph$ | 7-$OCH_2CH{=}CH(CH_2)_2CH_3$ |
| 104 | 7-OPh | 7-$CH_2Ph$-4-$CF_3$ | 7-$CH_2C{\equiv}C$—$(CH_2)_4CH_3$ |

TABLE 3-continued

|     | Column 1 | Column 2 | Column 3 |
| --- | --- | --- | --- |
| 105 | 6-O(CH$_2$)$_5$CH$_3$ | 6-O(CH$_2$)$_3$CH(CH$_3$)$_2$ | 6-O(CH$_2$)$_2$CH(CH$_3$)CH$_2$CH$_3$ |
| 106 | 6-O(CH$_2$)$_6$CH$_3$ | 6-O(CH$_2$)$_4$CH(CH$_3$)$_2$ | 6-O(CH$_2$)$_3$CH(CH$_3$)CH$_2$CH$_3$ |
| 107 | 6-O(CH$_2$)$_7$CH$_3$ | 6-O(CH$_2$)$_5$CH(CH$_3$)$_2$ | 6-O(CH$_2$)$_4$CH(CH$_3$)CH$_2$CH$_3$ |
| 108 | 6-O(CH$_2$)$_8$CH$_3$ | 6-O(CH$_2$)$_6$CH(CH$_3$)$_2$ | 6-O(CH$_2$)$_5$CH(CH$_3$)CH$_2$CH$_3$ |
| 109 | 6-O(CH$_2$)$_9$CH$_3$ | 6-O(CH$_2$)$_7$CH(CH$_3$)$_2$ | 6-O(CH$_2$)$_6$CH(CH$_3$)CH$_2$CH$_3$ |
| 110 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 111 | 6-O(CH$_2$)$_{15}$CH$_3$ | 6-O(CH$_2$)$_{13}$CH(CH$_3$)$_2$ | 6-O(CH$_2$)$_{12}$CH(CH$_3$)CH$_2$CH$_3$ |
| 112 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 113 | 6-(CH$_2$)$_5$CH$_3$ | 6-(CH$_2$)$_3$CH(CH$_3$)$_2$ | 6-(CH$_2$)$_2$CH(CH$_3$)CH$_2$CH$_3$ |
| 114 | 6-(CH$_2$)$_6$CH$_3$ | 6-(CH$_2$)$_4$CH(CH$_3$)$_2$ | 6-(CH$_2$)$_3$CH(CH$_3$)CH$_2$CH$_3$ |
| 115 | 6-(CH$_2$)$_7$CH$_3$ | 6-(CH$_2$)$_5$CH(CH$_3$)$_2$ | 6-(CH$_2$)$_4$CH(CH$_3$)CH$_2$CH$_3$ |
| 116 | 6-(CH$_2$)$_8$CH$_3$ | 6-(CH$_2$)$_6$CH(CH$_3$)$_2$ | 6-(CH$_2$)$_5$CH(CH$_3$)CH$_2$CH$_3$ |
| 117 | 6-(CH$_2$)$_9$CH$_3$ | 6-(CH$_2$)$_7$CH(CH$_3$)$_2$ | 6-(CH$_2$)$_6$CH(CH$_3$)CH$_2$CH$_3$ |
| 118 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| 119 | 6-(CH$_2$)$_{15}$CH$_3$ | 6-(CH$_2$)$_{13}$CH(CH$_3$)$_2$ | 6-(CH$_2$)$_{12}$CH(CH$_3$)CH$_2$CH$_3$ |
| 120 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |

TABLE 4

|     | Column 1 | Column 2 | Column 3 |
| --- | --- | --- | --- |
| | \multicolumn{3}{c}{Z = O, R$^1$ = H, R$^3$ = 2'-F, R$^4$ = 6'-F, R$^2$ =} | | |
| 1 | H | 5-(4-Cl—Ph) | 5-CH$_2$CH=CH(CH$_2$)$_6$CH$_3$ |
| 2 | 5-Cl | 5-(4-F—Ph) | 5-CH$_2$CH=CH(CH$_2$)$_2$CH$_3$ |
| 3 | 5-F | 5-CH$_2$Ph | 5-OCH$_2$CH=CH(CH$_2$)$_6$CH$_3$ |
| 4 | 5-Br | 5-CH$_2$CH$_2$Ph | 5-OCH$_2$CH=CH(CH$_2$)$_2$CH$_3$ |
| 5 | 5-CF$_3$ | 5-CH$_2$Ph-4-F | 5-OCH$_2$Ph-4-F |
| 6 | 5-Ph | 5-CH$_2$Ph-4-Cl | 5-OCH$_2$CH$_2$Ph-4-F |
| 7 | 5-Py | 5-CH$_2$Ph-4-CF$_3$ | 5-CH$_2$C≡C—(CH$_2$)$_4$CH$_3$ |
| 8 | 5-OPh | 5-(4-CH$_3$(CH$_2$)$_4$Ph) | 5-OCH$_2$C≡C—(CH$_2$)$_4$CH$_3$ |
| 9 | 5-SPh | 5-CH$_2$Ph-4-(CH$_2$)$_9$CH$_3$ | 5-CH$_2$CH=CH—CH$_2$Ph |
| 10 | 5-OPy | 5-CH$_2$Ph-4-(CH$_2$)$_4$CH$_3$ | 5-OCH$_2$CH=CH—CH$_2$Ph |
| 11 | 6-Cl | 6-(4-Cl—Ph) | 6-CH$_2$CH=CH(CH$_2$)$_6$CH$_3$ |
| 12 | 6-CF$_3$ | 6-CH$_2$Ph | 6-OCH$_2$CH=CH(CH$_2$)$_6$CH$_3$ |
| 13 | 6-Ph | 6-CH$_2$CH$_2$Ph | 6-OCH$_2$CH=CH(CH$_2$)$_2$CH$_3$ |
| 14 | 6-OPh | 6-CH$_2$Ph-4-CF$_3$ | 6-CH$_2$C≡C—(CH$_2$)$_4$CH$_3$ |
| 15 | 5-O(CH$_2$)$_5$CH$_3$ | 5-O(CH$_2$)$_3$CH(CH$_3$)$_2$ | 5-O(CH$_2$)$_2$CH(CH$_3$)CH$_2$CH$_3$ |
| 16 | 5-O(CH$_2$)$_6$CH$_3$ | 5-O(CH$_2$)$_4$CH(CH$_3$)$_2$ | 5-O(CH$_2$)$_3$CH(CH$_3$)CH$_2$CH$_3$ |
| 17 | 5-O(CH$_2$)$_7$CH$_3$ | 5-O(CH$_2$)$_5$CH(CH$_3$)$_2$ | 5-O(CH$_2$)$_4$CH(CH$_3$)CH$_2$CH$_3$ |
| 18 | 5-O(CH$_2$)$_8$CH$_3$ | 5-O(CH$_2$)$_6$CH(CH$_3$)$_2$ | 5-O(CH$_2$)$_5$CH(CH$_3$)CH$_2$CH$_3$ |
| 19 | 5-O(CH$_2$)$_9$CH$_3$ | 5-O(CH$_2$)$_7$CH(CH$_3$)$_2$ | 5-O(CH$_2$)$_6$CH(CH$_3$)CH$_2$CH$_3$ |
| 20 | 5-O(CH$_2$)$_{11}$CH$_3$ | 5-O(CH$_2$)$_9$CH(CH$_3$)$_2$ | 5-O(CH$_2$)$_8$CH(CH$_3$)CH$_2$CH$_3$ |
| 21 | 5-O(CH$_2$)$_{15}$CH$_3$ | 5-O(CH$_2$)$_{13}$CH(CH$_3$)$_2$ | 5-O(CH$_2$)$_{12}$CH(CH$_3$)CH$_2$CH$_3$ |
| 22 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 23 | 5-(CH$_2$)$_5$CH$_3$ | 5-(CH$_2$)$_3$CH(CH$_3$)$_2$ | 5-(CH$_2$)$_2$CH(CH$_3$)CH$_2$CH$_3$ |
| 24 | 5-(CH$_2$)$_6$CH$_3$ | 5-(CH$_2$)$_4$CH(CH$_3$)$_2$ | 5-(CH$_2$)$_3$CH(CH$_3$)CH$_2$CH$_3$ |
| 25 | 5-(CH$_2$)$_7$CH$_3$ | 5-(CH$_2$)$_5$CH(CH$_3$)$_2$ | 5-(CH$_2$)$_4$CH(CH$_3$)CH$_2$CH$_3$ |
| 26 | 5-(CH$_2$)$_8$CH$_3$ | 5-(CH$_2$)$_6$CH(CH$_3$)$_2$ | 5-(CH$_2$)$_5$CH(CH$_3$)CH$_2$CH$_3$ |
| 27 | 5-(CH$_2$)$_9$CH$_3$ | 5-(CH$_2$)$_7$CH(CH$_3$)$_2$ | 5-(CH$_2$)$_6$CH(CH$_3$)CH$_2$CH$_3$ |
| 28 | 5-(CH$_2$)$_{11}$CH$_3$ | 5-(CH$_2$)$_9$CH(CH$_3$)$_2$ | 5-(CH$_2$)$_8$CH(CH$_3$)CH$_2$CH$_3$ |
| 29 | 5-(CH$_2$)$_{15}$CH$_3$ | 5-(CH$_2$)$_{13}$CH(CH$_3$)$_2$ | 5-(CH$_2$)$_{12}$CH(CH$_3$)CH$_2$CH$_3$ |
| 30 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| | \multicolumn{3}{c}{Z = O, R$^1$ = 8-Cl, R$^3$ = 2'-F, R$^4$ = 6'-F, R$^2$ =} | | |
| 31 | H | 5-(4-Cl—Ph) | 5-CH$_2$CH=CH(CH$_2$)$_6$CH$_3$ |
| 32 | 5-Cl | 5-(4-F—Ph) | 5-CH$_2$CH=CH(CH$_2$)$_2$CH$_3$ |
| 33 | 5-F | 5-CH$_2$Ph | 5-OCH$_2$CH=CH(CH$_2$)$_6$CH$_3$ |
| 34 | 5-Br | 5-CH$_2$CH$_2$Ph | 5-OCH$_2$CH=CH(CH$_2$)$_2$CH$_3$ |
| 35 | 5-CF$_3$ | 5-CH$_2$Ph-4-F | 5-OCH$_2$Ph-4-F |
| 36 | 5-Ph | 5-CH$_2$Ph-4-Cl | 5-OCH$_2$CH$_2$Ph-4-F |
| 37 | 5-Py | 5-CH$_2$Ph-4-CF$_3$ | 5-CH$_2$C≡C—(CH$_2$)$_4$CH$_3$ |
| 38 | 5-OPh | 5-(4-CH$_3$(CH$_2$)$_4$Ph) | 5-OCH$_2$C≡C—(CH$_2$)$_4$CH$_3$ |
| 39 | 5-SPh | 5-CH$_2$Ph-4-(CH$_2$)$_9$CH$_3$ | 5-CH$_2$CH=CH—CH$_2$Ph |
| 40 | 5-OPy | 5-CH$_2$Ph-4-(CH$_2$)$_4$CH$_3$ | 5-OCH$_2$CH=CH—CH$_2$Ph |
| 41 | 6-Cl | 6-(4-Cl—Ph) | 6-CH$_2$CH=CH(CH$_2$)$_6$CH$_3$ |
| 42 | 6-CF$_3$ | 6-CH$_2$Ph | 6-OCH$_2$CH=CH(CH$_2$)$_6$CH$_3$ |
| 43 | 6-Ph | 6-CH$_2$CH$_2$Ph | 6-OCH$_2$CH=CH(CH$_2$)$_2$CH$_3$ |
| 44 | 6-OPh | 6-CH$_2$Ph-4-CF$_3$ | 6-CH$_2$C≡C—(CH$_2$)$_4$CH$_3$ |
| 45 | 5-O(CH$_2$)$_5$CH$_3$ | 5-O(CH$_2$)$_3$CH(CH$_3$)$_2$ | 5-O(CH$_2$)$_2$CH(CH$_3$)CH$_2$CH$_3$ |
| 46 | 5-O(CH$_2$)$_6$CH$_3$ | 5-O(CH$_2$)$_4$CH(CH$_3$)$_2$ | 5-O(CH$_2$)$_3$CH(CH$_3$)CH$_2$CH$_3$ |
| 47 | 5-O(CH$_2$)$_7$CH$_3$ | 5-O(CH$_2$)$_5$CH(CH$_3$)$_2$ | 5-O(CH$_2$)$_4$CH(CH$_3$)CH$_2$CH$_3$ |
| 48 | 5-O(CH$_2$)$_8$CH$_3$ | 5-O(CH$_2$)$_6$CH(CH$_3$)$_2$ | 5-O(CH$_2$)$_5$CH(CH$_3$)CH$_2$CH$_3$ |
| 49 | 5-O(CH$_2$)$_9$CH$_3$ | 5-O(CH$_2$)$_7$CH(CH$_3$)$_2$ | 5-O(CH$_2$)$_6$CH(CH$_3$)CH$_2$CH$_3$ |
| 50 | 5-O(CH$_2$)$_{11}$CH$_3$ | 5-O(CH$_2$)$_9$CH(CH$_3$)$_2$ | 5-O(CH$_2$)$_8$CH(CH$_3$)CH$_2$CH$_3$ |
| 51 | 5-O(CH$_2$)$_{15}$CH$_3$ | 5-O(CH$_2$)$_{13}$CH(CH$_3$)$_2$ | 5-O(CH$_2$)$_{12}$CH(CH$_3$)CH$_2$CH$_3$ |
| 52 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 53 | 5-(CH$_2$)$_5$CH$_3$ | 5-(CH$_2$)$_3$CH(CH$_3$)$_2$ | 5-(CH$_2$)$_2$CH(CH$_3$)CH$_2$CH$_3$ |
| 54 | 5-(CH$_2$)$_6$CH$_3$ | 5-(CH$_2$)$_4$CH(CH$_3$)$_2$ | 5-(CH$_2$)$_3$CH(CH$_3$)CH$_2$CH$_3$ |
| 55 | 5-(CH$_2$)$_7$CH$_3$ | 5-(CH$_2$)$_5$CH(CH$_3$)$_2$ | 5-(CH$_2$)$_4$CH(CH$_3$)CH$_2$CH$_3$ |
| 56 | 5-(CH$_2$)$_8$CH$_3$ | 5-(CH$_2$)$_6$CH(CH$_3$)$_2$ | 5-(CH$_2$)$_5$CH(CH$_3$)CH$_2$CH$_3$ |
| 57 | 5-(CH$_2$)$_9$CH$_3$ | 5-(CH$_2$)$_7$CH(CH$_3$)$_2$ | 5-(CH$_2$)$_6$CH(CH$_3$)CH$_2$CH$_3$ |

TABLE 4-continued

|   | Column 1 | Column 2 | Column 3 |
|---|---|---|---|
| 58 | 5-$(CH_2)_{11}CH_3$ | 5-$(CH_2)_9CH(CH_3)_2$ | 5-$(CH_2)_8CH(CH_3)CH_2CH_3$ |
| 59 | 5-$(CH_2)_{15}CH_3$ | 5-$(CH_2)_{13}CH(CH_3)_2$ | 5-$(CH_2)_{12}CH(CH_3)CH_2CH_3$ |
| 60 | 6-$(CH_2)_{11}CH_3$ | 6-$(CH_2)_9CH(CH_3)_2$ | 6-$(CH_2)_8CH(CH_3)CH_2CH_3$ |
| | $Z = O, R^1 = 8\text{-F}, R^3 = 2'\text{-F}, R^4 = 6'\text{-F}, R^2 =$ | | |
| 61 | H | 5-(4-Cl—Ph) | 5-$CH_2CH{=}CH(CH_2)_6CH_3$ |
| 62 | 5-Cl | 5-(4-F—Ph) | 5-$CH_2CH{=}CH(CH_2)_2CH_3$ |
| 63 | 5-F | 5-$CH_2Ph$ | 5-$OCH_2CH{=}CH(CH_2)_6CH_3$ |
| 64 | 5-Br | 5-$CH_2CH_2Ph$ | 5-$OCH_2CH{=}CH(CH_2)_2CH_3$ |
| 65 | 5-$CF_3$ | 5-$CH_2Ph$-4-F | 5-$OCH_2Ph$-4-F |
| 66 | 5-Ph | 5-$CH_2Ph$-4-Cl | 5-$OCH_2CH_2Ph$-4-F |
| 67 | 5-Py | 5-$CH_2Ph$-4-$CF_3$ | 5-$CH_2C{\equiv}C$—$(CH_2)_4CH_3$ |
| 68 | 5-OPh | 5-(4-$CH_3(CH_2)_4Ph$) | 5-$OCH_2C{\equiv}C$—$(CH_2)_4CH_3$ |
| 69 | 5-SPh | 5-$CH_2Ph$-4-$(CH_2)_9CH_3$ | 5-$CH_2CH{=}CH$—$CH_2Ph$ |
| 70 | 5-OPy | 5-$CH_2Ph$-4-$(CH_2)_4CH_3$ | 5-$OCH_2CH{=}CH$—$CH_2Ph$ |
| 71 | 6-Cl | 6-(4-Cl—Ph) | 6-$CH_2CH{=}CH(CH_2)_6CH_3$ |
| 72 | 6-$CF_3$ | 6-$CH_2Ph$ | 6-$OCH_2CH{=}CH(CH_2)_6CH_3$ |
| 73 | 6-Ph | 6-$CH_2CH_2Ph$ | 6-$OCH_2CH{=}CH(CH_2)_2CH_3$ |
| 74 | 6-OPh | 6-$CH_2Ph$-4-$CF_3$ | 6-$CH_2C{\equiv}C$—$(CH_2)_4CH_3$ |
| 75 | 5-$O(CH_2)_5CH_3$ | 5-$O(CH_2)_3CH(CH_3)_2$ | 5-$O(CH_2)_2CH(CH_3)CH_2CH_3$ |
| 76 | 5-$O(CH_2)_6CH_3$ | 5-$O(CH_2)_4CH(CH_3)_2$ | 5-$O(CH_2)_3CH(CH_3)CH_2CH_3$ |
| 77 | 5-$O(CH_2)_7CH_3$ | 5-$O(CH_2)_5CH(CH_3)_2$ | 5-$O(CH_2)_4CH(CH_3)CH_2CH_3$ |
| 78 | 5-$O(CH_2)_8CH_3$ | 5-$O(CH_2)_6CH(CH_3)_2$ | 5-$O(CH_2)_5CH(CH_3)CH_2CH_3$ |
| 79 | 5-$O(CH_2)_9CH_3$ | 5-$O(CH_2)_7CH(CH_3)_2$ | 5-$O(CH_2)_6CH(CH_3)CH_2CH_3$ |
| 80 | 5-$O(CH_2)_{11}CH_3$ | 5-$O(CH_2)_9CH(CH_3)_2$ | 5-$O(CH_2)_8CH(CH_3)CH_2CH_3$ |
| 81 | 5-$O(CH_2)_{15}CH_3$ | 5-$O(CH_2)_{13}CH(CH_3)_2$ | 5-$O(CH_2)_{12}CH(CH_3)CH_2CH_3$ |
| 82 | 6-$O(CH_2)_{11}CH_3$ | 6-$O(CH_2)_9CH(CH_3)_2$ | 6-$O(CH_2)_8CH(CH_3)CH_2CH_3$ |
| 83 | 5-$(CH_2)_5CH_3$ | 5-$(CH_2)_3CH(CH_3)_2$ | 5-$(CH_2)_2CH(CH_3)CH_2CH_3$ |
| 84 | 5-$(CH_2)_6CH_3$ | 5-$(CH_2)_4CH(CH_3)_2$ | 5-$(CH_2)_3CH(CH_3)CH_2CH_3$ |
| 85 | 5-$(CH_2)_7CH_3$ | 5-$(CH_2)_5CH(CH_3)_2$ | 5-$(CH_2)_4CH(CH_3)CH_2CH_3$ |
| 86 | 5-$(CH_2)_8CH_3$ | 5-$(CH_2)_6CH(CH_3)_2$ | 5-$(CH_2)_5CH(CH_3)CH_2CH_3$ |
| 87 | 5-$(CH_2)_9CH_3$ | 5-$(CH_2)_7CH(CH_3)_2$ | 5-$(CH_2)_6CH(CH_3)CH_2CH_3$ |
| 88 | 5-$(CH_2)_{11}CH_3$ | 5-$(CH_2)_9CH(CH_3)_2$ | 5-$(CH_2)_8CH(CH_3)CH_2CH_3$ |
| 89 | 5-$(CH_2)_{15}CH_3$ | 5-$(CH_2)_{13}CH(CH_3)_2$ | 5-$(CH_2)_{12}CH(CH_3)CH_2CH_3$ |
| 90 | 6-$(CH_2)_{11}CH_3$ | 6-$(CH_2)_9CH(CH_3)_2$ | 6-$(CH_2)_8CH(CH_3)CH_2CH_3$ |

TABLE 5

|   | Column 1 | Column 2 | Column 3 |
|---|---|---|---|
| | $Z = O, R^1 = H, R^3 = 2'\text{-F}, R^4 = 6'\text{-F}, R^2 =$ | | |
| 1 | H | 5-(4-Cl—Ph) | 5-$CH_2CH{=}CH(CH_2)_6CH_3$ |
| 2 | 5-Cl | 5-(4-F—Ph) | 5-$CH_2CH{=}CH(CH_2)_2CH_3$ |
| 3 | 5-F | 5-$CH_2Ph$ | 5-$OCH_2CH{=}CH(CH_2)_6CH_3$ |
| 4 | 5-Br | 5-$CH_2CH_2Ph$ | 5-$OCH_2CH{=}CH(CH_2)_2CH_3$ |
| 5 | 5-$CF_3$ | 5-$CH_2Ph$-4-F | 5-$OCH_2Ph$-4-F |
| 6 | 5-Ph | 5-$CH_2Ph$-4-Cl | 5-$OCH_2CH_2Ph$-4-F |
| 7 | 5-Py | 5-$CH_2Ph$-4-$CF_3$ | 5-$CH_2C{\equiv}C$—$(CH_2)_4CH_3$ |
| 8 | 5-OPh | 5-(4-$CH_3(CH_2)_4Ph$) | 5-$OCH_2C{\equiv}C$—$(CH_2)_4CH_3$ |
| 9 | 5-SPh | 5-$CH_2Ph$-4-$(CH_2)_9CH_3$ | 5-$CH_2CH{=}CH$—$CH_2Ph$ |
| 10 | 5-OPy | 5-$CH_2Ph$-4-$(CH_2)_4CH_3$ | 5-$OCH_2CH{=}CH$—$CH_2Ph$ |
| 11 | 6-Cl | 6-(4-Cl—Ph) | 6-$CH_2CH{=}CH(CH_2)_6CH_3$ |
| 12 | 6-$CF_3$ | 6-$CH_2Ph$ | 6-$OCH_2CH{=}CH(CH_2)_6CH_3$ |
| 13 | 6-Ph | 6-$CH_2CH_2Ph$ | 6-$OCH_2CH{=}CH(CH_2)_2CH_3$ |
| 14 | 6-OPh | 6-$CH_2Ph$-4-$CF_3$ | 6-$CH_2C{\equiv}C$—$(CH_2)_4CH_3$ |
| 15 | 5-$O(CH_2)_5CH_3$ | 5-$O(CH_2)_3CH(CH_3)_2$ | 5-$O(CH_2)_2CH(CH_3)CH_2CH_3$ |
| 16 | 5-$O(CH_2)_6CH_3$ | 5-$O(CH_2)_4CH(CH_3)_2$ | 5-$O(CH_2)_3CH(CH_3)CH_2CH_3$ |
| 17 | 5-$O(CH_2)_7CH_3$ | 5-$O(CH_2)_5CH(CH_3)_2$ | 5-$O(CH_2)_4CH(CH_3)CH_2CH_3$ |
| 18 | 5-$O(CH_2)_8CH_3$ | 5-$O(CH_2)_6CH(CH_3)_2$ | 5-$O(CH_2)_5CH(CH_3)CH_2CH_3$ |
| 19 | 5-$O(CH_2)_9CH_3$ | 5-$O(CH_2)_7CH(CH_3)_2$ | 5-$O(CH_2)_6CH(CH_3)CH_2CH_3$ |
| 20 | 5-$O(CH_2)_{11}CH_3$ | 5-$O(CH_2)_9CH(CH_3)_2$ | 5-$O(CH_2)_8CH(CH_3)CH_2CH_3$ |
| 21 | 5-$O(CH_2)_{15}CH_3$ | 5-$O(CH_2)_{13}CH(CH_3)_2$ | 5-$O(CH_2)_{12}CH(CH_3)CH_2CH_3$ |
| 22 | 6-$O(CH_2)_{11}CH_3$ | 6-$O(CH_2)_9CH(CH_3)_2$ | 6-$O(CH_2)_8CH(CH_3)CH_2CH_3$ |
| 23 | 5-$(CH_2)_5CH_3$ | 5-$(CH_2)_3CH(CH_3)_2$ | 5-$(CH_2)_2CH(CH_3)CH_2CH_3$ |
| 24 | 5-$(CH_2)_6CH_3$ | 5-$(CH_2)_4CH(CH_3)_2$ | 5-$(CH_2)_3CH(CH_3)CH_2CH_3$ |
| 25 | 5-$(CH_2)_7CH_3$ | 5-$(CH_2)_5CH(CH_3)_2$ | 5-$(CH_2)_4CH(CH_3)CH_2CH_3$ |
| 26 | 5-$(CH_2)_8CH_3$ | 5-$(CH_2)_6CH(CH_3)_2$ | 5-$(CH_2)_5CH(CH_3)CH_2CH_3$ |
| 27 | 5-$(CH_2)_9CH_3$ | 5-$(CH_2)_7CH(CH_3)_2$ | 5-$(CH_2)_6CH(CH_3)CH_2CH_3$ |
| 28 | 5-$(CH_2)_{11}CH_3$ | 5-$(CH_2)_9CH(CH_3)_2$ | 5-$(CH_2)_8CH(CH_3)CH_2CH_3$ |
| 29 | 5-$(CH_2)_{15}CH_3$ | 5-$(CH_2)_{13}CH(CH_3)_2$ | 5-$(CH_2)_{12}CH(CH_3)CH_2CH_3$ |
| 30 | 6-$(CH_2)_{11}CH_3$ | 6-$(CH_2)_9CH(CH_3)_2$ | 6-$(CH_2)_8CH(CH_3)CH_2CH_3$ |
| | $Z = O, R^1 = 8\text{-Cl}, R^3 = 2'\text{-F}, R^4 = 6'\text{-F}, R^2 =$ | | |
| 31 | H | 5-(4-Cl—Ph) | 5-$CH_2CH{=}CH(CH_2)_6CH_3$ |
| 32 | 5-Cl | 5-(4-F—Ph) | 5-$CH_2CH{=}CH(CH_2)_2CH_3$ |
| 33 | 5-F | 5-$CH_2Ph$ | 5-$OCH_2CH{=}CH(CH_2)_6CH_3$ |
| 34 | 5-Br | 5-$CH_2CH_2Ph$ | 5-$OCH_2CH{=}CH(CH_2)_2CH_3$ |
| 35 | 5-$CF_3$ | 5-$CH_2Ph$-4-F | 5-$OCH_2Ph$-4-F |
| 36 | 5-Ph | 5-$CH_2Ph$-4-Cl | 5-$OCH_2CH_2Ph$-4-F |
| 37 | 5-Py | 5-$CH_2Ph$-4-$CF_3$ | 5-$CH_2C{\equiv}C$—$(CH_2)_4CH_3$ |
| 38 | 5-OPh | 5-(4-$CH_3(CH_2)_4Ph$) | 5-$OCH_2C{\equiv}C$—$(CH_2)_4CH_3$ |
| 39 | 5-SPh | 5-$CH_2Ph$-4-$(CH_2)_9CH_3$ | 5-$CH_2CH{=}CH$—$CH_2Ph$ |

TABLE 5-continued

| | Column 1 | Column 2 | Column 3 |
|---|---|---|---|
| 40 | 5-OPy | 5-CH$_2$Ph-4-(CH$_2$)$_4$CH$_3$ | 5-OCH$_2$CH=CH—CH$_2$Ph |
| 41 | 6-Cl | 6-(4-Cl—Ph) | 6-CH$_2$CH=CH(CH$_2$)$_6$CH$_3$ |
| 42 | 6-CF$_3$ | 6-CH$_2$Ph | 6-OCH$_2$CH=CH(CH$_2$)$_6$CH$_3$ |
| 43 | 6-Ph | 6-CH$_2$CH$_2$Ph | 6-OCH$_2$CH=CH(CH$_2$)$_2$CH$_3$ |
| 44 | 6-OPh | 6-CH$_2$Ph-4-CF$_3$ | 6-CH$_2$C≡C—(CH$_2$)$_4$CH$_3$ |
| 45 | 5-O(CH$_2$)$_5$CH$_3$ | 5-O(CH$_2$)$_3$CH(CH$_3$)$_2$ | 5-O(CH$_2$)$_2$CH(CH$_3$)CH$_2$CH$_3$ |
| 46 | 5-O(CH$_2$)$_6$CH$_3$ | 5-O(CH$_2$)$_4$CH(CH$_3$)$_2$ | 5-O(CH$_2$)$_3$CH(CH$_3$)CH$_2$CH$_3$ |
| 47 | 5-O(CH$_2$)$_7$CH$_3$ | 5-O(CH$_2$)$_5$CH(CH$_3$)$_2$ | 5-O(CH$_2$)$_4$CH(CH$_3$)CH$_2$CH$_3$ |
| 48 | 5-O(CH$_2$)$_8$CH$_3$ | 5-O(CH$_2$)$_6$CH(CH$_3$)$_2$ | 5-O(CH$_2$)$_5$CH(CH$_3$)CH$_2$CH$_3$ |
| 49 | 5-O(CH$_2$)$_9$CH$_3$ | 5-O(CH$_2$)$_7$CH(CH$_3$)$_2$ | 5-O(CH$_2$)$_6$CH(CH$_3$)CH$_2$CH$_3$ |
| 50 | 5-O(CH$_2$)$_{11}$CH$_3$ | 5-O(CH$_2$)$_9$CH(CH$_3$)$_2$ | 5-O(CH$_2$)$_8$CH(CH$_3$)CH$_2$CH$_3$ |
| 51 | 5-O(CH$_2$)$_{15}$CH$_3$ | 5-O(CH$_2$)$_{13}$CH(CH$_3$)$_2$ | 5-O(CH$_2$)$_{12}$CH(CH$_3$)CH$_2$CH$_3$ |
| 52 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 53 | 5-(CH$_2$)$_5$CH$_3$ | 5-(CH$_2$)$_3$CH(CH$_3$)$_2$ | 5-(CH$_2$)$_2$CH(CH$_3$)CH$_2$CH$_3$ |
| 54 | 5-(CH$_2$)$_6$CH$_3$ | 5-(CH$_2$)$_4$CH(CH$_3$)$_2$ | 5-(CH$_2$)$_3$CH(CH$_3$)CH$_2$CH$_3$ |
| 55 | 5-(CH$_2$)$_7$CH$_3$ | 5-(CH$_2$)$_5$CH(CH$_3$)$_2$ | 5-(CH$_2$)$_4$CH(CH$_3$)CH$_2$CH$_3$ |
| 56 | 5-(CH$_2$)$_8$CH$_3$ | 5-(CH$_2$)$_6$CH(CH$_3$)$_2$ | 5-(CH$_2$)$_5$CH(CH$_3$)CH$_2$CH$_3$ |
| 57 | 5-(CH$_2$)$_9$CH$_3$ | 5-(CH$_2$)$_7$CH(CH$_3$)$_2$ | 5-(CH$_2$)$_6$CH(CH$_3$)CH$_2$CH$_3$ |
| 58 | 5-(CH$_2$)$_{11}$CH$_3$ | 5-(CH$_2$)$_9$CH(CH$_3$)$_2$ | 5-(CH$_2$)$_8$CH(CH$_3$)CH$_2$CH$_3$ |
| 59 | 5-(CH$_2$)$_{15}$CH$_3$ | 5-(CH$_2$)$_{13}$CH(CH$_3$)$_2$ | 5-(CH$_2$)$_{12}$CH(CH$_3$)CH$_2$CH$_3$ |
| 60 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| | \multicolumn{3}{c}{Z = O, R$^1$ = 8-F, R$^3$ = 2'-F, R$^4$ = 6'-F, R$^2$ =} | | |
| 61 | H | 5-(4-Cl—Ph) | 5-CH$_2$CH=CH(CH$_2$)$_6$CH$_3$ |
| 62 | 5-Cl | 5-(4-F—Ph) | 5-CH$_2$CH=CH(CH$_2$)$_2$CH$_3$ |
| 63 | 5-F | 5-CH$_2$Ph | 5-OCH$_2$CH=CH(CH$_2$)$_6$CH$_3$ |
| 64 | 5-Br | 5-CH$_2$CH$_2$Ph | 5-OCH$_2$CH=CH(CH$_2$)$_2$CH$_3$ |
| 65 | 5-CF$_3$ | 5-CH$_2$Ph-4-F | 5-OCH$_2$Ph-4-F |
| 66 | 5-Ph | 5-CH$_2$Ph-4-Cl | 5-OCH$_2$CH$_2$Ph-4-F |
| 67 | 5-Py | 5-CH$_2$Ph-4-CF$_3$ | 5-CH$_2$C≡C—(CH$_2$)$_4$CH$_3$ |
| 68 | 5-OPh | 5-(4-CH$_3$(CH$_2$)$_4$Ph) | 5-OCH$_2$C≡C—(CH$_2$)$_4$CH$_3$ |
| 69 | 5-SPh | 5-CH$_2$Ph-4-(CH$_2$)$_9$CH$_3$ | 5-CH$_2$CH=CH—CH$_2$Ph |
| 70 | 5-OPy | 5-CH$_2$Ph-4-(CH$_2$)$_4$CH$_3$ | 5-OCH$_2$CH=CH—CH$_2$Ph |
| 71 | 6-Cl | 6-(4-Cl—Ph) | 6-CH$_2$CH=CH(CH$_2$)$_6$CH$_3$ |
| 72 | 6-CF$_3$ | 6-CH$_2$Ph | 6-OCH$_2$CH=CH(CH$_2$)$_6$CH$_3$ |
| 73 | 6-Ph | 6-CH$_2$CH$_2$Ph | 6-OCH$_2$CH=CH(CH$_2$)$_2$CH$_3$ |
| 74 | 6-OPh | 6-CH$_2$Ph-4-CF$_3$ | 6-CH$_2$C≡C—(CH$_2$)$_4$CH$_3$ |
| 75 | 5-O(CH$_2$)$_5$CH$_3$ | 5-O(CH$_2$)$_3$CH(CH$_3$)$_2$ | 5-O(CH$_2$)$_2$CH(CH$_3$)CH$_2$CH$_3$ |
| 76 | 5-O(CH$_2$)$_6$CH$_3$ | 5-O(CH$_2$)$_4$CH(CH$_3$)$_2$ | 5-O(CH$_2$)$_3$CH(CH$_3$)CH$_2$CH$_3$ |
| 77 | 5-O(CH$_2$)$_7$CH$_3$ | 5-O(CH$_2$)$_5$CH(CH$_3$)$_2$ | 5-O(CH$_2$)$_4$CH(CH$_3$)CH$_2$CH$_3$ |
| 78 | 5-O(CH$_2$)$_8$CH$_3$ | 5-O(CH$_2$)$_6$CH(CH$_3$)$_2$ | 5-O(CH$_2$)$_5$CH(CH$_3$)CH$_2$CH$_3$ |
| 79 | 5-O(CH$_2$)$_9$CH$_3$ | 5-O(CH$_2$)$_7$CH(CH$_3$)$_2$ | 5-O(CH$_2$)$_6$CH(CH$_3$)CH$_2$CH$_3$ |
| 80 | 5-O(CH$_2$)$_{11}$CH$_3$ | 5-O(CH$_2$)$_9$CH(CH$_3$)$_2$ | 5-O(CH$_2$)$_8$CH(CH$_3$)CH$_2$CH$_3$ |
| 81 | 5-O(CH$_2$)$_{15}$CH$_3$ | 5-O(CH$_2$)$_{13}$CH(CH$_3$)$_2$ | 5-O(CH$_2$)$_{12}$CH(CH$_3$)CH$_2$CH$_3$ |
| 82 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 83 | 5-(CH$_2$)$_5$CH$_3$ | 5-(CH$_2$)$_3$CH(CH$_3$)$_2$ | 5-(CH$_2$)$_2$CH(CH$_3$)CH$_2$CH$_3$ |
| 84 | 5-(CH$_2$)$_6$CH$_3$ | 5-(CH$_2$)$_4$CH(CH$_3$)$_2$ | 5-(CH$_2$)$_3$CH(CH$_3$)CH$_2$CH$_3$ |
| 85 | 5-(CH$_2$)$_7$CH$_3$ | 5-(CH$_2$)$_5$CH(CH$_3$)$_2$ | 5-(CH$_2$)$_4$CH(CH$_3$)CH$_2$CH$_3$ |
| 86 | 5-(CH$_2$)$_8$CH$_3$ | 5-(CH$_2$)$_6$CH(CH$_3$)$_2$ | 5-(CH$_2$)$_5$CH(CH$_3$)CH$_2$CH$_3$ |
| 87 | 5-(CH$_2$)$_9$CH$_3$ | 5-(CH$_2$)$_7$CH(CH$_3$)$_2$ | 5-(CH$_2$)$_6$CH(CH$_3$)CH$_2$CH$_3$ |
| 88 | 5-(CH$_2$)$_{11}$CH$_3$ | 5-(CH$_2$)$_9$CH(CH$_3$)$_2$ | 5-(CH$_2$)$_8$CH(CH$_3$)CH$_2$CH$_3$ |
| 89 | 5-(CH$_2$)$_{15}$CH$_3$ | 5-(CH$_2$)$_{13}$CH(CH$_3$)$_2$ | 5-(CH$_2$)$_{12}$CH(CH$_3$)CH$_2$CH$_3$ |
| 90 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |

TABLE 6

| | Column 1 | Column 2 | Column 3 |
|---|---|---|---|
| | | Z = O, R$^1$ = H, R$^3$ = 2'-F, R$^4$ = 6'-F, R$^2$ = | |
| 1 | H | 5-(4-Cl—Ph) | 5-CH$_2$CH=CH(CH$_2$)$_6$CH$_3$ |
| 2 | 5-Cl | 5-(4-F—Ph) | 5-CH$_2$CH=CH(CH$_2$)$_2$CH$_3$ |
| 3 | 5-F | 5-CH$_2$Ph | 5-OCH$_2$CH=CH(CH$_2$)$_6$CH$_3$ |
| 4 | 5-Br | 5-CH$_2$CH$_2$Ph | 5-OCH$_2$CH=CH(CH$_2$)$_2$CH$_3$ |
| 5 | 5-CF$_3$ | 5-CH$_2$Ph-4-F | 5-OCH$_2$Ph-4-F |
| 6 | 5-Ph | 5-CH$_2$Ph-4-Cl | 5-OCH$_2$CH$_2$Ph-4-F |
| 7 | 5-Py | 5-CH$_2$Ph-4-CF$_3$ | 5-CH$_2$C≡C—(CH$_2$)$_4$CH$_3$ |
| 8 | 5-OPh | 5-(4-CH$_3$(CH$_2$)$_4$Ph) | 5-OCH$_2$C≡C—(CH$_2$)$_4$CH$_3$ |
| 9 | 5-SPh | 5-CH$_2$Ph-4-(CH$_2$)$_9$CH$_3$ | 5-CH$_2$CH=CH—CH$_2$Ph |
| 10 | 5-OPy | 5-CH$_2$Ph-4-(CH$_2$)$_4$CH$_3$ | 5-OCH$_2$CH=CH—CH$_2$Ph |
| 11 | 6-Cl | 6-(4-Cl—Ph) | 6-CH$_2$CH=CH(CH$_2$)$_6$CH$_3$ |
| 12 | 6-CF$_3$ | 6-CH$_2$Ph | 6-OCH$_2$CH=CH(CH$_2$)$_6$CH$_3$ |
| 13 | 6-Ph | 6-CH$_2$CH$_2$Ph | 6-OCH$_2$CH=CH(CH$_2$)$_2$CH$_3$ |
| 14 | 6-OPh | 6-CH$_2$Ph-4-CF$_3$ | 6-CH$_2$C≡C—(CH$_2$)$_4$CH$_3$ |
| 15 | 5-O(CH$_2$)$_5$CH$_3$ | 5-O(CH$_2$)$_3$CH(CH$_3$)$_2$ | 5-O(CH$_2$)$_2$CH(CH$_3$)CH$_2$CH$_3$ |
| 16 | 5-O(CH$_2$)$_6$CH$_3$ | 5-O(CH$_2$)$_4$CH(CH$_3$)$_2$ | 5-O(CH$_2$)$_3$CH(CH$_3$)CH$_2$CH$_3$ |
| 17 | 5-O(CH$_2$)$_7$CH$_3$ | 5-O(CH$_2$)$_5$CH(CH$_3$)$_2$ | 5-O(CH$_2$)$_4$CH(CH$_3$)CH$_2$CH$_3$ |
| 18 | 5-O(CH$_2$)$_8$CH$_3$ | 5-O(CH$_2$)$_6$CH(CH$_3$)$_2$ | 5-O(CH$_2$)$_5$CH(CH$_3$)CH$_2$CH$_3$ |
| 19 | 5-O(CH$_2$)$_9$CH$_3$ | 5-O(CH$_2$)$_7$CH(CH$_3$)$_2$ | 5-O(CH$_2$)$_6$CH(CH$_3$)CH$_2$CH$_3$ |
| 20 | 5-O(CH$_2$)$_{11}$CH$_3$ | 5-O(CH$_2$)$_9$CH(CH$_3$)$_2$ | 5-O(CH$_2$)$_8$CH(CH$_3$)CH$_2$CH$_3$ |
| 21 | 5-O(CH$_2$)$_{15}$CH$_3$ | 5-O(CH$_2$)$_{13}$CH(CH$_3$)$_2$ | 5-O(CH$_2$)$_{12}$CH(CH$_3$)CH$_2$CH$_3$ |
| 22 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |

TABLE 6-continued

| | Column 1 | Column 2 | Column 3 |
|---|---|---|---|
| 23 | 5-(CH$_2$)$_5$CH$_3$ | 5-(CH$_2$)$_3$CH(CH$_3$)$_2$ | 5-(CH$_2$)$_2$CH(CH$_3$)CH$_2$CH$_3$ |
| 24 | 5-(CH$_2$)$_6$CH$_3$ | 5-(CH$_2$)$_4$CH(CH$_3$)$_2$ | 5-(CH$_2$)$_3$CH(CH$_3$)CH$_2$CH$_3$ |
| 25 | 5-(CH$_2$)$_7$CH$_3$ | 5-(CH$_2$)$_5$CH(CH$_3$)$_2$ | 5-(CH$_2$)$_4$CH(CH$_3$)CH$_2$CH$_3$ |
| 26 | 5-(CH$_2$)$_8$CH$_3$ | 5-(CH$_2$)$_6$CH(CH$_3$)$_2$ | 5-(CH$_2$)$_5$CH(CH$_3$)CH$_2$CH$_3$ |
| 27 | 5-(CH$_2$)$_9$CH$_3$ | 5-(CH$_2$)$_7$CH(CH$_3$)$_2$ | 5-(CH$_2$)$_6$CH(CH$_3$)CH$_2$CH$_3$ |
| 28 | 5-(CH$_2$)$_{11}$CH$_3$ | 5-(CH$_2$)$_9$CH(CH$_3$)$_2$ | 5-(CH$_2$)$_8$CH(CH$_3$)CH$_2$CH$_3$ |
| 29 | 5-(CH$_2$)$_{15}$CH$_3$ | 5-(CH$_2$)$_{13}$CH(CH$_3$)$_2$ | 5-(CH$_2$)$_{12}$CH(CH$_3$)CH$_2$CH$_3$ |
| 30 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| | $Z = O, R^1 = H, R^3 = 2'$-F, $R^4 = 6'$-Cl, $R^2 =$ | | |
| 31 | H | 5-(4-Cl—Ph) | 5-CH$_2$CH=CH(CH$_2$)$_6$CH$_3$ |
| 32 | 5-Cl | 5-(4-F—Ph) | 5-CH$_2$CH=CH(CH$_2$)$_2$CH$_3$ |
| 33 | 5-F | 5-CH$_2$Ph | 5-OCH$_2$CH=CH(CH$_2$)$_6$CH$_3$ |
| 34 | 5-Br | 5-CH$_2$CH$_2$Ph | 5-OCH$_2$CH=CH(CH$_2$)$_2$CH$_3$ |
| 35 | 5-CF$_3$ | 5-CH$_2$Ph-4-F | 5-OCH$_2$Ph-4-F |
| 36 | 5-Ph | 5-CH$_2$Ph-4-Cl | 5-OCH$_2$CH$_2$Ph-4-F |
| 37 | 5-Py | 5-CH$_2$Ph-4-CF$_3$ | 5-CH$_2$C≡C—(CH$_2$)$_4$CH$_3$ |
| 38 | 5-OPh | 5-(4-CH$_3$(CH$_2$)$_4$Ph) | 5-OCH$_2$C≡C—(CH$_2$)$_4$CH$_3$ |
| 39 | 5-SPh | 5-CH$_2$Ph-4-(CH$_2$)$_9$CH$_3$ | 5-CH$_2$CH=CH—CH$_2$Ph |
| 40 | 5-OPy | 5-CH$_2$Ph-4-(CH$_2$)$_4$CH$_3$ | 5-OCH$_2$CH=CH—CH$_2$Ph |
| 41 | 6-Cl | 6-(4-Cl—Ph) | 6-CH$_2$CH=CH(CH$_2$)$_6$CH$_3$ |
| 42 | 6-CF$_3$ | 6-CH$_2$Ph | 6-OCH$_2$CH=CH(CH$_2$)$_6$CH$_3$ |
| 43 | 6-Ph | 6-CH$_2$CH$_2$Ph | 6-OCH$_2$CH=CH(CH$_2$)$_2$CH$_3$ |
| 44 | 6-OPh | 6-CH$_2$Ph-4-CF$_3$ | 6-CH$_2$C≡C—(CH$_2$)$_4$CH$_3$ |
| 45 | 5-O(CH$_2$)$_5$CH$_3$ | 5-O(CH$_2$)$_3$CH(CH$_3$)$_2$ | 5-O(CH$_2$)$_2$CH(CH$_3$)CH$_2$CH$_3$ |
| 46 | 5-O(CH$_2$)$_6$CH$_3$ | 5-O(CH$_2$)$_4$CH(CH$_3$)$_2$ | 5-O(CH$_2$)$_3$CH(CH$_3$)CH$_2$CH$_3$ |
| 47 | 5-O(CH$_2$)$_7$CH$_3$ | 5-O(CH$_2$)$_5$CH(CH$_3$)$_2$ | 5-O(CH$_2$)$_4$CH(CH$_3$)CH$_2$CH$_3$ |
| 48 | 5-O(CH$_2$)$_8$CH$_3$ | 5-O(CH$_2$)$_6$CH(CH$_3$)$_2$ | 5-O(CH$_2$)$_5$CH(CH$_3$)CH$_2$CH$_3$ |
| 49 | 5-O(CH$_2$)$_9$CH$_3$ | 5-O(CH$_2$)$_7$CH(CH$_3$)$_2$ | 5-O(CH$_2$)$_6$CH(CH$_3$)CH$_2$CH$_3$ |
| 50 | 5-O(CH$_2$)$_{11}$CH$_3$ | 5-O(CH$_2$)$_9$CH(CH$_3$)$_2$ | 5-O(CH$_2$)$_8$CH(CH$_3$)CH$_2$CH$_3$ |
| 51 | 5-O(CH$_2$)$_{15}$CH$_3$ | 5-O(CH$_2$)$_{13}$CH(CH$_3$)$_2$ | 5-O(CH$_2$)$_{12}$CH(CH$_3$)CH$_2$CH$_3$ |
| 52 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 53 | 5-(CH$_2$)$_5$CH$_3$ | 5-(CH$_2$)$_3$CH(CH$_3$)$_2$ | 5-(CH$_2$)$_2$CH(CH$_3$)CH$_2$CH$_3$ |
| 54 | 5-(CH$_2$)$_6$CH$_3$ | 5-(CH$_2$)$_4$CH(CH$_3$)$_2$ | 5-(CH$_2$)$_3$CH(CH$_3$)CH$_2$CH$_3$ |
| 55 | 5-(CH$_2$)$_7$CH$_3$ | 5-(CH$_2$)$_5$CH(CH$_3$)$_2$ | 5-(CH$_2$)$_4$CH(CH$_3$)CH$_2$CH$_3$ |
| 56 | 5-(CH$_2$)$_8$CH$_3$ | 5-(CH$_2$)$_6$CH(CH$_3$)$_2$ | 5-(CH$_2$)$_5$CH(CH$_3$)CH$_2$CH$_3$ |
| 57 | 5-(CH$_2$)$_9$CH$_3$ | 5-(CH$_2$)$_7$CH(CH$_3$)$_2$ | 5-(CH$_2$)$_6$CH(CH$_3$)CH$_2$CH$_3$ |
| 58 | 5-(CH$_2$)$_{11}$CH$_3$ | 5-(CH$_2$)$_9$CH(CH$_3$)$_2$ | 5-(CH$_2$)$_8$CH(CH$_3$)CH$_2$CH$_3$ |
| 59 | 5-(CH$_2$)$_{15}$CH$_3$ | 5-(CH$_2$)$_{13}$CH(CH$_3$)$_2$ | 5-(CH$_2$)$_{12}$CH(CH$_3$)CH$_2$CH$_3$ |
| 60 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| | $Z = O, R^1 = 8$-Cl, $R^3 = 2'$-F, $R^4 = 6'$-F, $R^2 =$ | | |
| 61 | H | 5-(4-Cl—Ph) | 5-CH$_2$CH=CH(CH$_2$)$_6$CH$_3$ |
| 62 | 5-Cl | 5-(4-F—Ph) | 5-CH$_2$CH=CH(CH$_2$)$_2$CH$_3$ |
| 63 | 5-F | 5-CH$_2$Ph | 5-OCH$_2$CH=CH(CH$_2$)$_6$CH$_3$ |
| 64 | 5-Br | 5-CH$_2$CH$_2$Ph | 5-OCH$_2$CH=CH(CH$_2$)$_2$CH$_3$ |
| 65 | 5-CF$_3$ | 5-CH$_2$Ph-4-F | 5-OCH$_2$Ph-4-F |
| 66 | 5-Ph | 5-CH$_2$Ph-4-Cl | 5-OCH$_2$CH$_2$Ph-4-F |
| 67 | 5-Py | 5-CH$_2$Ph-4-CF$_3$ | 5-CH$_2$C≡C—(CH$_2$)$_4$CH$_3$ |
| 68 | 5-OPh | 5-(4-CH$_3$(CH$_2$)$_4$Ph) | 5-OCH$_2$C≡C—(CH$_2$)$_4$CH$_3$ |
| 69 | 5-SPh | 5-CH$_2$Ph-4-(CH$_2$)$_9$CH$_3$ | 5-CH$_2$CH=CH—CH$_2$Ph |
| 70 | 5-OPy | 5-CH$_2$Ph-4-(CH$_2$)$_4$CH$_3$ | 5-OCH$_2$CH=CH—CH$_2$Ph |
| 71 | 6-Cl | 6-(4-Cl—Ph) | 6-CH$_2$CH=CH(CH$_2$)$_6$CH$_3$ |
| 72 | 6-CF$_3$ | 6-CH$_2$Ph | 6-OCH$_2$CH=CH(CH$_2$)$_6$CH$_3$ |
| 73 | 6-Ph | 6-CH$_2$CH$_2$Ph | 6-OCH$_2$CH=CH(CH$_2$)$_2$CH$_3$ |
| 74 | 6-OPh | 6-CH$_2$Ph-4-CF$_3$ | 6-CH$_2$C≡C—(CH$_2$)$_4$CH$_3$ |
| 75 | 5-O(CH$_2$)$_5$CH$_3$ | 5-O(CH$_2$)$_3$CH(CH$_3$)$_2$ | 5-O(CH$_2$)$_2$CH(CH$_3$)CH$_2$CH$_3$ |
| 76 | 5-O(CH$_2$)$_6$CH$_3$ | 5-O(CH$_2$)$_4$CH(CH$_3$)$_2$ | 5-O(CH$_2$)$_3$CH(CH$_3$)CH$_2$CH$_3$ |
| 77 | 5-O(CH$_2$)$_7$CH$_3$ | 5-O(CH$_2$)$_5$CH(CH$_3$)$_2$ | 5-O(CH$_2$)$_4$CH(CH$_3$)CH$_2$CH$_3$ |
| 78 | 5-O(CH$_2$)$_8$CH$_3$ | 5-O(CH$_2$)$_6$CH(CH$_3$)$_2$ | 5-O(CH$_2$)$_5$CH(CH$_3$)CH$_2$CH$_3$ |
| 79 | 5-O(CH$_2$)$_9$CH$_3$ | 5-O(CH$_2$)$_7$CH(CH$_3$)$_2$ | 5-O(CH$_2$)$_6$CH(CH$_3$)CH$_2$CH$_3$ |
| 80 | 5-O(CH$_2$)$_{11}$CH$_3$ | 5-O(CH$_2$)$_9$CH(CH$_3$)$_2$ | 5-O(CH$_2$)$_8$CH(CH$_3$)CH$_2$CH$_3$ |
| 81 | 5-O(CH$_2$)$_{15}$CH$_3$ | 5-O(CH$_2$)$_{13}$CH(CH$_3$)$_2$ | 5-O(CH$_2$)$_{12}$CH(CH$_3$)CH$_2$CH$_3$ |
| 82 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 83 | 5-(CH$_2$)$_5$CH$_3$ | 5-(CH$_2$)$_3$CH(CH$_3$)$_2$ | 5-(CH$_2$)$_2$CH(CH$_3$)CH$_2$CH$_3$ |
| 84 | 5-(CH$_2$)$_6$CH$_3$ | 5-(CH$_2$)$_4$CH(CH$_3$)$_2$ | 5-(CH$_2$)$_3$CH(CH$_3$)CH$_2$CH$_3$ |
| 85 | 5-(CH$_2$)$_7$CH$_3$ | 5-(CH$_2$)$_5$CH(CH$_3$)$_2$ | 5-(CH$_2$)$_4$CH(CH$_3$)CH$_2$CH$_3$ |
| 86 | 5-(CH$_2$)$_8$CH$_3$ | 5-(CH$_2$)$_6$CH(CH$_3$)$_2$ | 5-(CH$_2$)$_5$CH(CH$_3$)CH$_2$CH$_3$ |
| 87 | 5-(CH$_2$)$_9$CH$_3$ | 5-(CH$_2$)$_7$CH(CH$_3$)$_2$ | 5-(CH$_2$)$_6$CH(CH$_3$)CH$_2$CH$_3$ |
| 88 | 5-(CH$_2$)$_{11}$CH$_3$ | 5-(CH$_2$)$_9$CH(CH$_3$)$_2$ | 5-(CH$_2$)$_8$CH(CH$_3$)CH$_2$CH$_3$ |
| 89 | 5-(CH$_2$)$_{15}$CH$_3$ | 5-(CH$_2$)$_{13}$CH(CH$_3$)$_2$ | 5-(CH$_2$)$_{12}$CH(CH$_3$)CH$_2$CH$_3$ |
| 90 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| | $Z = O, R^1 = 8$-F, $R^3 = 2'$-F, $R^4 = 6'$-F, $R^2 =$ | | |
| 91 | H | 5-(4-Cl—Ph) | 5-CH$_2$CH=CH(CH$_2$)$_6$CH$_3$ |
| 92 | 5-Cl | 5-(4-F—Ph) | 5-CH$_2$CH=CH(CH$_2$)$_2$CH$_3$ |
| 93 | 5-F | 5-CH$_2$Ph | 5-OCH$_2$CH=CH(CH$_2$)$_6$CH$_3$ |
| 94 | 5-Br | 5-CH$_2$CH$_2$Ph | 5-OCH$_2$CH=CH(CH$_2$)$_2$CH$_3$ |
| 95 | 5-CF$_3$ | 5-CH$_2$Ph-4-F | 5-OCH$_2$Ph-4-F |
| 96 | 5-Ph | 5-CH$_2$Ph-4-Cl | 5-OCH$_2$CH$_2$Ph-4-F |
| 97 | 5-Py | 5-CH$_2$Ph-4-CF$_3$ | 5-CH$_2$C≡C—(CH$_2$)$_4$CH$_3$ |
| 98 | 5-OPh | 5-(4-CH$_3$(CH$_2$)$_4$Ph) | 5-OCH$_2$C≡C—(CH$_2$)$_4$CH$_3$ |
| 99 | 5-SPh | 5-CH$_2$Ph-4-(CH$_2$)$_9$CH$_3$ | 5-CH$_2$CH=CH—CH$_2$Ph |

TABLE 6-continued

|     | Column 1 | Column 2 | Column 3 |
|-----|----------|----------|----------|
| 100 | 5-OPy | 5-CH$_2$Ph-4-(CH$_2$)$_4$CH$_3$ | 5-OCH$_2$CH=CH—CH$_2$Ph |
| 101 | 6-Cl | 6-(4-Cl—Ph) | 6-CH$_2$CH=CH(CH$_2$)$_6$CH$_3$ |
| 102 | 6-CF$_3$ | 6-CH$_2$Ph | 6-OCH$_2$CH=CH(CH$_2$)$_6$CH$_3$ |
| 103 | 6-Ph | 6-CH$_2$CH$_2$Ph | 6-OCH$_2$CH—CH(CH$_2$)$_2$CH$_3$ |
| 104 | 6-OPh | 6-CH$_2$Ph-4-CF$_3$ | 6-CH$_2$C≡C—(CH$_2$)$_4$CH$_3$ |
| 105 | 5-O(CH$_2$)$_5$CH$_3$ | 5-O(CH$_2$)$_3$CH(CH$_3$)$_2$ | 5-O(CH$_2$)$_2$CH(CH$_3$)CH$_2$CH$_3$ |
| 106 | 5-O(CH$_2$)$_6$CH$_3$ | 5-O(CH$_2$)$_4$CH(CH$_3$)$_2$ | 5-O(CH$_2$)$_3$CH(CH$_3$)CH$_2$CH$_3$ |
| 107 | 5-O(CH$_2$)$_7$CH$_3$ | 5-O(CH$_2$)$_5$CH(CH$_3$)$_2$ | 5-O(CH$_2$)$_4$CH(CH$_3$)CH$_2$CH$_3$ |
| 108 | 5-O(CH$_2$)$_8$CH$_3$ | 5-O(CH$_2$)$_6$CH(CH$_3$)$_2$ | 5-O(CH$_2$)$_5$CH(CH$_3$)CH$_2$CH$_3$ |
| 109 | 5-O(CH$_2$)$_9$CH$_3$ | 5-O(CH$_2$)$_7$CH(CH$_3$)$_2$ | 5-O(CH$_2$)$_6$CH(CH$_3$)CH$_2$CH$_3$ |
| 110 | 5-O(CH$_2$)$_{11}$CH$_3$ | 5-O(CH$_2$)$_9$CH(CH$_3$)$_2$ | 5-O(CH$_2$)$_8$CH(CH$_3$)CH$_2$CH$_3$ |
| 111 | 5-O(CH$_2$)$_{15}$CH$_3$ | 5-O(CH$_2$)$_{13}$CH(CH$_3$)$_2$ | 5-O(CH$_2$)$_{12}$CH(CH$_3$)CH$_2$CH$_3$ |
| 112 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 113 | 5-(CH$_2$)$_5$CH$_3$ | 5-(CH$_2$)$_3$CH(CH$_3$)$_2$ | 5-(CH$_2$)$_2$CH(CH$_3$)CH$_2$CH$_3$ |
| 114 | 5-(CH$_2$)$_6$CH$_3$ | 5-(CH$_2$)$_4$CH(CH$_3$)$_2$ | 5-(CH$_2$)$_3$CH(CH$_3$)CH$_2$CH$_3$ |
| 115 | 5-(CH$_2$)$_7$CH$_3$ | 5-(CH$_2$)$_5$CH(CH$_3$)$_2$ | 5-(CH$_2$)$_4$CH(CH$_3$)CH$_2$CH$_3$ |
| 116 | 5-(CH$_2$)$_8$CH$_3$ | 5-(CH$_2$)$_6$CH(CH$_3$)$_2$ | 5-(CH$_2$)$_5$CH(CH$_3$)CH$_2$CH$_3$ |
| 117 | 5-(CH$_2$)$_9$CH$_3$ | 5-(CH$_2$)$_7$CH(CH$_3$)$_2$ | 5-(CH$_2$)$_6$CH(CH$_3$)CH$_2$CH$_3$ |
| 118 | 5-(CH$_2$)$_{11}$CH$_3$ | 5-(CH$_2$)$_9$CH(CH$_3$)$_2$ | 5-(CH$_2$)$_8$CH(CH$_3$)CH$_2$CH$_3$ |
| 119 | 5-(CH$_2$)$_{15}$CH$_3$ | 5-(CH$_2$)$_{13}$CH(CH$_3$)$_2$ | 5-(CH$_2$)$_{12}$CH(CH$_3$)CH$_2$CH$_3$ |
| 120 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |
| | Z = O, R$^1$ = 8-F, R$^3$ = 2'-F, R$^4$ = 6'-Cl, R$^2$ = | | |
| 121 | H | 5-(4-Cl—Ph) | 5-CH$_2$CH=CH(CH$_2$)$_6$CH$_3$ |
| 122 | 5-Cl | 5-(4-F—Ph) | 5-CH$_2$CH=CH(CH$_2$)$_2$CH$_3$ |
| 123 | 5-F | 5-CH$_2$Ph | 5-OCH$_2$CH=CH(CH$_2$)$_6$CH$_3$ |
| 124 | 5-Br | 5-CH$_2$CH$_2$Ph | 5-OCH$_2$CH=CH(CH$_2$)$_2$CH$_3$ |
| 125 | 5-CF$_3$ | 5-CH$_2$Ph-4-F | 5-OCH$_2$Ph-4-F |
| 126 | 5-Ph | 5-CH$_2$Ph-4-Cl | 5-OCH$_2$CH$_2$Ph-4-F |
| 127 | 5-Py | 5-CH$_2$Ph-4-CF$_3$ | 5-CH$_2$C≡C—(CH$_2$)$_4$CH$_3$ |
| 128 | 5-OPh | 5-(4-CH$_3$(CH$_2$)$_4$Ph) | 5-OCH$_2$C≡C—(CH$_2$)$_4$CH$_3$ |
| 129 | 5-SPh | 5-CH$_2$Ph-4-(CH$_2$)$_9$CH$_3$ | 5-CH$_2$CH=CH—CH$_2$Ph |
| 130 | 5-OPy | 5-CH$_2$Ph-4-(CH$_2$)$_4$CH$_3$ | 5-OCH$_2$CH=CH—CH$_2$Ph |
| 131 | 6-Cl | 6-(4-Cl—Ph) | 6-CH$_2$CH=CH(CH$_2$)$_6$CH$_3$ |
| 132 | 6-CF$_3$ | 6-CH$_2$Ph | 6-OCH$_2$CH=CH(CH$_2$)$_6$CH$_3$ |
| 133 | 6-Ph | 6-CH$_2$CH$_2$Ph | 6-OCH$_2$CH—CH(CH$_2$)$_2$CH$_3$ |
| 134 | 6-OPh | 6-CH$_2$Ph-4-CF$_3$ | 6-CH$_2$C≡C—(CH$_2$)$_4$CH$_3$ |
| 135 | 5-O(CH$_2$)$_5$CH$_3$ | 5-O(CH$_2$)$_3$CH(CH$_3$)$_2$ | 5-O(CH$_2$)$_2$CH(CH$_3$)CH$_2$CH$_3$ |
| 136 | 5-O(CH$_2$)$_6$CH$_3$ | 5-O(CH$_2$)$_4$CH(CH$_3$)$_2$ | 5-O(CH$_2$)$_3$CH(CH$_3$)CH$_2$CH$_3$ |
| 137 | 5-O(CH$_2$)$_7$CH$_3$ | 5-O(CH$_2$)$_5$CH(CH$_3$)$_2$ | 5-O(CH$_2$)$_4$CH(CH$_3$)CH$_2$CH$_3$ |
| 138 | 5-O(CH$_2$)$_8$CH$_3$ | 5-O(CH$_2$)$_6$CH(CH$_3$)$_2$ | 5-O(CH$_2$)$_5$CH(CH$_3$)CH$_2$CH$_3$ |
| 139 | 5-O(CH$_2$)$_9$CH$_3$ | 5-O(CH$_2$)$_7$CH(CH$_3$)$_2$ | 5-O(CH$_2$)$_6$CH(CH$_3$)CH$_2$CH$_3$ |
| 140 | 5-O(CH$_2$)$_{11}$CH$_3$ | 5-O(CH$_2$)$_9$CH(CH$_3$)$_2$ | 5-O(CH$_2$)$_8$CH(CH$_3$)CH$_2$CH$_3$ |
| 141 | 5-O(CH$_2$)$_{15}$CH$_3$ | 5-O(CH$_2$)$_{13}$CH(CH$_3$)$_2$ | 5-O(CH$_2$)$_{12}$CH(CH$_3$)CH$_2$CH$_3$ |
| 142 | 6-O(CH$_2$)$_{11}$CH$_3$ | 6-O(CH$_2$)$_9$CH(CH$_3$)$_2$ | 6-O(CH$_2$)$_8$CH(CH$_3$)CH$_2$CH$_3$ |
| 143 | 5-(CH$_2$)$_5$CH$_3$ | 5-(CH$_2$)$_3$CH(CH$_3$)$_2$ | 5-(CH$_2$)$_2$CH(CH$_3$)CH$_2$CH$_3$ |
| 144 | 5-(CH$_2$)$_6$CH$_3$ | 5-(CH$_2$)$_4$CH(CH$_3$)$_2$ | 5-(CH$_2$)$_3$CH(CH$_3$)CH$_2$CH$_3$ |
| 145 | 5-(CH$_2$)$_7$CH$_3$ | 5-(CH$_2$)$_5$CH(CH$_3$)$_2$ | 5-(CH$_2$)$_4$CH(CH$_3$)CH$_2$CH$_3$ |
| 146 | 5-(CH$_2$)$_8$CH$_3$ | 5-(CH$_2$)$_6$CH(CH$_3$)$_2$ | 5-(CH$_2$)$_5$CH(CH$_3$)CH$_2$CH$_3$ |
| 147 | 5-(CH$_2$)$_9$CH$_3$ | 5-(CH$_2$)$_7$CH(CH$_3$)$_2$ | 5-(CH$_2$)$_6$CH(CH$_3$)CH$_2$CH$_3$ |
| 148 | 5-(CH$_2$)$_{11}$CH$_3$ | 5-(CH$_2$)$_9$CH(CH$_3$)$_2$ | 5-(CH$_2$)$_8$CH(CH$_3$)CH$_2$CH$_3$ |
| 149 | 5-(CH$_2$)$_{15}$CH$_3$ | 5-(CH$_2$)$_{13}$CH(CH$_3$)$_2$ | 5-(CH$_2$)$_{12}$CH(CH$_3$)CH$_2$CH$_3$ |
| 150 | 6-(CH$_2$)$_{11}$CH$_3$ | 6-(CH$_2$)$_9$CH(CH$_3$)$_2$ | 6-(CH$_2$)$_8$CH(CH$_3$)CH$_2$CH$_3$ |

TABLE 7

|    | Column 1 | Column 2 | Column 3 |
|----|----------|----------|----------|
| | Z = O, R$^1$ = H, R$^3$ = 2'-F, R$^4$ = 6'-F, R$^2$ = | | |
| 1  | H | 7-(4-Cl—Ph) | 7-CH$_2$CH=CH(CH$_2$)$_6$CH$_3$ |
| 2  | 7-Cl | 7-(4-F—Ph) | 7-CH$_2$CH=CH(CH$_2$)$_2$CH$_3$ |
| 3  | 7-F | 7-CH$_2$Ph | 7-OCH$_2$CH=CH(CH$_2$)$_6$CH$_3$ |
| 4  | 7-Br | 7-CH$_2$CH$_2$Ph | 7-OCH$_2$CH=CH(CH$_2$)$_2$CH$_3$ |
| 5  | 7-CF$_3$ | 7-CH$_2$Ph-4-F | 7-OCH$_2$Ph-4-F |
| 6  | 7-Ph | 7-CH$_2$Ph-4-Cl | 7-OCH$_2$CH$_2$Ph-4-F |
| 7  | 7-Py | 7-CH$_2$Ph-4-CF$_3$ | 7-CH$_2$C≡C—(CH$_2$)$_4$CH$_3$ |
| 8  | 7-OPh | 7-(4-CH$_3$(CH$_2$)$_4$Ph) | 7-OCH$_2$C≡C—(CH$_2$)$_4$CH$_3$ |
| 9  | 7-SPh | 7-CH$_2$Ph-4-(CH$_2$)$_9$CH$_3$ | 7-CH$_2$CH=CH—CH$_2$Ph |
| 10 | 7-OPy | 7-CH$_2$Ph-4-(CH$_2$)$_4$CH$_3$ | 7-OCH$_2$CH=CH—CH$_2$Ph |
| 11 | 8-Cl | 8-(4-Cl—Ph) | 8-CH$_2$CH=CH(CH$_2$)$_6$CH$_3$ |
| 12 | 8-CF$_3$ | 8-CH$_2$Ph | 8-OCH$_2$CH=CH(CH$_2$)$_6$CH$_3$ |
| 13 | 8-Ph | 8-CH$_2$CH$_2$Ph | 8-OCH$_2$CH=CH(CH$_2$)$_2$CH$_3$ |
| 14 | 8-OPh | 8-CH$_2$Ph-4-CF$_3$ | 8-CH$_2$C≡C—(CH$_2$)$_4$CH$_3$ |
| 15 | 7-O(CH$_2$)$_5$CH$_3$ | 7-O(CH$_2$)$_3$CH(CH$_3$)$_2$ | 7-O(CH$_2$)$_2$CH(CH$_3$)CH$_2$CH$_3$ |
| 16 | 7-O(CH$_2$)$_6$CH$_3$ | 7-O(CH$_2$)$_4$CH(CH$_3$)$_2$ | 7-O(CH$_2$)$_3$CH(CH$_3$)CH$_2$CH$_3$ |
| 17 | 7-O(CH$_2$)$_7$CH$_3$ | 7-O(CH$_2$)$_5$CH(CH$_3$)$_2$ | 7-O(CH$_2$)$_4$CH(CH$_3$)CH$_2$CH$_3$ |
| 18 | 7-O(CH$_2$)$_8$CH$_3$ | 7-O(CH$_2$)$_6$CH(CH$_3$)$_2$ | 7-O(CH$_2$)$_5$CH(CH$_3$)CH$_2$CH$_3$ |
| 19 | 7-O(CH$_2$)$_9$CH$_3$ | 7-O(CH$_2$)$_7$CH(CH$_3$)$_2$ | 7-O(CH$_2$)$_6$CH(CH$_3$)CH$_2$CH$_3$ |
| 20 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 21 | 7-O(CH$_2$)$_{15}$CH$_3$ | 7-O(CH$_2$)$_{13}$CH(CH$_3$)$_2$ | 7-O(CH$_2$)$_{12}$CH(CH$_3$)CH$_2$CH$_3$ |
| 22 | 8-O(CH$_2$)$_{11}$CH$_3$ | 8-O(CH$_2$)$_9$CH(CH$_3$)$_2$ | 8-O(CH$_2$)$_8$CH(CH$_3$)CH$_2$CH$_3$ |

TABLE 7-continued

| | Column 1 | Column 2 | Column 3 |
|---|---|---|---|
| 23 | 7-(CH$_2$)$_5$CH$_3$ | 7-(CH$_2$)$_3$CH(CH$_3$)$_2$ | 7-(CH$_2$)$_2$CH(CH$_3$)CH$_2$CH$_3$ |
| 24 | 7-(CH$_2$)$_6$CH$_3$ | 7-(CH$_2$)$_4$CH(CH$_3$)$_2$ | 7-(CH$_2$)$_3$CH(CH$_3$)CH$_2$CH$_3$ |
| 25 | 7-(CH$_2$)$_7$CH$_3$ | 7-(CH$_2$)$_5$CH(CH$_3$)$_2$ | 7-(CH$_2$)$_4$CH(CH$_3$)CH$_2$CH$_3$ |
| 26 | 7-(CH$_2$)$_8$CH$_3$ | 7-(CH$_2$)$_6$CH(CH$_3$)$_2$ | 7-(CH$_2$)$_5$CH(CH$_3$)CH$_2$CH$_3$ |
| 27 | 7-(CH$_2$)$_9$CH$_3$ | 7-(CH$_2$)$_7$CH(CH$_3$)$_2$ | 7-(CH$_2$)$_6$CH(CH$_3$)CH$_2$CH$_3$ |
| 28 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |
| 29 | 7-(CH$_2$)$_{15}$CH$_3$ | 7-(CH$_2$)$_{13}$CH(CH$_3$)$_2$ | 7-(CH$_2$)$_{12}$CH(CH$_3$)CH$_2$CH$_3$ |
| 30 | 8-(CH$_2$)$_{11}$CH$_3$ | 8-(CH$_2$)$_9$CH(CH$_3$)$_2$ | 8-(CH$_2$)$_8$CH(CH$_3$)CH$_2$CH$_3$ |
| | $Z = O, R^1 = H, R^3 = 2'$-F, $R^4 = 6'$-Cl, $R^2 =$ | | |
| 31 | H | 7-(4-Cl—Ph) | 7-CH$_2$CH=CH(CH$_2$)$_6$CH$_3$ |
| 32 | 7-Cl | 7-(4-F—Ph) | 7-CH$_2$CH=CH(CH$_2$)$_2$CH$_3$ |
| 33 | 7-F | 7-CH$_2$Ph | 7-OCH$_2$CH=CH(CH$_2$)$_6$CH$_3$ |
| 34 | 7-Br | 7-CH$_2$CH$_2$Ph | 7-OCH$_2$CH=CH(CH$_2$)$_2$CH$_3$ |
| 35 | 7-CF$_3$ | 7-CH$_2$Ph-4-F | 7-OCH$_2$Ph-4-F |
| 36 | 7-Ph | 7-CH$_2$Ph-4-Cl | 7-OCH$_2$CH$_2$Ph-4-F |
| 37 | 7-Py | 7-CH$_2$Ph-4-CF$_3$ | 7-CH$_2$C≡C—(CH$_2$)$_4$CH$_3$ |
| 38 | 7-OPh | 7-(4-CH$_3$(CH$_2$)$_4$Ph) | 7-OCH$_2$C≡C—(CH$_2$)$_4$CH$_3$ |
| 39 | 7-SPh | 7-CH$_2$Ph-4-(CH$_2$)$_9$CH$_3$ | 7-CH$_2$CH=CH—CH$_2$Ph |
| 40 | 7-OPy | 7-CH$_2$Ph-4-(CH$_2$)$_4$CH$_3$ | 7-OCH$_2$CH=CH—CH$_2$Ph |
| 41 | 8-Cl | 8-(4-Cl—Ph) | 8-CH$_2$CH=CH(CH$_2$)$_6$CH$_3$ |
| 42 | 8-CF$_3$ | 8-CH$_2$Ph | 8-OCH$_2$CH=CH(CH$_2$)$_6$CH$_3$ |
| 43 | 8-Ph | 8-CH$_2$CH$_2$Ph | 8-OCH$_2$CH=CH(CH$_2$)$_2$CH$_3$ |
| 44 | 8-OPh | 8-CH$_2$Ph-4-CF$_3$ | 8-CH$_2$C≡C—(CH$_2$)$_4$CH$_3$ |
| 45 | 7-O(CH$_2$)$_5$CH$_3$ | 7-O(CH$_2$)$_3$CH(CH$_3$)$_2$ | 7-O(CH$_2$)$_2$CH(CH$_3$)CH$_2$CH$_3$ |
| 46 | 7-O(CH$_2$)$_6$CH$_3$ | 7-O(CH$_2$)$_4$CH(CH$_3$)$_2$ | 7-O(CH$_2$)$_3$CH(CH$_3$)CH$_2$CH$_3$ |
| 47 | 7-O(CH$_2$)$_7$CH$_3$ | 7-O(CH$_2$)$_5$CH(CH$_3$)$_2$ | 7-O(CH$_2$)$_4$CH(CH$_3$)CH$_2$CH$_3$ |
| 48 | 7-O(CH$_2$)$_8$CH$_3$ | 7-O(CH$_2$)$_6$CH(CH$_3$)$_2$ | 7-O(CH$_2$)$_5$CH(CH$_3$)CH$_2$CH$_3$ |
| 49 | 7-O(CH$_2$)$_9$CH$_3$ | 7-O(CH$_2$)$_7$CH(CH$_3$)$_2$ | 7-O(CH$_2$)$_6$CH(CH$_3$)CH$_2$CH$_3$ |
| 50 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 51 | 7-O(CH$_2$)$_{15}$CH$_3$ | 7-O(CH$_2$)$_{13}$CH(CH$_3$)$_2$ | 7-O(CH$_2$)$_{12}$CH(CH$_3$)CH$_2$CH$_3$ |
| 52 | 8-O(CH$_2$)$_{11}$CH$_3$ | 8-O(CH$_2$)$_9$CH(CH$_3$)$_2$ | 8-O(CH$_2$)$_8$CH(CH$_3$)CH$_2$CH$_3$ |
| 53 | 7-(CH$_2$)$_5$CH$_3$ | 7-(CH$_2$)$_3$CH(CH$_3$)$_2$ | 7-(CH$_2$)$_2$CH(CH$_3$)CH$_2$CH$_3$ |
| 54 | 7-(CH$_2$)$_6$CH$_3$ | 7-(CH$_2$)$_4$CH(CH$_3$)$_2$ | 7-(CH$_2$)$_3$CH(CH$_3$)CH$_2$CH$_3$ |
| 55 | 7-(CH$_2$)$_7$CH$_3$ | 7-(CH$_2$)$_5$CH(CH$_3$)$_2$ | 7-(CH$_2$)$_4$CH(CH$_3$)CH$_2$CH$_3$ |
| 56 | 7-(CH$_2$)$_8$CH$_3$ | 7-(CH$_2$)$_6$CH(CH$_3$)$_2$ | 7-(CH$_2$)$_5$CH(CH$_3$)CH$_2$CH$_3$ |
| 57 | 7-(CH$_2$)$_9$CH$_3$ | 7-(CH$_2$)$_7$CH(CH$_3$)$_2$ | 7-(CH$_2$)$_6$CH(CH$_3$)CH$_2$CH$_3$ |
| 58 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |
| 59 | 7-(CH$_2$)$_{15}$CH$_3$ | 7-(CH$_2$)$_{13}$CH(CH$_3$)$_2$ | 7-(CH$_2$)$_{12}$CH(CH$_3$)CH$_2$CH$_3$ |
| 60 | 8-(CH$_2$)$_{11}$CH$_3$ | 8-(CH$_2$)$_9$CH(CH$_3$)$_2$ | 8-(CH$_2$)$_8$CH(CH$_3$)CH$_2$CH$_3$ |
| | $Z = O, R^1 = 8$-Cl, $R^3 = 2'$-F, $R^4 = 6'$-F, $R^2 =$ | | |
| 61 | H | 7-(4-Cl—Ph) | 7-CH$_2$CH=CH(CH$_2$)$_6$CH$_3$ |
| 62 | 7-Cl | 7-(4-F—Ph) | 7-CH$_2$CH=CH(CH$_2$)$_2$CH$_3$ |
| 63 | 7-F | 7-CH$_2$Ph | 7-OCH$_2$CH=CH(CH$_2$)$_6$CH$_3$ |
| 64 | 7-Br | 7-CH$_2$CH$_2$Ph | 7-OCH$_2$CH=CH(CH$_2$)$_2$CH$_3$ |
| 65 | 7-CF$_3$ | 7-CH$_2$Ph-4-F | 7-OCH$_2$Ph-4-F |
| 66 | 7-Ph | 7-CH$_2$Ph-4-Cl | 7-OCH$_2$CH$_2$Ph-4-F |
| 67 | 7-Py | 7-CH$_2$Ph-4-CF$_3$ | 7-CH$_2$C≡C—(CH$_2$)$_4$CH$_3$ |
| 68 | 7-OPh | 7-(4-CH$_3$(CH$_2$)$_4$Ph) | 7-OCH$_2$C≡C—(CH$_2$)$_4$CH$_3$ |
| 69 | 7-SPh | 7-CH$_2$Ph-4-(CH$_2$)$_9$CH$_3$ | 7-CH$_2$CH=CH—CH$_2$Ph |
| 70 | 7-OPy | 7-CH$_2$Ph-4-(CH$_2$)$_4$CH$_3$ | 7-OCH$_2$CH=CH—CH$_2$Ph |
| 71 | 8-Cl | 8-(4-Cl—Ph) | 8-CH$_2$CH=CH(CH$_2$)$_6$CH$_3$ |
| 72 | 8-CF$_3$ | 8-CH$_2$Ph | 8-OCH$_2$CH=CH(CH$_2$)$_6$CH$_3$ |
| 73 | 8-Ph | 8-CH$_2$CH$_2$Ph | 8-OCH$_2$CH=CH(CH$_2$)$_2$CH$_3$ |
| 74 | 8-OPh | 8-CH$_2$Ph-4-CF$_3$ | 8-CH$_2$C≡C—(CH$_2$)$_4$CH$_3$ |
| 75 | 7-O(CH$_2$)$_5$CH$_3$ | 7-O(CH$_2$)$_3$CH(CH$_3$)$_2$ | 7-O(CH$_2$)$_2$CH(CH$_3$)CH$_2$CH$_3$ |
| 76 | 7-O(CH$_2$)$_6$CH$_3$ | 7-O(CH$_2$)$_4$CH(CH$_3$)$_2$ | 7-O(CH$_2$)$_3$CH(CH$_3$)CH$_2$CH$_3$ |
| 77 | 7-O(CH$_2$)$_7$CH$_3$ | 7-O(CH$_2$)$_5$CH(CH$_3$)$_2$ | 7-O(CH$_2$)$_4$CH(CH$_3$)CH$_2$CH$_3$ |
| 78 | 7-O(CH$_2$)$_8$CH$_3$ | 7-O(CH$_2$)$_6$CH(CH$_3$)$_2$ | 7-O(CH$_2$)$_5$CH(CH$_3$)CH$_2$CH$_3$ |
| 79 | 7-O(CH$_2$)$_9$CH$_3$ | 7-O(CH$_2$)$_7$CH(CH$_3$)$_2$ | 7-O(CH$_2$)$_6$CH(CH$_3$)CH$_2$CH$_3$ |
| 80 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 81 | 7-O(CH$_2$)$_{15}$CH$_3$ | 7-O(CH$_2$)$_{13}$CH(CH$_3$)$_2$ | 7-O(CH$_2$)$_{12}$CH(CH$_3$)CH$_2$CH$_3$ |
| 82 | 8-O(CH$_2$)$_{11}$CH$_3$ | 8-O(CH$_2$)$_9$CH(CH$_3$)$_2$ | 8-O(CH$_2$)$_8$CH(CH$_3$)CH$_2$CH$_3$ |
| 83 | 7-(CH$_2$)$_5$CH$_3$ | 7-(CH$_2$)$_3$CH(CH$_3$)$_2$ | 7-(CH$_2$)$_2$CH(CH$_3$)CH$_2$CH$_3$ |
| 84 | 7-(CH$_2$)$_6$CH$_3$ | 7-(CH$_2$)$_4$CH(CH$_3$)$_2$ | 7-(CH$_2$)$_3$CH(CH$_3$)CH$_2$CH$_3$ |
| 85 | 7-(CH$_2$)$_7$CH$_3$ | 7-(CH$_2$)$_5$CH(CH$_3$)$_2$ | 7-(CH$_2$)$_4$CH(CH$_3$)CH$_2$CH$_3$ |
| 86 | 7-(CH$_2$)$_8$CH$_3$ | 7-(CH$_2$)$_6$CH(CH$_3$)$_2$ | 7-(CH$_2$)$_5$CH(CH$_3$)CH$_2$CH$_3$ |
| 87 | 7-(CH$_2$)$_9$CH$_3$ | 7-(CH$_2$)$_7$CH(CH$_3$)$_2$ | 7-(CH$_2$)$_6$CH(CH$_3$)CH$_2$CH$_3$ |
| 88 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |
| 89 | 7-(CH$_2$)$_{15}$CH$_3$ | 7-(CH$_2$)$_{13}$CH(CH$_3$)$_2$ | 7-(CH$_2$)$_{12}$CH(CH$_3$)CH$_2$CH$_3$ |
| 90 | 8-(CH$_2$)$_{11}$CH$_3$ | 8-(CH$_2$)$_9$CH(CH$_3$)$_2$ | 8-(CH$_2$)$_8$CH(CH$_3$)CH$_2$CH$_3$ |

TABLE 8

| | Column 1 | Column 2 | Column 3 |
|---|---|---|---|
| | $Z = O, R^1 = H, R^3 = 2'$-F, $R^4 = 6'$-F, $R^2 =$ | | |
| 1 | H | 7-(4-Cl—Ph) | 7-CH$_2$CH=CH(CH$_2$)$_6$CH$_3$ |
| 2 | 7-Cl | 7-(4-F—Ph) | 7-CH$_2$CH=CH(CH$_2$)$_2$CH$_3$ |
| 3 | 7-F | 7-CH$_2$Ph | 7-OCH$_2$CH=CH(CH$_2$)$_6$CH$_3$ |
| 4 | 7-Br | 7-CH$_2$CH$_2$Ph | 7-OCH$_2$CH=CH(CH$_2$)$_2$CH$_3$ |

TABLE 8-continued

| | Column 1 | Column 2 | Column 3 |
|---|---|---|---|
| 5 | 7-CF$_3$ | 7-CH$_2$Ph-4-F | 7-OCH$_2$Ph-4-F |
| 6 | 7-Ph | 7-CH$_2$Ph-4-Cl | 7-OCH$_2$CH$_2$Ph-4-F |
| 7 | 7-Py | 7-CH$_2$Ph-4-CF$_3$ | 7-CH$_2$C≡C—(CH$_2$)$_4$CH$_3$ |
| 8 | 7-OPh | 7-(4-CH$_3$(CH$_2$)$_4$Ph) | 7-OCH$_2$C≡C—(CH$_2$)$_4$CH$_3$ |
| 9 | 7-SPh | 7-CH$_2$Ph-4-(CH$_2$)$_9$CH$_3$ | 7-CH$_2$CH=CH—CH$_2$Ph |
| 10 | 7-OPy | 7-CH$_2$Ph-4-(CH$_2$)$_4$CH$_3$ | 7-OCH$_2$CH=CH—CH$_2$Ph |
| 11 | 8-Cl | 8-(4-Cl—Ph) | 8-CH$_2$CH=CH(CH$_2$)$_6$CH$_3$ |
| 12 | 8-CF$_3$ | 8-CH$_2$Ph | 8-OCH$_2$CH=CH(CH$_2$)$_6$CH$_3$ |
| 13 | 8-Ph | 8-CH$_2$CH$_2$Ph | 8-OCH$_2$CH—CH(CH$_2$)$_2$CH$_3$ |
| 14 | 8-OPh | 8-CH$_2$Ph-4-CF$_3$ | 8-CH$_2$C≡C—(CH$_2$)$_4$CH$_3$ |
| 15 | 7-O(CH$_2$)$_5$CH$_3$ | 7-O(CH$_2$)$_3$CH(CH$_3$)$_2$ | 7-O(CH$_2$)$_2$CH(CH$_3$)CH$_2$CH$_3$ |
| 16 | 7-O(CH$_2$)$_6$CH$_3$ | 7-O(CH$_2$)$_4$CH(CH$_3$)$_2$ | 7-O(CH$_2$)$_3$CH(CH$_3$)CH$_2$CH$_3$ |
| 17 | 7-O(CH$_2$)$_7$CH$_3$ | 7-O(CH$_2$)$_5$CH(CH$_3$)$_2$ | 7-O(CH$_2$)$_4$CH(CH$_3$)CH$_2$CH$_3$ |
| 18 | 7-O(CH$_2$)$_8$CH$_3$ | 7-O(CH$_2$)$_6$CH(CH$_3$)$_2$ | 7-O(CH$_2$)$_5$CH(CH$_3$)CH$_2$CH$_3$ |
| 19 | 7-O(CH$_2$)$_9$CH$_3$ | 7-O(CH$_2$)$_7$CH(CH$_3$)$_2$ | 7-O(CH$_2$)$_6$CH(CH$_3$)CH$_2$CH$_3$ |
| 20 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 21 | 7-O(CH$_2$)$_{15}$CH$_3$ | 7-O(CH$_2$)$_{13}$CH(CH$_3$)$_2$ | 7-O(CH$_2$)$_{12}$CH(CH$_3$)CH$_2$CH$_3$ |
| 22 | 8-O(CH$_2$)$_{11}$CH$_3$ | 8-O(CH$_2$)$_9$CH(CH$_3$)$_2$ | 8-O(CH$_2$)$_8$CH(CH$_3$)CH$_2$CH$_3$ |
| 23 | 7-(CH$_2$)$_5$CH$_3$ | 7-(CH$_2$)$_3$CH(CH$_3$)$_2$ | 7-(CH$_2$)$_2$CH(CH$_3$)CH$_2$CH$_3$ |
| 24 | 7-(CH$_2$)$_6$CH$_3$ | 7-(CH$_2$)$_4$CH(CH$_3$)$_2$ | 7-(CH$_2$)$_3$CH(CH$_3$)CH$_2$CH$_3$ |
| 25 | 7-(CH$_2$)$_7$CH$_3$ | 7-(CH$_2$)$_5$CH(CH$_3$)$_2$ | 7-(CH$_2$)$_4$CH(CH$_3$)CH$_2$CH$_3$ |
| 26 | 7-(CH$_2$)$_8$CH$_3$ | 7-(CH$_2$)$_6$CH(CH$_3$)$_2$ | 7-(CH$_2$)$_5$CH(CH$_3$)CH$_2$CH$_3$ |
| 27 | 7-(CH$_2$)$_9$CH$_3$ | 7-(CH$_2$)$_7$CH(CH$_3$)$_2$ | 7-(CH$_2$)$_6$CH(CH$_3$)CH$_2$CH$_3$ |
| 28 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |
| 29 | 7-(CH$_2$)$_{15}$CH$_3$ | 7-(CH$_2$)$_{13}$CH(CH$_3$)$_2$ | 7-(CH$_2$)$_{12}$CH(CH$_3$)CH$_2$CH$_3$ |
| 30 | 8-(CH$_2$)$_{11}$CH$_3$ | 8-(CH$_2$)$_9$CH(CH$_3$)$_2$ | 8-(CH$_2$)$_8$CH(CH$_3$)CH$_2$CH$_3$ |
| | Z = O, R$^1$ = H, R$^3$ = 2'-F, R$^4$ = 6'-Cl, R$^2$ = | | |
| 31 | H | 7-(4-Cl—Ph) | 7-CH$_2$CH=CH(CH$_2$)$_6$CH$_3$ |
| 32 | 7-Cl | 7-(4-F—Ph) | 7-CH$_2$CH=CH(CH$_2$)$_2$CH$_3$ |
| 33 | 7-F | 7-CH$_2$Ph | 7-OCH$_2$CH=CH(CH$_2$)$_6$CH$_3$ |
| 34 | 7-Br | 7-CH$_2$CH$_2$Ph | 7-OCH$_2$CH=CH(CH$_2$)$_2$CH$_3$ |
| 35 | 7-CF$_3$ | 7-CH$_2$Ph-4-F | 7-OCH$_2$Ph-4-F |
| 36 | 7-Ph | 7-CH$_2$Ph-4-Cl | 7-OCH$_2$CH$_2$Ph-4-F |
| 37 | 7-Py | 7-CH$_2$Ph-4-CF$_3$ | 7-CH$_2$C≡C—(CH$_2$)$_4$CH$_3$ |
| 38 | 7-OPh | 7-(4-CH$_3$(CH$_2$)$_4$Ph) | 7-OCH$_2$C≡C—(CH$_2$)$_4$CH$_3$ |
| 39 | 7-SPh | 7-CH$_2$Ph-4-(CH$_2$)$_9$CH$_3$ | 7-CH$_2$CH=CH—CH$_2$Ph |
| 40 | 7-OPy | 7-CH$_2$Ph-4-(CH$_2$)$_4$CH$_3$ | 7-OCH$_2$CH=CH—CH$_2$Ph |
| 41 | 8-Cl | 8-(4-Cl—Ph) | 8-CH$_2$CH=CH(CH$_2$)$_6$CH$_3$ |
| 42 | 8-CF$_3$ | 8-CH$_2$Ph | 8-OCH$_2$CH=CH(CH$_2$)$_6$CH$_3$ |
| 43 | 8-Ph | 8-CH$_2$CH$_2$Ph | 8-OCH$_2$CH—CH(CH$_2$)$_2$CH$_3$ |
| 44 | 8-OPh | 8-CH$_2$Ph-4-CF$_3$ | 8-CH$_2$C≡C—(CH$_2$)$_4$CH$_3$ |
| 45 | 7-O(CH$_2$)$_5$CH$_3$ | 7-O(CH$_2$)$_3$CH(CH$_3$)$_2$ | 7-O(CH$_2$)$_2$CH(CH$_3$)CH$_2$CH$_3$ |
| 46 | 7-O(CH$_2$)$_6$CH$_3$ | 7-O(CH$_2$)$_4$CH(CH$_3$)$_2$ | 7-O(CH$_2$)$_3$CH(CH$_3$)CH$_2$CH$_3$ |
| 47 | 7-O(CH$_2$)$_7$CH$_3$ | 7-O(CH$_2$)$_5$CH(CH$_3$)$_2$ | 7-O(CH$_2$)$_4$CH(CH$_3$)CH$_2$CH$_3$ |
| 48 | 7-O(CH$_2$)$_8$CH$_3$ | 7-O(CH$_2$)$_6$CH(CH$_3$)$_2$ | 7-O(CH$_2$)$_5$CH(CH$_3$)CH$_2$CH$_3$ |
| 49 | 7-O(CH$_2$)$_9$CH$_3$ | 7-O(CH$_2$)$_7$CH(CH$_3$)$_2$ | 7-O(CH$_2$)$_6$CH(CH$_3$)CH$_2$CH$_3$ |
| 50 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 51 | 7-O(CH$_2$)$_{15}$CH$_3$ | 7-O(CH$_2$)$_{13}$CH(CH$_3$)$_2$ | 7-O(CH$_2$)$_{12}$CH(CH$_3$)CH$_2$CH$_3$ |
| 52 | 8-O(CH$_2$)$_{11}$CH$_3$ | 8-O(CH$_2$)$_9$CH(CH$_3$)$_2$ | 8-O(CH$_2$)$_8$CH(CH$_3$)CH$_2$CH$_3$ |
| 53 | 7-(CH$_2$)$_5$CH$_3$ | 7-(CH$_2$)$_3$CH(CH$_3$)$_2$ | 7-(CH$_2$)$_2$CH(CH$_3$)CH$_2$CH$_3$ |
| 54 | 7-(CH$_2$)$_6$CH$_3$ | 7-(CH$_2$)$_4$CH(CH$_3$)$_2$ | 7-(CH$_2$)$_3$CH(CH$_3$)CH$_2$CH$_3$ |
| 55 | 7-(CH$_2$)$_7$CH$_3$ | 7-(CH$_2$)$_5$CH(CH$_3$)$_2$ | 7-(CH$_2$)$_4$CH(CH$_3$)CH$_2$CH$_3$ |
| 56 | 7-(CH$_2$)$_8$CH$_3$ | 7-(CH$_2$)$_6$CH(CH$_3$)$_2$ | 7-(CH$_2$)$_5$CH(CH$_3$)CH$_2$CH$_3$ |
| 57 | 7-(CH$_2$)$_9$CH$_3$ | 7-(CH$_2$)$_7$CH(CH$_3$)$_2$ | 7-(CH$_2$)$_6$CH(CH$_3$)CH$_2$CH$_3$ |
| 58 | 7-(CH$_2$)$_{11}$CH$_3$ | 7-(CH$_2$)$_9$CH(CH$_3$)$_2$ | 7-(CH$_2$)$_8$CH(CH$_3$)CH$_2$CH$_3$ |
| 59 | 7-(CH$_2$)$_{15}$CH$_3$ | 7-(CH$_2$)$_{13}$CH(CH$_3$)$_2$ | 7-(CH$_2$)$_{12}$CH(CH$_3$)CH$_2$CH$_3$ |
| 60 | 8-(CH$_2$)$_{11}$CH$_3$ | 8-(CH$_2$)$_9$CH(CH$_3$)$_2$ | 8-(CH$_2$)$_8$CH(CH$_3$)CH$_2$CH$_3$ |
| | Z = O, R$^1$ = 8-Cl, R$^3$ = 2'-F, R$^4$ = 6'-F, R$^2$ = | | |
| 61 | H | 7-(4-Cl—Ph) | 7-CH$_2$CH=CH(CH$_2$)$_6$CH$_3$ |
| 62 | 7-Cl | 7-(4-F—Ph) | 7-CH$_2$CH=CH(CH$_2$)$_2$CH$_3$ |
| 63 | 7-F | 7-CH$_2$Ph | 7-OCH$_2$CH=CH(CH$_2$)$_6$CH$_3$ |
| 64 | 7-Br | 7-CH$_2$CH$_2$Ph | 7-OCH$_2$CH=CH(CH$_2$)$_2$CH$_3$ |
| 65 | 7-CF$_3$ | 7-CH$_2$Ph-4-F | 7-OCH$_2$Ph-4-F |
| 66 | 7-Ph | 7-CH$_2$Ph-4-Cl | 7-OCH$_2$CH$_2$Ph-4-F |
| 67 | 7-Py | 7-CH$_2$Ph-4-CF$_3$ | 7-CH$_2$C≡C—(CH$_2$)$_4$CH$_3$ |
| 68 | 7-OPh | 7-(4-CH$_3$(CH$_2$)$_4$Ph) | 7-OCH$_2$C≡C—(CH$_2$)$_4$CH$_3$ |
| 69 | 7-SPh | 7-CH$_2$Ph-4-(CH$_2$)$_9$CH$_3$ | 7-CH$_2$CH=CH—CH$_2$Ph |
| 70 | 7-OPy | 7-CH$_2$Ph-4-(CH$_2$)$_4$CH$_3$ | 7-OCH$_2$CH=CH—CH$_2$Ph |
| 71 | 8-Cl | 8-(4-Cl—Ph) | 8-CH$_2$CH=CH(CH$_2$)$_6$CH$_3$ |
| 72 | 8-CF$_3$ | 8-CH$_2$Ph | 8-OCH$_2$CH=CH(CH$_2$)$_6$CH$_3$ |
| 73 | 8-Ph | 8-CH$_2$CH$_2$Ph | 8-OCH$_2$CH—CH(CH$_2$)$_2$CH$_3$ |
| 74 | 8-OPh | 8-CH$_2$Ph-4-CF$_3$ | 8-CH$_2$C≡C—(CH$_2$)$_4$CH$_3$ |
| 75 | 7-O(CH$_2$)$_5$CH$_3$ | 7-O(CH$_2$)$_3$CH(CH$_3$)$_2$ | 7-O(CH$_2$)$_2$CH(CH$_3$)CH$_2$CH$_3$ |
| 76 | 7-O(CH$_2$)$_6$CH$_3$ | 7-O(CH$_2$)$_4$CH(CH$_3$)$_2$ | 7-O(CH$_2$)$_3$CH(CH$_3$)CH$_2$CH$_3$ |
| 77 | 7-O(CH$_2$)$_7$CH$_3$ | 7-O(CH$_2$)$_5$CH(CH$_3$)$_2$ | 7-O(CH$_2$)$_4$CH(CH$_3$)CH$_2$CH$_3$ |
| 78 | 7-O(CH$_2$)$_8$CH$_3$ | 7-O(CH$_2$)$_6$CH(CH$_3$)$_2$ | 7-O(CH$_2$)$_5$CH(CH$_3$)CH$_2$CH$_3$ |
| 79 | 7-O(CH$_2$)$_9$CH$_3$ | 7-O(CH$_2$)$_7$CH(CH$_3$)$_2$ | 7-O(CH$_2$)$_6$CH(CH$_3$)CH$_2$CH$_3$ |
| 80 | 7-O(CH$_2$)$_{11}$CH$_3$ | 7-O(CH$_2$)$_9$CH(CH$_3$)$_2$ | 7-O(CH$_2$)$_8$CH(CH$_3$)CH$_2$CH$_3$ |
| 81 | 7-O(CH$_2$)$_{15}$CH$_3$ | 7-O(CH$_2$)$_{13}$CH(CH$_3$)$_2$ | 7-O(CH$_2$)$_{12}$CH(CH$_3$)CH$_2$CH$_3$ |
| 82 | 8-O(CH$_2$)$_{11}$CH$_3$ | 8-O(CH$_2$)$_9$CH(CH$_3$)$_2$ | 8-O(CH$_2$)$_8$CH(CH$_3$)CH$_2$CH$_3$ |

TABLE 8-continued

| | Column 1 | Column 2 | Column 3 |
|---|---|---|---|
| 83 | 7-$(CH_2)_5CH_3$ | 7-$(CH_2)_3CH(CH_3)_2$ | 7-$(CH_2)_2CH(CH_3)CH_2CH_3$ |
| 84 | 7-$(CH_2)_6CH_3$ | 7-$(CH_2)_4CH(CH_3)_2$ | 7-$(CH_2)_3CH(CH_3)CH_2CH_3$ |
| 85 | 7-$(CH_2)_7CH_3$ | 7-$(CH_2)_5CH(CH_3)_2$ | 7-$(CH_2)_4CH(CH_3)CH_2CH_3$ |
| 86 | 7-$(CH_2)_8CH_3$ | 7-$(CH_2)_6CH(CH_3)_2$ | 7-$(CH_2)_5CH(CH_3)CH_2CH_3$ |
| 87 | 7-$(CH_2)_9CH_3$ | 7-$(CH_2)_7CH(CH_3)_2$ | 7-$(CH_2)_6CH(CH_3)CH_2CH_3$ |
| 88 | 7-$(CH_2)_{11}CH_3$ | 7-$(CH_2)_9CH(CH_3)_2$ | 7-$(CH_2)_8CH(CH_3)CH_2CH_3$ |
| 89 | 7-$(CH_2)_{15}CH_3$ | 7-$(CH_2)_{13}CH(CH_3)_2$ | 7-$(CH_2)_{12}CH(CH_3)CH_2CH_3$ |
| 90 | 8-$(CH_2)_{11}CH_3$ | 8-$(CH_2)_9CH(CH_3)_2$ | 8-$(CH_2)_8CH(CH_3)CH_2CH_3$ |

$Z = O, R^1 = 8\text{-Cl}, R^3 = 2'\text{-F}, R^4 = 6'\text{-Cl}, R^2 =$

| | Column 1 | Column 2 | Column 3 |
|---|---|---|---|
| 91 | H | 7-(4-Cl—Ph) | 7-$CH_2CH{=}CH(CH_2)_6CH_3$ |
| 92 | 7-Cl | 7-(4-F—Ph) | 7-$CH_2CH{=}CH(CH_2)_2CH_3$ |
| 93 | 7-F | 7-$CH_2Ph$ | 7-$OCH_2CH{=}CH(CH_2)_6CH_3$ |
| 94 | 7-Br | 7-$CH_2CH_2Ph$ | 7-$OCH_2CH{=}CH(CH_2)_2CH_3$ |
| 95 | 7-$CF_3$ | 7-$CH_2Ph$-4-F | 7-$OCH_2Ph$-4-F |
| 96 | 7-Ph | 7-$CH_2Ph$-4-Cl | 7-$OCH_2CH_2Ph$-4-F |
| 97 | 7-Py | 7-$CH_2Ph$-4-$CF_3$ | 7-$CH_2C{\equiv}C{-}(CH_2)_4CH_3$ |
| 98 | 7-OPh | 7-(4-$CH_3(CH_2)_4Ph$) | 7-$OCH_2C{\equiv}C{-}(CH_2)_4CH_3$ |
| 99 | 7-SPh | 7-$CH_2Ph$-4-$(CH_2)_9CH_3$ | 7-$CH_2CH{=}CH{-}CH_2Ph$ |
| 100 | 7-OPy | 7-$CH_2Ph$-4-$(CH_2)_4CH_3$ | 7-$OCH_2CH{=}CH{-}CH_2Ph$ |
| 101 | 8-Cl | 8-(4-Cl—Ph) | 8-$CH_2CH{=}CH(CH_2)_6CH_3$ |
| 102 | 8-$CF_3$ | 8-$CH_2Ph$ | 8-$OCH_2CH{=}CH(CH_2)_6CH_3$ |
| 103 | 8-Ph | 8-$CH_2CH_2Ph$ | 8-$OCH_2CH{=}CH(CH_2)_2CH_3$ |
| 104 | 8-OPh | 8-$CH_2Ph$-4-$CF_3$ | 8-$CH_2C{\equiv}C{-}(CH_2)_4CH_3$ |
| 105 | 7-$O(CH_2)_5CH_3$ | 7-$O(CH_2)_3CH(CH_3)_2$ | 7-$O(CH_2)_2CH(CH_3)CH_2CH_3$ |
| 106 | 7-$O(CH_2)_6CH_3$ | 7-$O(CH_2)_4CH(CH_3)_2$ | 7-$O(CH_2)_3CH(CH_3)CH_2CH_3$ |
| 107 | 7-$O(CH_2)_7CH_3$ | 7-$O(CH_2)_5CH(CH_3)_2$ | 7-$O(CH_2)_4CH(CH_3)CH_2CH_3$ |
| 108 | 7-$O(CH_2)_8CH_3$ | 7-$O(CH_2)_6CH(CH_3)_2$ | 7-$O(CH_2)_5CH(CH_3)CH_2CH_3$ |
| 109 | 7-$O(CH_2)_9CH_3$ | 7-$O(CH_2)_7CH(CH_3)_2$ | 7-$O(CH_2)_6CH(CH_3)CH_2CH_3$ |
| 110 | 7-$O(CH_2)_{11}CH_3$ | 7-$O(CH_2)_9CH(CH_3)_2$ | 7-$O(CH_2)_8CH(CH_3)CH_2CH_3$ |
| 111 | 7-$O(CH_2)_{15}CH_3$ | 7-$O(CH_2)_{13}CH(CH_3)_2$ | 7-$O(CH_2)_{12}CH(CH_3)CH_2CH_3$ |
| 112 | 8-$O(CH_2)_{11}CH_3$ | 8-$O(CH_2)_9CH(CH_3)_2$ | 8-$O(CH_2)_8CH(CH_3)CH_2CH_3$ |
| 113 | 7-$(CH_2)_5CH_3$ | 7-$(CH_2)_3CH(CH_3)_2$ | 7-$(CH_2)_2CH(CH_3)CH_2CH_3$ |
| 114 | 7-$(CH_2)_6CH_3$ | 7-$(CH_2)_4CH(CH_3)_2$ | 7-$(CH_2)_3CH(CH_3)CH_2CH_3$ |
| 115 | 7-$(CH_2)_7CH_3$ | 7-$(CH_2)_5CH(CH_3)_2$ | 7-$(CH_2)_4CH(CH_3)CH_2CH_3$ |
| 116 | 7-$(CH_2)_8CH_3$ | 7-$(CH_2)_6CH(CH_3)_2$ | 7-$(CH_2)_5CH(CH_3)CH_2CH_3$ |
| 117 | 7-$(CH_2)_9CH_3$ | 7-$(CH_2)_7CH(CH_3)_2$ | 7-$(CH_2)_6CH(CH_3)CH_2CH_3$ |
| 118 | 7-$(CH_2)_{11}CH_3$ | 7-$(CH_2)_9CH(CH_3)_2$ | 7-$(CH_2)_8CH(CH_3)CH_2CH_3$ |
| 119 | 7-$(CH_2)_{15}CH_3$ | 7-$(CH_2)_{13}CH(CH_3)_2$ | 7-$(CH_2)_{12}CH(CH_3)CH_2CH_3$ |
| 120 | 8-$(CH_2)_{11}CH_3$ | 8-$(CH_2)_9CH(CH_3)_2$ | 8-$(CH_2)_8CH(CH_3)CH_2CH_3$ |

FORMULATION/UTILITY

Compounds of this invention will generally be used in formulation with an agriculturally suitable carrier comprising a liquid or solid diluent. Useful formulations include dusts, granules, baits, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

| | Weight Percent | | |
|---|---|---|---|
| | Active Ingredient | Diluent | Surfactant |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2rid Ed., Dorland Books, Caldwell, New Jersey. Typical liquid diluents and solvents are described in Marsden, *Solvents Guide*, 2nd Ed., Interscience, New York, 1950. *McCutcheon's Detergents and Emulsifiers Annual*, Allured Publ. Corp., Ridgewood, New Jersey, as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth, etc.

Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., *Pesticide Formulations*, Washington, D.C., (1988), pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", *Chemical Engineering*, Dec. 4, 1967, pp 147–148, *Perry's Chemical Engineer's Handbook*, 4th Ed., McGraw-Hill, New York, (1963), pages 8–57 and following, and WO 91/13546.

For further information regarding the an of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, (1961), pp 81–96; and Hance et at., *Weed Control Handbook,* 8th Ed., Blackwell Scientific Publications, Oxford, (1989).

In the following Examples, all percentages are by weight and all formulations are worked up in conventional ways. Compound numbers refer to compounds in Index Table A.

| Example A | |
|---|---|
| Wettable Powder | |
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |
| Example B | |
| Granule | |
| Compound 1 | 10.0% |
| attapulgite granules (low volatile matter, 0.71/0.30 mm; U.S.S. No. 25–50 sieves) | 90.0%. |
| Example C | |
| Extruded Pellet | |
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |
| Example D | |
| Emulsifiable Concentrate | |
| Compound 1 | 20.0% |
| blend of oil soluble sulfonates and polyoxyethylene ethers | 10.0% |
| isophorone | 70.0%. |

The compounds of this invention exhibit activity against a wide spectrum of foliar-feeding, fruit-feeding, seed-feeding, aquatic and soil-inhabiting arthropods (term "arthropods" includes insects, mites and nematodes) which are pests of growing and stored agronomic crops, forestry, greenhouse crops, ornamentals, nursery crops, stored food and fiber products, livestock, household, and public and animal health. Those skilled in the an will appreciate that not all compounds are equally effective against all pests. Nevertheless, all of the compounds of this invention display activity against pests that include: eggs, larvae and adults of the Order Lepidoptera; eggs, foliar-feeding, fruit-feeding, root-feeding, seed-feeding larvae and adults of the Order Coleoptera; eggs, matures and adults of the Orders Hemiptera and Homoptera; eggs, larvae, nymphs and adults of the Order Acari; eggs, immatures and adults of the Orders Thysanoptera, Orthoptera and Dermaptera; eggs, immatures and adults of the Order Diptera; and eggs, junveniles and adults of the Phylum Nematoda. The compounds of this invention are also active against pests of the Orders Hymenoptera, Isoptera, Siphonaptera, Blattaria, Thysanura and Pscoptera; pests belonging to the Class Arachnida and Phylum Platyhelminthes. The compounds are active against the following species: southern corn rootworm (*Diabrotica undecimpunctata howardi*), aster leafhopper (*Mascrosteles fascifrons*), boll weevil (*Anthonomus grandis*), fall armyworm (*Spodoptera frugiperda*), black bean aphid (*Aphis fabae*), tobacco budworm (*Heliothis virescens*), rice water weevil (*Lissorhoptrus oryzophilus*), rice leaf beetle (*Oulema oryzae*), whitebacked planthopper (*Sogatella furcifera*), green leafhopper (*Nephotettix cincticeps*), brown planthopper (*Nilaparvata lugens*), small brown planthopper (*Laodelphax striatellus*), rice stem borer (*Chilo suppressalis*), rice leafroller (*Cnaphalocrocis medinalis*), black rice stink bug (*Scotinophara lurida*), rice stink bug (*Lagynotomus elongatus*), rice bug (*Leptocorisa chinensis*), slender rice bug (*Cletus puntiger*), and southern green stink bug (*Nezara viridula*). The compounds are particularly active on mites, demonstrating ovicidal, larvicidal and chemosterilant activity against such families as Tetranychidae including *Tetranychus urticae, Tetranychus cinnabarinus, Tetranychus medanieli. Tetranychus pacificus, Tetranychus turkestani, Byrobia rubrioculus, Panonychus ulmi, Panonychus citri, Eotetranychus carpini borealis. Eotetranychus, hicoriae, Eotetranychus sexmaculatus, Eotetranychus yumensis, Eotetranychus banksi* and *Oligonychus pratensis;* Tenuipalpidae including *Brevipalpus lewisi, Brevipalpus phoenicis, Brevipalpus californicus* and *Brevipalpus obovatus;* Eriophyidae including *Phyllocoptruta oleivora, Eriophyes sheldoni, Aculus cornutus, Epitrimerus pyri* and *Eriophyes mangiferae.* See WO 90/10623 and WO 92/00673 for more detailed pest descriptions.

Compounds of this invention can also be mixed with one or more other insecticides, fungicides, nematocides, bactericides, acaricides, semiochemicals, repel/ants, attractants, pheromones, feeding stimulants or other biologically active compounds to form a multi-component pesticide giving an even broader spectrum of agricultural protection. Examples of other agricultural protectants with which compounds of this invention can be formulated are: insecticides such as avermectin B, monocrotophos, carbofuran, tetrachlorvinphos, malathion, parathion-methyl, methomyl, chlordimeform, diazinon, deltamethrin, oxamyl, fenvalerate, esfenvalerate, permethrin, profenofos, sulprofos, triflumuron, diflubenzuron, methoprene, buprofezin, thiodicarb, acephate, azinphosmethyl, chlorpyrifos, dimethoate, fipronil, flufenprox, fonophos, isofenphos, methidathion, metha-midophos, phosmet, phosphamidon, phosalone, pirimicarb, phorate, terbufos, trichlorfon, methoxychlor, bifenthrin, biphenate, cyfluthrin, fenpropathrin, fluva-linate, flucythrinate, tralomethrin, metalaldehyde and rotenone; fungicides such as carbendazim, thiuram, dodine, maneb, chloroneb, benomyl, cymoxanil, fenpropidine, fenpropimorph, triadimefon, captan, thiophanate-methyl, thiabendazole, phosethyl-Al, chlorothalonil, dichloran, metalaxyl, captafol, iprodione, oxadixyl, vinclozolin, kasugamycin, myclobutanil, tebuconazole, difenoconazole, diniconazole, fluquinconazole, ipconazole, metconazole, penconazole, propiconazole, uniconzole, flutriafol, prochloraz, pyrifenox, fenarimol, triadimenol, diclobutrazol, copper oxychloride, furalaxyl, folpet, flusilazol, blasticidin S, diclomezine, edifenphos, isoprothiolane, iprobenfos, mepronil, neo-asozin, pencycuron, probenazole, pyroquilon, tricyclazole, validamycin, and flutolanil; nematocides such as aldoxycarb, fenamiphos and fosthietan; bactericides such as oxytetracyline, streptomycin and tribasic copper surf ate; acaricides such as binapacryl, oxythioquinox, chlorobenzilate. dicofol, dienochlor, cyhexatin, hexythiazox, amitraz, propargite, tebufenpyrad and fenbutatin oxide: and biological agents such as *Bacillus thuringiensis* and baculovirus.

In certain instances, combinations with other arthropodicides having a similar spectrum of control but a different mode of action will be particularly advantageous for resistance management.

Arthropod pests are controlled and protection of agronomic crops, animal and human health is achieved by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of foliar and soil inhabiting arthropods and nematode pests and protection of agronomic and/or nonagronomic crops, comprising applying one or more of the compounds of Formula I, or compositions containing at least one such compound, in an effective amount, to the environment of the pests including the agronomic and/or nonagronomic locus of infestation, to the area to be protected, or directly on the pests to be controlled. A preferred method of application is by spraying. Alternatively, granular formulations of these compounds can be applied to the plant foliage or the soil. Other methods of application include direct and residual sprays, aerial sprays, seed coats, systemic uptake, baits, eartags, boluses, foggers, fumigants, aerosols, and many others. The compounds can be incorporated into baits that are consumed by the arthropods or in devices such as traps and the like.

The compounds of this invention can be applied in their pure state, but most often application will be of a formulation comprising one or more compounds with suitable careers, diluents, and surfactants and possibly in combination with a food depending on the contemplated end use. A preferred method of application involves spraying a water dispersion or refined off solution of the compounds. Combinations with spray oils, spray off concentrations, spreader stickers, adjuvants, and synergists and other solvents such as piperonyl butoxide often enhance compound efficacy.

The rate of application required for effective control will depend on such factors as the species of arthropod to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.001 kg/hectare may be sufficient or as much as 8 kg hectare may be required. For nonagronomic applications, effective use rates will range from about 1.0 to 50 rag/square meter but as little as 0.1 rag/square meter may be sufficient or as much as 150 mg/square meter may be required.

The following Tests demonstrate the control efficacy of compounds of this invention on specific pests. The pest control protection afforded by the compounds is not limited, however, to these species. See Index Tables A and B for compound descriptions.

Index TABLE A

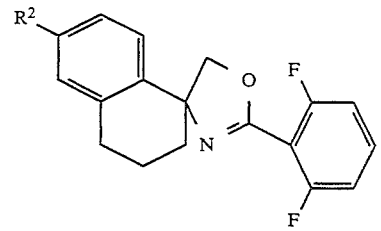

| Cmpd # | $R^2$ | Physical Properties |
|---|---|---|
| 1 | $CH_3O$ | 64–67° C. |
| 2 | $CH_3(CH_2)_4O$ | oil |
| 3 | $CH_3(CH_2)_5O$ | oil |
| 4 | $CH_3(CH_2)_6O$ | oil |
| 5 | $CH_3(CH_2)_7O$ | oil |
| 6 | $CH_3(CH_2)_8O$ | oil |
| 7 | $CH_3(CH_2)_9O$ | oil |
| 8 | $CH_3(CH_2)_9O$ | 125–131° C. (HCl Salt) |
| 9 | $CH_3(CH_2)_{10}O$ | oil |
| 10 | $CH_3(CH_2)_{11}O$ | oil |
| 11 | $CH_3(CH_2)_{11}O$ | 124–125° C. (HCl Salt) |
| 12 | $CH_3(CH_2)_{15}O$ | 67–68° C. |
| 13 | $F_3CSO_3$ | oil |
| 14 | 2,4-diCl—Ph | oil |
| 15 | 3-$NO_2$—Ph | oil |

Index TABLE B

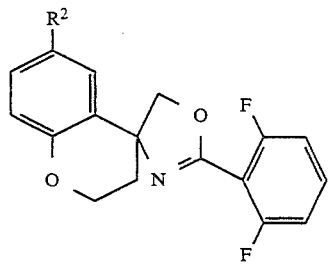

| Cmpd # | $R^2$ | Physical Properties |
|---|---|---|
| 16 | Br | 144–148° C. |
| 17 | Ph | 103–106° C. |
| 18 | 2,4-diCl—Ph | oil |
| 19 | 3,5-diCl—Ph | oil |
| 20 | 3-$CF_3$—Ph | oil |
| 21 | 3-Cl, 4-F—Ph | oil |
| 22 | 4-OMe—Ph | 50–52° C. |
| 23 | 3-$NO_2$—Ph | 63–64° C. |

Two-Spotted Spider Mite (*Tetranychus urticae*)

A solution of the test compound was prepared by dissolving it in a minimum of acetone and then adding water containing a wetting agent until the concentration of the test Compound was 10 ppm. Two-week old red kidney bean plants infested with two-spotted spider mites eggs were sprayed to m-off with the test solution using a turntable sprayer. Plants were held in a chamber at 25° C. and 50% relative humidity. Seven days after spray, these compounds gave mortality levels of 80% or higher: 2, 3, 4, 5, 7, 10, 14.

I claim:

1. A compound of the formula

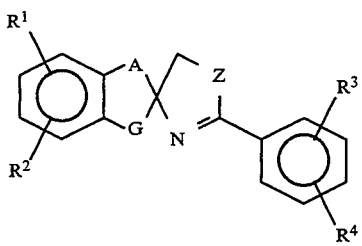

wherein
A is selected from the group a direct bond, and $C_1$-$C_3$ straight or branched chain alkylene;

G is selected from $C_1$-$C_3$ straight or branched chain alkylene; the ring containing A and G has 5-7 members;

Z is O;

$R^1$ is selected from the group H, halogen, $C_1$-$C_6$ alkyl, $C_1$-$C_6$ alkoxy, $C_1$-$C_6$ haloalkyl and $C_1$-$C_6$ haloalkoxy;

$R^2$ is selected from the group H, halogen, $C_1$-$C_{16}$ alkyl, $C_3$-$C_7$ cycloalkyl, $C_4$-$C_7$ cycloalkylalkyl, $C_1$-$C_{16}$ haloalkyl, $C_2$-$C_{16}$ alkenyl, $C_2$-$C_{16}$ haloalkenyl, $C_2$-$C_{16}$ alkynyl, $C_2$-$C_{16}$ haloalkynyl, $C_2$-$C_{16}$ alkoxyalkoxy, $OR^5$, $R^5OC(O)$—, $R^5C(O)$— and

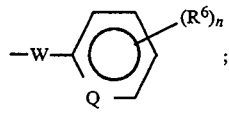

;

W is selected from the group direct bond, S, O, C(=O), C(=O)O, C(=O)O—$C_1$-$C_2$ alkylene, $C_1$-$C_4$ alkylene, O—$C_1$-$C_4$ alkylene and O—$C_2$-$C_4$ alkenylene, wherein when W is O—$C_1$-$C_4$ alkylene or O—$C_2$-$C_4$ alkenylene, the oxygen atom can be attached to either aromatic ring and when W is C(=O)O or C(=O)O—$C_1$-$C_2$, the C(=O) moiety can be attached to either aromatic ring;

Q is selected from CH and N;

$R^3$ and $R^4$ are independently selected from the group H, halogen, $C_1$-$C_6$ alkyl, $C_1$-$C_6$ haloalkyl, $C_1$-$C_6$ haloalkoxy, $C_1$-$C_6$ alkylthio, CN and $NO_2$;

$R^5$ is selected from the group H, $C_3$-$C_7$ cycloalkyl, $C_4$-$C_{16}$ cycloalkylalkyl, $C_1$-$C_{16}$ alkyl, $C_1$-$C_{16}$ haloalkyl, $C_2$-$C_{16}$ alkenyl, $C_2$-$C_{16}$ haloalkenyl, $C_2$-$C_{16}$ alkynyl and $C_2$-$C_{16}$ haloalkynyl;

$R^6$ is selected from the group halogen, $C_1$-$C_{10}$ alkyl, $C_1$-$C_{10}$ alkoxy, $C_1$-$C_{10}$ haloalkyl, $C_1$-$C_{10}$ haloalkoxy and $Si(R^7)(R^8)R^9$;

$R^7$, $R^8$ and $R^9$ are independently $C_1$-$C_3$ alkyl; and n is 0 or an integer from 1 to 5.

2. A compound according to claim 1 wherein
A is a direct bond;
G is selected from the group $C_2$-$C_3$ alkylene;
$R^1$ is selected from the group H and halogen; and
$R^3$ and $R^4$ are independently selected from the group H, F and Cl.

3. A compound according to claim 2:
2'-(2,6-difluorophenyl)-3,4-dihydro-6-octyloxyspiro-[naphthalene-1(2H),4'(5'H)-oxazole].

4. An arthropodicidal composition comprising an arthropodicidally effective amount of a compound according to claim 1 and a carrier therefor.

5. A method for controlling arthropods comprising applying to them or to their environment an effective amount of a compound according to claim 1.

UNITED STATES PATENT AND TRADEMARK OFFICE
CERTIFICATE OF CORRECTION

PATENT NO. : 5,444,079
DATED : August 22, 1995
INVENTOR(S) : Victor E. Amoo

It is certified that error appears in the above-indentified patent and that said Letters Patent is hereby corrected as shown below:

Column 43, line 15

Replace: "G is selected from $C_1$-$C_3$straight or branched chain"

with: -- G is selected from $C_1$-$C_3$ straight or branched chain --

Column 44, line 5

Replace: "C(=O)O or C(=O)O--$C_1$-$C_2$, the C(=O) moiety"

with: -- C(=O)O or C(=O)O--$C_1$-$C_2$ alkylene, the C(=O) moiety --

Column 44, line 9

Replace: "H, halogen, $C_1$-$C_6$alkyl, $C_1$-$C_6$ haloalkyl, $C_1$-$C_6$"

with: -- H, halogen, $C_1$-$C_6$ alkyl, $C_1$-$C_6$ haloalkyl, $C_1$-$C_6$ -- .

Signed and Sealed this

Thirtieth Day of April, 1996

*Attest:*

BRUCE LEHMAN

*Attesting Officer*    *Commissioner of Patents and Trademarks*